US009475766B2

(12) United States Patent
Dorsey et al.

(10) Patent No.: US 9,475,766 B2
(45) Date of Patent: Oct. 25, 2016

(54) SUBSTITUTED AROMATIC SULFUR COMPOUNDS AND METHODS OF THEIR USE

(71) Applicants: Cephalon, Inc., Frazer, PA (US); University of Hawaii, Honolulu, HI (US); University of Utah Research Foundation, Salt Lake City, UT (US)

(72) Inventors: Bruce D. Dorsey, Ambler, PA (US); Scott K. Kuwada, Honolulu, HI (US); Jay P. Theroff, West Chester, PA (US); Craig A. Zificsak, Downingtown, PA (US)

(73) Assignees: Cephalon, Inc., Frazer, PA (US); University of Utah Research Foundation, Salt Lake City, UT (US); University of Hawaii, Honolulu, HI (US)

( * ) Notice: Subject to any disclaimer, the term of this patent is extended or adjusted under 35 U.S.C. 154(b) by 95 days.

(21) Appl. No.: 13/975,483

(22) Filed: Aug. 26, 2013

(65) Prior Publication Data
US 2014/0005175 A1 Jan. 2, 2014

Related U.S. Application Data

(63) Continuation of application No. PCT/US2012/026274, filed on Feb. 23, 2012.

(60) Provisional application No. 61/446,246, filed on Feb. 24, 2011.

(51) Int. Cl.
| | |
|---|---|
| *A61K 31/66* | (2006.01) |
| *A61K 31/275* | (2006.01) |
| *A61K 31/18* | (2006.01) |
| *A61K 31/10* | (2006.01) |
| *C07C 317/32* | (2006.01) |
| *C07C 317/14* | (2006.01) |
| *C07C 317/44* | (2006.01) |
| *C07D 213/40* | (2006.01) |
| *C07D 213/57* | (2006.01) |
| *C07D 213/70* | (2006.01) |
| *C07D 215/36* | (2006.01) |
| *C07D 217/06* | (2006.01) |
| *C07D 223/10* | (2006.01) |
| *C07D 231/12* | (2006.01) |
| *C07D 235/16* | (2006.01) |
| *C07D 263/32* | (2006.01) |
| *C07D 263/56* | (2006.01) |
| *C07D 271/07* | (2006.01) |
| *C07D 271/10* | (2006.01) |
| *C07D 295/18* | (2006.01) |
| *C07D 309/08* | (2006.01) |
| *C07D 309/14* | (2006.01) |
| *C07D 333/20* | (2006.01) |

(Continued)

(52) U.S. Cl.
CPC .......... *C07C 317/32* (2013.01); *C07C 317/14* (2013.01); *C07C 317/44* (2013.01); *C07D 213/40* (2013.01); *C07D 213/57* (2013.01); *C07D 213/70* (2013.01); *C07D 215/36* (2013.01); *C07D 217/06* (2013.01); *C07D 223/10* (2013.01); *C07D 231/12* (2013.01); *C07D 235/16* (2013.01); *C07D 263/32* (2013.01); *C07D 263/56* (2013.01); *C07D 271/07* (2013.01); *C07D 271/10* (2013.01); *C07D 295/18* (2013.01); *C07D 295/192* (2013.01); *C07D 309/08* (2013.01); *C07D 309/14* (2013.01); *C07D 333/20* (2013.01); *C07D 333/24* (2013.01); *C07C 2101/02* (2013.01); *C07C 2101/04* (2013.01); *C07C 2101/14* (2013.01)

(58) Field of Classification Search
None
See application file for complete search history.

(56) References Cited

U.S. PATENT DOCUMENTS

| | | | | |
|---|---|---|---|---|
| 7,989,495 | B2 * | 8/2011 | Kuwada | ............... A61K 31/095 514/519 |
| 2005/0124590 | A1 | 6/2005 | Kuwanda | |

FOREIGN PATENT DOCUMENTS

| | | |
|---|---|---|
| JP | 2006-519205 A | 8/2006 |
| JP | 2007-505057 A | 3/2007 |

(Continued)

OTHER PUBLICATIONS

Zificsak et al., Synthesis and biological evaluation of sulfonyl acrylonitriles as novel inhibitors to peritoneal carcinomatosis, Bioorg. Med. Chem. Lett, 22:1850-1853, 2012.*

(Continued)

*Primary Examiner* — Jeffrey S Lundgren
*Assistant Examiner* — Michael Schmitt
(74) *Attorney, Agent, or Firm* — Ballard Spahr LLP

(57) ABSTRACT

Compounds of formula II are described:

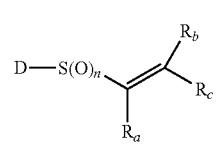

wherein D, n, $R_a$, $R_b$, and $R_c$ are as herein defined, along with pharmaceutical compositions and methods of using compounds of formula II for treating or reducing the risk of peritoneal carcinomatosis in a patient.

43 Claims, No Drawings

(51) Int. Cl.
C07D 333/24 (2006.01)
C07D 295/192 (2006.01)

(56) References Cited

FOREIGN PATENT DOCUMENTS

| JP | 2008-511576 | A | | 4/2008 | |
| JP | 2009-519340 | A | | 5/2009 | |
| WO | WO-00/64872 | A1 | | 11/2000 | |
| WO | WO 03/072038 | A2 | | 9/2003 | |
| WO | WO 2006/024611 | A2 | | 3/2006 | |
| WO | WO 2009/124272 | A2 | | 10/2009 | |
| WO | WO 2009124272 | A2 | * | 10/2009 | ............. C12Q 1/485 |
| WO | WO-2009/158587 | A1 | | 12/2009 | |

OTHER PUBLICATIONS

Armstrong et al., "Intraperitoneal Cisplatin and Paclitaxel in Ovarian Cancer," *N. Engl. J. Med.* (2006), vol. 354, pp. 34-43.
Berge et al., "Pharmaceutical Salts," *J. Pharm. Sci.* (1977), vol. 66, pp. 1-19.
Burns et al., "Identification of Inhibitors of TRAIL-induced Death (ITIDs) in the TRAIL-sensitive Colon Carcinoma Cell Line SW480 Using a Genetic Approach," *J. Biological Chem.* (2001), vol. 276, pp. 37879-37886.
Elnemr et al., "Human pancreatic cancer cells disable function of Fas receptors at several levels in Fas signal transduction pathway," *Int'l J. Oncology* (2001), vol. 18, pp. 311-316.
Fujiwara, "Intraperitoneal Chemotherapy and Intraperitoneal Washing Cytology in Management of Ovarian Cancer," *Jpn. J. Cancer Chemother.* (2000), vol. 27, pp. 354-358.
Guan et al., "An Economical and Convenient Synthesis of Vinyl Sulfones," *Synthesis* (2007), vol. 10, pp. 1465-1470.
Gunderson et al., "Adenocarcinoma of the Stomach: Areas of Failure in a Re-operation Series (Second or Symptomatic Look) Clinicopathologic Correlation and Implications for Adjuvant Therapy," *Int'l. J. Radiation Oncology Biol Phys.* (1982), vol. 8, pp. 1-11.
Hashmi et al., "Gold Catalysis: Mild Conditions for the Synthesis of Oxazoles from N-Propargylcarboxamides and Mechanistic Aspects," *Organic Lett.* (2004), vol. 6, pp. 4391-4394.
Johnstone et al., "Patterns of Disease Recurrence Following Definitive Therapy of Adenocarcinoma of the Pancreas Using Surgery and Adjuvant Radiotherapy: Correlations of a Clinical Trial," *Int'l J. Radiation Oncology Biol. Phys.* (1993), vol. 27, pp. 831-834.
Kaibara et al., "Does Extensive Dissection of Lymph Nodes Improve the Results of Surgical Treatment of Gastric Cancer?" *Amer. J. Surgery* (1990), vol. 159, pp. 218-221.
Kanellos et al., "Incidence and Prognostic Value of Positive Peritoneal Cytology in Colorectal Cancer," *Dis. Colon Rectum* (2003), vol. 46, pp. 535-539.
Korenga et al., "Trends in Survival Rates in Japanese Patients with Advanced Carcinoma of the Stomach," *Surg. Gyn Ob* (1992), vol. 174, pp. 387-393.
Landry et al., "Patterns of Failure Following Curative Resection of Gastric Carcinoma," *Int'l J. Radiation Oncology Biol. Phys.* (1990), vol. 19, pp. 1357-1362.
Leardini et al., "Radical Addition to Isonitriles: A Route to Polyfunctionalized Alkenes Through a Novel Three-Component Radical Cascade Reaction," *J. Org. Chem.* (2000), vol. 65, pp. 2763-2772.
Maruyama et al., "Progress in Gastric Cancer Surgery in Japan and Its Limits of Radicality," *World J. Surg.* (1987), vol. 11, pp. 418-425.
Nakatsuka et al., "Positive Washing Cytology in Patients with Pancreatic Cancer Indicates a Contraindication of Pancreatectomy," *J. Surg. Invest.* (1999), vol. 1, pp. 311-317.

Ozaki et al., "Transition-Metal-Catalyzed Cyanochalcogenation of Alkynes with Chalcogenocyanates," *Bull. Chem. Soc. Japan* (2011), vol. 84, pp. 155-163.
Piatnitski et al., "Efficient one-pot synthesis of substituted 2-amino-1,3,4-oxadiazoles," *Tetrahedron Lett.* (2008), vol. 49, pp. 6709-6711.
Pierce et al., "Novel Inhibitors of Cytokine-induced IκBα Phosphorylation and Endothelial Cell Adhesion Molecule Expression Show Anti-inflammatory Effects in vivo," *J. Biological Chem.* (1997), vol. 272, pp. 21096-21103.
Santala et al., "Peritoneal Cytology and Preoperative Serum CA 125 Level are Important Prognostic Indicators of Overall Survival in Advanced Endometrical Cancer," *Anticancer Res.* (2003), vol. 23, pp. 3097-3104.
Scaife et al., "Nuclear Factor κB Inhbitors Induce Adhesion-dependent Colon Cancer Apoptosis: Implications for Metastasis," *Cancer Res.* (2002), vol. 62, pp. 6870-6878.
Sugarbaker et al., "Gastrectomy, Peritonectomy, and Perioperative Intraperitoneal Chemotherapy: The Evolution of Treatment Strategies for Advanced Gastric Cancer," *Seminars in Surg. Oncol.* (2003), vol. 21, pp. 233-248.
Takeda et al., "Synthesis of Phenoxyacetic Acid Derivatives as Highly Potent Antagonists of Gastrin/Cholecystokinin-B Receptors," *Chem. Pharm. Bull.* (1998), vol. 46, pp. 434-444.
Terauchi et al., "Combination chemotherapy with paclitaxel and intraperitoneal cisplatin for ovarian cancer with disseminated lesions in the peritoneum and the diaphragm," *Int'l J. Clin. Oncol.* (2002), vol. 7, pp. 356-360.
Truce et al., "trans-1-(Arenesulfonyl)-2-arylcyclopropanes and Derivatives of Cyclopropanesulfonic Acid," *J. Org. Chem.* (1969), vol. 34, pp. 3324-3328.
Wisbeck et al., "Adenocarcinoma of the stomach: Autopsy observations with therapeutic implications for the radiation oncologist," *Radiotherapy and Oncology* (1986), vol. 7, pp. 13-18.
Yachida et al., "Implications of peritoneal washing cytology in patients with potentially resectable pancreatic cancer," *Br. J. Surg.* (2002), vol. 89, pp. 573-578.
Yu et al., "Prospective Randomized Trial of Early Postoperative Intraperitoneal Chemotherapy as an Adjuvant to Resectable Gastric Cancer," *Annals of Surgery* (1998), vol. 228, pp. 347-354.
Zhang et al., "Mechanisms of resistance to TRAIL-induced apoptosis in cancer," *Cancer Gene Therapy* (2005), vol. 12, pp. 228-237.
Notice of Reasons for Refusal issued by the Patent Office of Japan on Sep. 29, 2015 for application JP 2013-555548, filed on Feb. 24, 2011 and published as JP 2014-513677A on Jun. 5, 2014 (Applicant—Cephalon, Inc., et al. // Inventor—Dorsey, et al.) (Original—3 pages // 2 pages—English Translation).
Examination Report issued by the Intellectual Property Office of Taiwan on Dec. 24, 2016 for application TW 101105983, filed on Feb. 23, 2012 and published as TW 201309634 (Applicant—Cephalon, Inc., et al. // Inventor—Dorsey, et al.) (Original—7 pages // Translation—7 pages).
First Office Action issued by the State Intellectual Property Office of People's Republic of China on Sep. 29, 2014 for application CN 201280010475.8, filed on Feb. 23, 2012 and published as CN 10347652 on Dec. 25, 2013 (Applicant—Cephalon, Inc., et al. // Inventor—Dorsey, et al.) (Original—9 pages // Translation—12 pages).
Second Office Action issued by the State Intellectual Property Office of People's Republic of China on Jun. 15, 2015 for application CN 201280010475.8, filed on Feb. 23, 2012 and published as CN 10347652 on Dec. 25, 2013 (Applicant—Cephalon, Inc., et al. // Inventor—Dorsey, et al.) (Original—5 pages // Translation—7 pages).
Third Office Action issued by the State Intellectual Property Office of People's Republic of China on Nov. 23, 2015 for application CN 201280010475.8, filed on Feb. 23, 2012 and published as CN 10347652 on Dec. 25, 2013 (Applicant—Cephalon, Inc., et al. // Inventor—Dorsey, et al.) (Original—6 pages // Translation—6 pages).

* cited by examiner

SUBSTITUTED AROMATIC SULFUR COMPOUNDS AND METHODS OF THEIR USE

CROSS REFERENCE TO RELATED APPLICATIONS

This application is a continuation application of International Application No. PCT/US2012/026274, filed Feb. 23, 2012, which claims priority to U.S. Provisional Application Ser. No. 61/446,246, filed Feb. 24, 2011. The disclosures of the aforementioned applications are incorporated herein by reference in their entireties for all purposes.

TECHNICAL FIELD

The present invention is directed to substituted aromatic sulfur compounds and methods of using them for the treatment and prevention of cancer, in particular, peritoneal carcinomatosis.

BACKGROUND

Peritoneal carcinomatosis is a fatal form of metastasis that occurs when intra-abdominal cancers invade into the peritoneal cavity and attach to the peritoneum, a resilient tissue lining the abdominal cavity and its internal organs. Peritoneal carcinomatosis can also occur following surgical resections of intra-abdominal cancers, which releases cancer cells, blood, and lymph into the peritoneal cavity. In patients with gastric cancers, the peritoneum and liver are the major sites of recurrence following extended lymphadenectomy (Maruyama et al. World J Surg 1987, 11: 418-25; Kaibara et al. Am J Surg 1990, 159: 218-21; Korenaga et al. Surg Gynecol Obstet 1992, 174: 387-93). Following resection of ovarian cancers, the most frequent site of recurrence is the peritoneal cavity (Armstrong et al. NEJM 2006, 354: 34-43).

Locoregional recurrence within the abdominal cavity is the first site of recurrence following resection of gastric cancers in approximately 50% of patients (Sugarbaker et al. Seminars in Surgical Oncology 2003, 21: 233-248). The evidence that intra-abdominal locoregional recurrence impacts patient survival comes from multiple studies showing that the recurrent gastric cancers remain confined to the abdominal cavity even at the time of death in many cases (Gunderson et al. Int J Radiat Oncol Biol Phys 1992, 8: 1-11; Wisbeck et al. Radiother Oncol 1986, 7: 13-18; Landry et al. Int J Radiat Oncol Biol Phys 1990: 1357-1362).

Other intra-abdominal malignancies, notably pseudomyxoma peritonei, appendiceal carcinoma, and mesothelioma, commonly result in peritoneal carcinomatosis as well.

The hallmarks of cancer are invasion and metastasis. Metastasis occurs most commonly when cancer cells gain entrance into the lymphatic or hematogenous vessels through which they travel and then exit within capillary beds in secondary tissues. The rate-limiting step in metastasis is when circulating cancer cells re-adhere to tissues in secondary sites. It is well known that patients with advanced cancers often have high levels of circulating cancer cells. During surgical resections of advanced malignancies, there is often a transient increase in circulating cancer cells as well. High levels of circulating cancer cells portend poorer survival due to the metastatic potential of the circulating cells.

Most women who undergo resection of ovarian cancer experience recurrence in the peritoneal cavity with systemic dissemination much less commonly. A recent large randomized trial comparing intravenous and intraperitoneal paclitaxel (total of 6 cycles every 3 weeks) in women with stage III ovarian cancer showed an increase in long-term survival of 15.9 months for women who received intraperitoneal chemotherapy (Armstrong et al. New England Journal of Medicine 2006, 354: 34-43). This improvement in survival occurred despite the fact that only 42% of patients completed all 6 cycles of chemotherapy. These results led the NCI to declare intraperitoneal therapy as the recommended management strategy for optimally debulked ovarian cancer.

As such, improved and more effective compounds and methods for the treatment and prevention of peritoneal carcinomatosis are needed.

International Publication Number WO 2009/124272 A2 discloses methods of inhibiting proliferation of cancer cells, readhesion of cancer cells and other methods employing inhibitors of NF-κB and activators of JNK, along with compounds useful therefor.

SUMMARY

The present invention is directed to compounds of formula II, or pharmaceutically acceptable salt forms thereof:

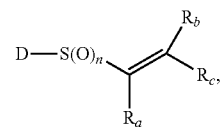

II where D, n, $R_a$, $R_b$, and $R_c$, are as defined herein.

Pharmaceutical compositions comprising compounds of formula II, or pharmaceutically acceptable salt forms thereof, are also described. The invention also encompasses methods of using the compounds of formula II, or pharmaceutically acceptable salt forms thereof.

DETAILED DESCRIPTION OF ILLUSTRATIVE EMBODIMENTS

The present invention is directed to compounds of formula II, or pharmaceutically acceptable salt forms thereof:

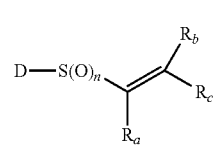

II wherein:
D is

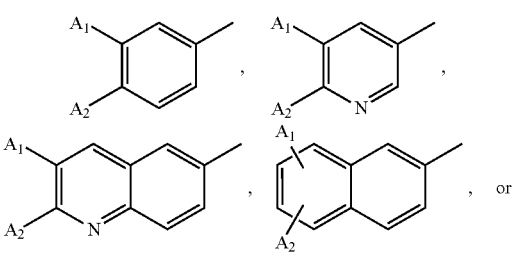

, or

-continued

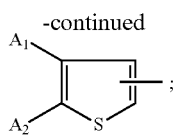

n is 0, 1 or 2;

$R_a$ is hydrogen, alkyl or phenyl;

$R_b$ is hydrogen, cyano, alkyl, phenyl, carbamoyl, or alkoxycarbonyl;

$R_c$ is hydrogen, cyano, alkyl, phenyl, carbamoyl or alkyoxycarbonyl;

$A_1$ and $A_2$ are, independently, hydrogen,

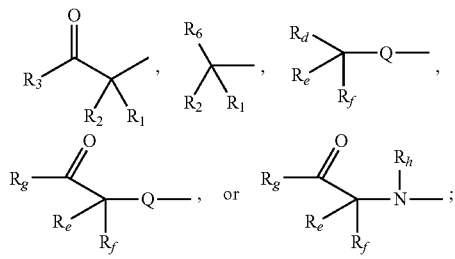

where

Q is O or S;

$R_1$ and $R_2$ are each independently substituted or unsubstituted alkyl or $R_1$ and $R_2$, together with the carbon atom to which they are attached, form a three- to seven-membered substituted or unsubstituted cycloalkyl ring, or $R_1$ and $R_2$, together with the carbon atom to which they are attached, form a substituted or unsubstituted heterocycloalkyl group;

$R_3$ is —OH, substituted or unsubstituted alkyl, substituted or unsubstituted cycloalkyl, substituted or unsubstituted cycloalkalkyl, substituted or unsubstituted alkoxy, substituted or unsubstituted aryl, substituted or unsubstituted heteroaryl, substituted or unsubstituted heterocycloalkyl, substituted or unsubstituted heterocycloalkylalkyl; or —NR$_4$R$_5$;

$R_4$ and $R_5$ are each independently H, substituted or unsubstituted alkyl, substituted or unsubstituted alkenyl, substituted or unsubstituted alkynyl, substituted or unsubstituted alkylene oxide, substituted or unsubstituted cycloalkyl, substituted or unsubstituted heterocycloalkyl, substituted or unsubstituted aryl, substituted or unsubstituted aralkyl, substituted or unsubstituted heteroaryl, substituted or unsubstituted heteroaralkyl, —COOalkyl, —COalkyl, —COcycloalkyl, —NHCOalkyl, —NHCOaryl, or —NHCOcycloalkyl; or $R_4$ and $R_5$, together with the atoms through which they are attached, form a substituted or unsubstituted heterocycloalkyl ring;

$R_6$ is substituted or unsubstituted alkyl, substituted or unsubstituted aryl, substituted or unsubstituted heteroaryl, substituted or unsubstituted aralkyl, or substituted or unsubstituted heteroaralkyl;

$R_d$ is substituted or unsubstituted alkyl, substituted or unsubstituted aryl, substituted or unsubstituted heteroaryl, substituted or unsubstituted aralkyl, or substituted or unsubstituted heteroaralkyl;

$R_e$ and $R_f$ are, independently substituted or unsubstituted alkyl, or $R_e$ and $R_f$ together with the carbon atom to which they are attached, form a three- to seven-membered substituted or unsubstituted cycloalkyl ring, or $R_e$ and $R_f$, together with the carbon atom to which they are attached, form a substituted or unsubstituted heterocycloalkyl group;

$R_g$ is —OH, substituted or unsubstituted alkyl, substituted or unsubstituted cycloalkyl, substituted or unsubstituted cycloalkalkyl, substituted or unsubstituted alkoxy, substituted or unsubstituted aryl, substituted or unsubstituted heteroaryl, substituted or unsubstituted heterocycloalkyl, substituted or unsubstituted heterocycloalkylalkyl; or —NR$_4$R$_5$; and $R_h$ is H, substituted or unsubstituted alkyl, or substituted or unsubstituted phenyl;

provided that one of $A_1$ or $A_2$ is other than hydrogen; and provided further that when D is

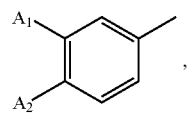

n is 2, and $R_a$, $R_c$ and $A_1$ are hydrogen, and $R_h$ is cyano, then $A_2$ is other than tert-butyl.

An embodiment of the present invention is directed to compounds of formula II, or pharmaceutically acceptable salt forms thereof, wherein D is

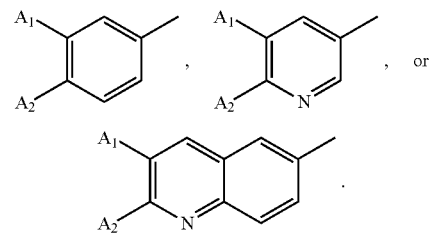

Another embodiment of the present invention is directed to compounds of formula II, or pharmaceutically acceptable salt forms thereof, wherein D is

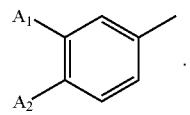

Another embodiment of the present invention is directed to compounds of formula II, or pharmaceutically acceptable salt forms thereof, wherein D is

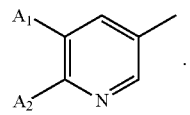

Another embodiment of the present invention is directed to compounds of formula II, or pharmaceutically acceptable salt forms thereof, wherein D is

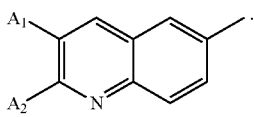

Another embodiment of the present invention is directed compounds of formula II, or pharmaceutically acceptable salt forms thereof, wherein Q is O.

A preferred embodiment of the present invention is directed to compounds according to compounds the formula

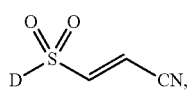

wherein D is as defined herein.

The designation for the value of D which is

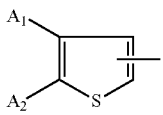

indicates that the substituents $A_1$ and $A_2$ are at the 3 and 2 positions of the thiophene ring, respectively, and that the sulfur containing side chain may be at either the 4 or 5 position of the thiophene ring,

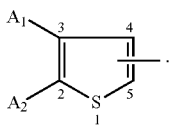

The designation for the value of D which is

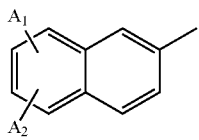

indicates that the sulfur containing side chain is at the 2-position of the naphthalene ring, while the substituents $A_1$ and $A_2$ may be at either the 5, 6, 7 or 8 positions of the naphthalene ring,

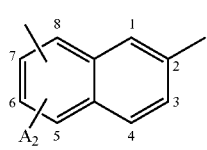

Another embodiment of the present invention is directed to compounds of formula I, or pharmaceutically acceptable salt forms thereof:

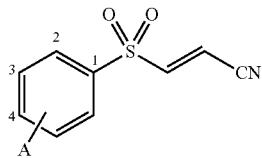

wherein A is at the 3- or 4-position of the phenyl ring; and A is

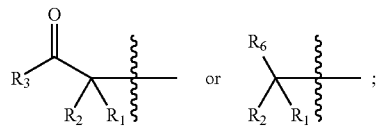

$R_1$ and $R_2$ are each independently substituted or unsubstituted alkyl or $R_1$ and $R_2$, together with the carbon atom to which they are attached, form a three- to seven-membered substituted or unsubstituted cycloalkyl ring $R_3$ is —OH, substituted or unsubstituted alkyl, substituted or unsubstituted cycloalkyl, substituted or unsubstituted cycloalkalkyl, substituted or unsubstituted alkoxy, substituted or unsubstituted aryl, substituted or unsubstituted heteroaryl, substituted or unsubstituted heterocycloalkyl, substituted or unsubstituted heterocycloalkylalkyl, or —NR$_4$R$_5$;

$R_4$ and $R_5$ are each independently H, substituted or unsubstituted alkyl, substituted or unsubstituted alkyene oxide, substituted or unsubstituted cycloalkyl, substituted or unsubstituted heterocycloalkyl, substituted or unsubstituted aryl, substituted or unsubstituted aralkyl, substituted or unsubstituted heteroaryl, substituted or unsubstituted heteroaralkyl, —COOalkyl, —COalkyl, —COcycloalkyl, —NHCOalkyl, —NHCOaryl, or —NHCOcycloalkyl; or $R_4$ and $R_5$, together with the atoms through which they are attached, form a substituted or unsubstituted heterocycloalkyl ring; and $R_6$ is substituted or unsubstituted heteroaryl.

Pharmaceutical compositions comprising a compound of formula I or II, or a pharmaceutically acceptable salt form thereof, are also within the scope of the invention.

The compounds of the invention, as well as pharmaceutical compositions comprising compounds of the invention, are useful for treating or reducing the risk of peritoneal carcinomatosis in patients. In particular, the compounds are useful for treating or reducing the risk of peritoneal carcinomatosis in patients wherein an intra-abdominal cancer is surgically removed from the patient and a pharmaceutical composition comprising a compound of formula I or II, or a pharmaceutically acceptable salt form thereof, is administered to the patient.

Accordingly, the present invention provides a method of treating or reducing the risk of peritoneal carcinomatosis in a patient that has had an intra-abdominal cancer removed, said method comprising administering to said patient a therapeutically effective amount of a compound of the present invention. In an embodiment of the invention the intra-abdominal cancer is located at or near the colon, at or near the ovary, at or near the rectum, at or near the stomach, or at or near the pancreas of the patient.

Further, the present invention provides a use of a compound of the present invention for treating or reducing the risk of peritoneal carcinomatosis is a patient that has had an intra-abdominal cancer removed. In an embodiment of the invention the intra-abdominal cancer is located at or near the colon, at or near the ovary, at or near the rectum, at or near the stomach, or at or near the pancreas of the patient.

Further, the present invention provides for the use of a compound of the present invention for the manufacture of a medicament for treating or reducing the risk of peritoneal carcinomatosis is a patient that has had an intra-abdominal cancer removed. In an embodiment of the invention, the intra-abdominal cancer is located at or near the colon, at or near the ovary, at or near the rectum, at or near the stomach, or at or near the pancreas of the patient.

In preferred embodiments of the invention, A of formula I is at the 4-position of the phenyl ring. In other embodiments, A is at the 3-position of the phenyl ring.

Preferred compounds of the invention include those wherein A is

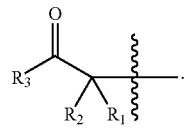

In these embodiments, $R_1$ and $R_2$ of A are preferably each independently substituted or unsubstituted alkyl, for example, —$CH_3$. In other embodiments, $R_1$ and $R_2$, together with the carbon atom to which they are attached, form a three- to seven-membered substituted or unsubstituted cycloalkyl ring, for example, cyclopropyl or cyclobutyl.

In those embodiments wherein A is

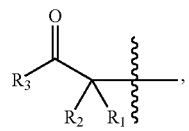

preferably, $R_3$ is —OH. In other embodiments, $R_3$ is substituted or unsubstituted alkyl. In yet other embodiments, $R_3$ is substituted or unsubstituted cycloalkyl. In still other embodiments, $R_3$ is substituted or unsubstituted cycloalkalkyl. In further embodiments, $R_3$ is substituted or unsubstituted alkoxy. In additional embodiments, $R_3$ is substituted or unsubstituted aryl. In other embodiments, $R_3$ is substituted or unsubstituted heteroaryl. In yet other embodiments, $R_3$ is substituted or unsubstituted heterocycloalkyl. In still other embodiments, $R_3$ is substituted or unsubstituted heterocycloalkylalkyl.

In other preferred embodiments wherein A is

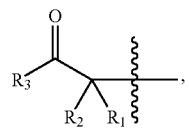

$R_3$ is preferably —$NR_4R_5$. Preferred embodiments include those wherein $R_4$ is hydrogen. In other embodiments, $R_4$ is unsubstituted alkyl, for example, —$CH_3$.

In preferred embodiments wherein A is

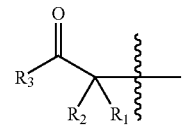

and $R_3$ is —$NR_4R_5$, $R_5$ is hydrogen. In other embodiments, $R_5$ is preferably substituted or unsubstituted alkyl. In other embodiments, $R_5$ is substituted or unsubstituted aryl. In yet other embodiments, $R_5$ is substituted or unsubstituted aralkyl. In still other embodiments, $R_5$ is substituted or unsubstituted heteroaryl. In some embodiments, $R_5$ is substituted or unsubstituted heteroaralkyl. In other embodiments, $R_5$ is substituted or unsubstituted cycloalkyl. In further embodiments, $R_5$ is substituted or unsubstituted heterocycloalkyl. In additional embodiments, $R_5$ is substituted or unsubstituted alkyene oxide. In other embodiments, $R_5$ is —NHCOcycloalkyl. In other embodiments, $R_5$ is —COOalkyl. In yet other embodiments, $R_5$ is —COalkyl. In further embodiments, $R_5$ is —NHCOalkyl. In additional embodiments, $R_5$ is —NHCOaryl.

In still other embodiments wherein A is

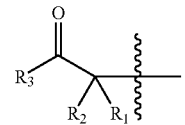

and $R_3$ is —$NR_4R_5$, wherein $R_4$ and $R_5$, together with the atoms through which they are attached, form a substituted or unsubstituted heterocycloalkyl ring, for example, substituted or unsubstituted morpholinyl, substituted or unsubstituted piperazinyl, substituted or unsubstituted tetrahydroisoquinolinyl, or substituted or unsubstituted piperidinyl.

In other embodiments, A is

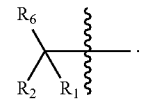

In these embodiments, $R_1$ and $R_2$ are each independently substituted or unsubstituted alkyl, for example, —$CH_3$. Alternatively, $R_1$ and $R_2$, together with the carbon atom to which they are attached, form a three- to seven-membered substituted or unsubstituted cycloalkyl ring, for example, cyclopropyl or cyclobutyl.

In those embodiments wherein A is

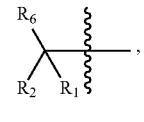

$R_6$ is a substituted or unsubstituted heteroaryl, for example, substituted or unsubstituted oxadiazolyl, substituted or unsubstituted benzoimidazolyl, substituted or unsubstituted benzooxazolyl, or substituted or unsubstituted oxazolyl.

As used herein, the term "alkyl" refers to branched or unbranched saturated hydrocarbon chain. Examples include, but are not limited to, methyl, ethyl, n-propyl, n-butyl, n-pentyl, n-hexyl, n-heptyl, n-octyl, n-nonyl, n-decyl, isopropyl, tert-butyl, isobutyl, and the like. Alkyl groups typically contain 1-10 carbon atoms, preferably 1-6 or 1-3 carbon atoms, and can be substituted or unsubstituted.

As used herein, the term "alkenyl" refers to an "alkyl" group containing the requisite number of carbon atoms as described herein for "alkyl", and which contains at least one double bond. Representative examples of alkenyl groups include, but are not limited to ethenyl, allyl, isopropenyl, and 2-methyl-1-propenyl.

As used herein, the term "alkylene" refers to a divalent alkyl radical. Examples include, but are not limited to, methylene, ethylene, propylene, and the like.

As used herein, the term "alkoxy" refers to —O-alkyl groups, wherein alkyl is as defined herein.

As used herein, the term "alkoxycarbonyl" refers to an alkyl-O(C=O)— group.

As used herein, the term "alkynyl" refers to an "alkyl" group containing the requisite number of carbon atoms as described herein for "alkyl", and which contains at least one triple bond. Representative examples of alkynyl groups include, but are not limited to, ethynyl, propargyl, and 1- and 2-butynyl.

As used herein, the term "aryl" refers to a phenyl or naphthyl group.

As used herein, the term "aralkyl" refers to an aryl group, as defined herein, bonded directly through an alkylene moiety. The alkylene moiety can have from 1-10 carbon atoms, preferably 1-6 carbon atoms, more preferably 1 or 2 carbon atoms. In addition, the alkylene moiety of the aralkyl group can be unsubstituted or substituted. In substituted alkylene embodiments, the substitutent can be any of the substituents defined herein and is preferably —OH, —NH$_2$, alkylene-OH, or alkyl.

As used herein, the term "alkylene oxide" refers to an alkylene group wherein one or more of the methylene units of the alkylene group has been replaced with an oxygen atom.

As used herein, the "carbamoyl" refers to a NH$_2$C(=O)— group.

As used herein, the term "cycloalkyl" refers to a mono or bicyclic carbocyclic ring. Examples include, but are not limited to, cyclopropyl, cyclobutyl, cyclopentyl, cyclohexyl, cycloheptyl, bicyclo[2.2.1]heptanyl, and the like. Cycloalkyl groups typically contain 3-12 carbon atoms, preferably 3-6 carbon atoms.

As used herein, the term "cycloalkalkyl" refers to a cycloalkyl group, as defined herein, bonded directly through an alkylene moiety. The alkylene moiety can have from 1-10 carbon atoms, preferably 1-6 carbon atoms, more preferably 1 or 2 carbon atoms. In addition, the alkylene moiety of the cycloalkalkyl group can be unsubstituted or substituted. In substituted alkylene embodiments, the substitutent can be any of the substituents defined herein and is preferably —OH, —NH$_2$, or alkyl.

As used herein, the term "heterocycloalkyl" refers to a mono or bicyclic carbocyclic ring containing from 1 to 5 N, O, or S atoms. Examples include, but are not limited to, pyrrolidinyl, tetrahydrofuranyl, dihydrofuranyl, tetrahydropyranyl, pyranyl, thiopyranyl, aziridinyl, oxiranyl, isoxazolidinyl, 1,3-oxazolidin-3-yl, isothiazolidinyl, 1,2-pyrazolindin-2-yl, 1,3-pyrazolidin-1-yl, piperidinyl, thiomorpholinyl, morpholinyl, 1,2-tetrahydrothiazin-2-yl, piperazinyl, and the like. One of ordinary skill in the art will understand that the connection of the heterocycloalkyl ring can be through a carbon atom or through a nitrogen heteroatom, where possible. The term "heterocycloalkyl" also includes those mono or bicyclic carbocyclic rings containing a —NH—CO— group, for example, pyrrolidinyl-2-one, piperidinyl-2-one, and azepanyl-2-one.

Included within the definition of "heterocycloalkyl" are fused ring systems, including, for example, ring systems in which an aryl or heteroaryl ring is fused to a heterocycloalkyl ring. Examples include indoline, isoindoline, chorman, and isochroman, As used herein, the term "heterocycloalkalkyl" refers to a heterocycloalkyl group, as defined herein, bonded directly through an alkylene moiety. The alkylene moiety can have from 1-10 carbon atoms, preferably 1-6 carbon atoms, more preferably 1 or 2 carbon atoms. In addition, the alkylene moiety of the heterocycloalkalkyl group can be unsubstituted or substituted. In substituted alkylene embodiments, the substitutent can be any of the substituents defined herein and is preferably —OH, —NH$_2$, or alkyl.

As used herein, the term "heteroaryl" refers to refers to an aromatic group containing 5 to 10 ring carbon atoms in which one or more ring carbon atoms are replaced by at least one hetero atom such as —O—, —N—, or —S—. Examples of heteroaryl groups include pyrrolyl, furyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, picolinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl.

As used herein, the term "heteroaralkyl" refers to a heteroaryl group, as defined herein, bonded directly through an alkylene moiety. The alkylene moiety can have from 1-10 carbon atoms, preferably 1-6 carbon atoms, more preferably 1 or 2 carbon atoms. In addition, the alkylene moiety of the aralkyl group can be unsubstituted or substituted. In substituted alkylene embodiments, the substitutent can be any of the substituents defined herein and is preferably —OH, —NH$_2$, or alkyl.

As used herein, the term "halogen" refers to fluorine, chlorine, bromine, and iodine.

As used herein, the term "substituted" or "substituent" refers to the substitution of any 1, 2, or 3 hydrogens by 1, 2, or 3 functional groups. These functional groups include, but are not limited to, —OH, —CN, —C≡CH; —C=CH$_2$, —COOH, —NH$_2$, —NHalkyl, —NHaryl, —NHC(O)Oalkyl, —NHC(O)alkyl, —NHC(O)cycloalkyl, halogen, alkyl, cycloalkyl, heteroaryl, alkoxy, alkylene-OH, alkylene oxide, cycloalkyl, heterocycloalkyl, aryl, heteroaryl, —SO$_2$alkyl, —SO$_2$—NH$_2$, —SO$_2$—NHalkyl, and —SO$_2$—NHaryl.

Compounds of the invention will be administered to a patient in a "therapeutically effective amount." As used herein, a "therapeutically effective amount" refers to an amount of a compound of the invention effective to prevent, treat, or reduce the incidence of the claimed disease or disorder. The determination of the therapeutically effective amount will depend on several factors, including the age and weight of the patient, as well as the disease or disorder to be treated. Such a determination is within the skill of those in the art.

As used herein, "pharmaceutically acceptable carrier or diluent" refers to solvents, dispersion media, coatings, antibacterial and antifungal agents, isotonic and absorption delaying agents, and the like, that are physiologically compatible. Examples of pharmaceutically acceptable carriers include one or more of water, saline, phosphate buffered saline, dextrose, glycerol, ethanol, sugars, polyalcohols such as mannitol, sorbitol, and sodium chloride. Pharmaceutically acceptable carriers may further include auxiliary substances such as wetting or emulsifying agents, preservatives, and buffers.

As used herein, "pharmaceutical composition" refers to a composition suitable for administration in medical or veterinary use. Such compounds will preferably include a compound of the invention in combination with one or more carriers and/or diluents.

As used herein, "administering" refers to any means within the art by which compounds of the invention can be delivered to the patient. Preferred administration methods include local administration, that is, administration of the compounds of the invention directly to the location where the effect of the compounds is desired, and systemic administration. Examples of administration methods include, but are not limited to, oral, enteric, sublingual, sublavial, subcutaneous, nasal, intravenous, intraarterial, intramuscular, and intraperitoneal administration. Preferred methods include local administration of a compound of the invention to the site of treatment, for example, the peritoneal cavity, via a spray or wash.

The present invention includes pharmaceutically acceptable salts of compounds of formula I. Pharmaceutically acceptable acid addition salts of the compounds of formula I include, but are not limited to, salts derived from inorganic acids such as hydrochloric, nitric, phosphoric, sulfuric, hydrobromic, hydriodic, and phosphorus, as well as the salts derived from organic acids, such as aliphatic mono- and dicarboxylic acids, phenyl-substituted alkanoic acids, hydroxy alkanoic acids, alkanedioic acids, aromatic acids, and aliphatic and aromatic sulfonic acids. Such salts thus include, but are not limited to, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, and methanesulfonate. Also contemplated are the salts of amino acids such as arginate, gluconate, galacturonate, and the like; see, for example, Berge et al., "Pharmaceutical Salts," J. of Pharmaceutical Science, 1977; 66:1-19.

The acid addition salts of the basic compounds may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are in general equivalent to their respective free base for purposes of the present invention.

Pharmaceutically acceptable base addition salts of compounds of formula I are formed with metals or amines, such as alkali and alkaline earth metal hydroxides, or of organic amines. Examples of metals used as cations include, but are not limited to, sodium, potassium, magnesium, and calcium. Examples of suitable amines include, but are not limited to, N,N'-dibenzylethylenediamine, chloroprocaine, choline, diethanolamine, ethylenediamine (ethane-1,2-diamine), N-methylglucamine, and procaine; see, for example, Berge et al., supra., 1977.

The base addition salts of acidic compounds may be prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are in general equivalent to their respective free acid for purposes of the present invention.

Some of the compounds in the present invention may exist as stereoisomers, including enantiomers, diastereomers, and geometric isomers. Geometric isomers include compounds of the present invention that have alkenyl groups, which may exist as entgegen (E) or zusammen (Z) conformations, in which case all geometric forms thereof, both entgegen and zusammen, cis and trans, and mixtures thereof, are within the scope of the present invention. Some compounds of the present invention have cycloalkyl groups, which may be substituted at more than one carbon atom, in which case all geometric forms thereof, both cis and trans, and mixtures thereof, are within the scope of the present invention. All of these forms, including (R), (S), epimers, diastereomers, cis, trans, syn, anti, (E), (Z), tautomers, and mixtures thereof, are contemplated in the compounds of the present invention.

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention The compounds of the present invention can be prepared in a number of ways well known to one skilled in the art of organic synthesis. The compounds of the present invention can be synthesized using the methods described below as well as using methods known to one skilled in the art of organic chemistry or variations thereon as appreciated by those skilled in the art. The preferred methods include, but are not limited to or by, those described below. Unless otherwise stated, starting and intermediate compounds are of commercial origin or readily synthesized by standard methods well known to one skilled in the art of organic synthesis.

The compounds of this invention may be prepared using the reactions and techniques described in this section. The reactions are performed in solvents appropriate to the reagents, and materials employed are suitable for the transformations being effected. Also, in the description of the synthetic methods below, it is to be understood that all proposed reaction conditions, including choice of solvent, reaction atmosphere, reaction temperature, duration of experiment and workup procedures are chosen to be conditions standard for that reaction which should be readily recognized by one skilled in the art of organic synthesis.

It is understood that the examples and embodiments described herein are for illustrative purposes only and that various modifications or changes in light thereof will be suggested to persons skilled in the art and are to be included within the spirit and purview of this application and the scope of the appended claims. Specific chemical transformations are listed in the ensuing schemes and one skilled in the art appreciates that a variety of different reagents may be used in place of those listed. Common replacements for such reagents can be found in, but not limited to, texts such as "Encyclopedia of Reagents for Organic Synthesis" Leo A. Paquette, John Wiley & Son Ltd (1995) or "Comprehensive Organic Transformations: A Guide to Functional Group Preparations" Richard C. Larock. Wiley-VCH and "Strategic Applications of Named Reactions in Organic Synthesis" Kurti and Czako, Elsevier, 2005 and references therein.

Scheme 1

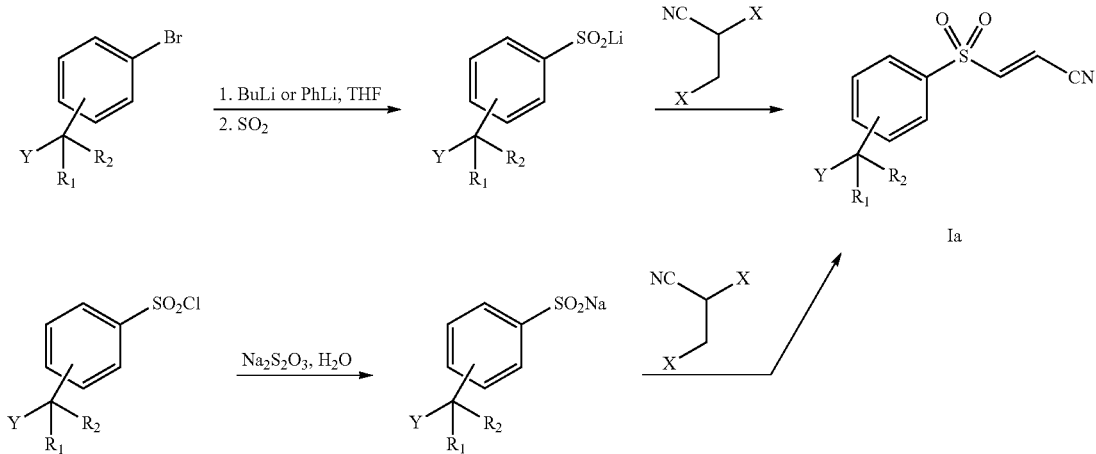

Compounds of formula Ia, for example where Y, $R_1$ and $R_2$ are, for example, alkyl, can be prepared as set forth in Scheme 1. In a first step, an aryl halide such as 3-tert-butylbromobenzene is treated with an alkyl- or aryllithium reagent such as n-butyllithium or phenyllithium in an aprotic solvent such as tetrahydrofuran or ether. The newly formed organometallic species is quenched with sulfur dioxide to furnish the sulfinic acid, which is isolated by filtration as the lithium salt. Alternatively, a phenylsulfonylchloride, such as 3-tert-butylphenylsulfonylchloride is treated with sodium sulfite in water to prepare the 3-tert-butylphenylsulfinic acid sodium salt. The lithium or sodium sulfinic acid salt is treated with a substituted 1,2-dihaloethane reagent (i.e., where X is halo) to provide the arylsulfonylethylene compound of formula Ia.

Scheme 2

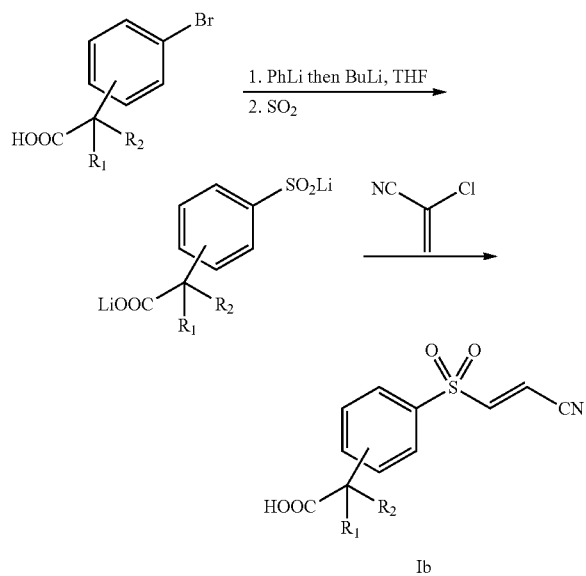

Similarly, compounds of formula Ib, where $R_1$ and $R_2$ are, for example, alkyl, may be prepared as shown in Scheme 2. For example, 2-(4-bromophenyl)isobutyric acid or 2-(3-bromophenyl)isobutyric acid is treated with phenyl lithium followed by n-butyllithium then quenched with sulfur dioxide to furnish the dilithium salt. The dilithium salt is reacted with 2-chloroacrylonitrile in a mixture of water:methanol:acetic acid. Once addition of the sulfinic acid to the 2-chloroacrylonitrile is complete, aqueous workup is followed by treatment with an amine base such as triethylamine to afford elimination of the chloride and formation of the sulfonylacrylonitrile of formula Ib.

Scheme 3

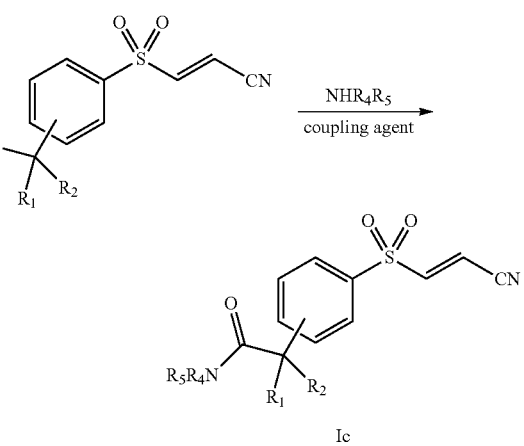

For the preparation of amides of the general formula Ic, as shown in Scheme 3, and, for example, where $R_1$ and $R_2$ are methyl, either 2-[4-((E)-2-cyano-ethenesulfonyl)-phenyl]-2-methyl-propionic acid or 2-[3-((E)-2-cyano-ethenesulfonyl)-phenyl]-2-methyl-propionic acid prepared as in Scheme 2 may be reacted with a primary or secondary amine, where $R_4$ and $R_5$ are as defined herein, or are synthetic precursors thereto, in the presence of an amide coupling reagent in an aprotic solvent such as dichloromethane, tetrahydrofuran, dimethylformamide, and the like. Examples of suitable amide coupling reagents include carbodiimides (e.g. dicyclohexylcarbodiimide or N-(3-dimethylaminopropyl)-N'-ethylcarbodiimide hydrochloride), phosphonium salts (e.g. (benzotriazol-1-yloxy)tris (dimethylamino)phosphonium hexafluorophosphate or bromotripyrrolidinophosphonium hexafluorophosphate), propylphosphonic anhydride, and the like. Following amide bond formation, the compounds are readily isolated by purification on silica gel or by reverse-phase HPLC.

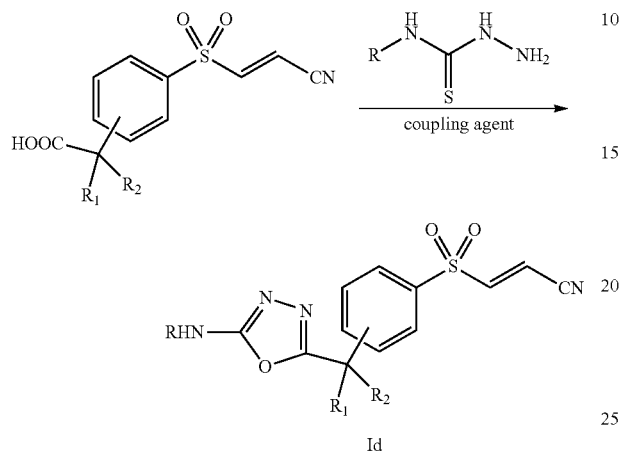

Id

The formation of the heterocyclic derivative of the general formula Id is shown in Scheme 4. $R_1$ and $R_2$ are as defined herein. R is a substituent as defined herein. Similar to a procedure known in the art (Piatnitski Checkler, E. L.; Elokdah, H. M.; Butera, J. Tetrahedron Lett. 2008, 49, 6709.), for example where $R_1$ and $R_2$ are methyl, reaction of 2-[4-((E)-2-cyano-ethenesulfonyl)-phenyl]-2-methyl-propionic acid or 2-[3-((E)-2-cyano-ethenesulfonyl)-phenyl]-2-methyl-propionic acid with thiosemicarbazides in the presence of a coupling agent, for example N-(3-Dimethylaminopropyl)-N'-ethylcarbodiimide hydrochloride furnishes the 2-substituted amino-1,3,4-oxadiazoles of general formula Id.

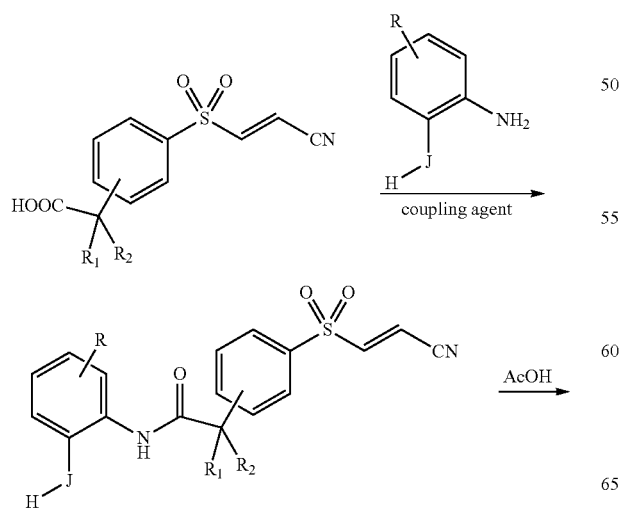

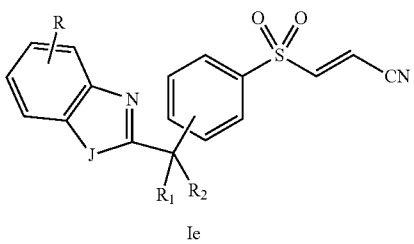

Ie

The formation of benzimidazole or benzoxazole compounds of general formula Ie, where J is O or $NR^4$, where $R^4$ as defined herein, $R_1$ and $R_2$ are as defined herein, and R is one or more substituents as defined herein, is shown in Scheme 5. The formation begins with an amide coupling as described in Scheme 3, followed by heating the 2-hydroxy- or 2-amino-phenylamide in the presence of acetic acid to furnish the benzoxazole or benzimidazole compound of general formula Ie.

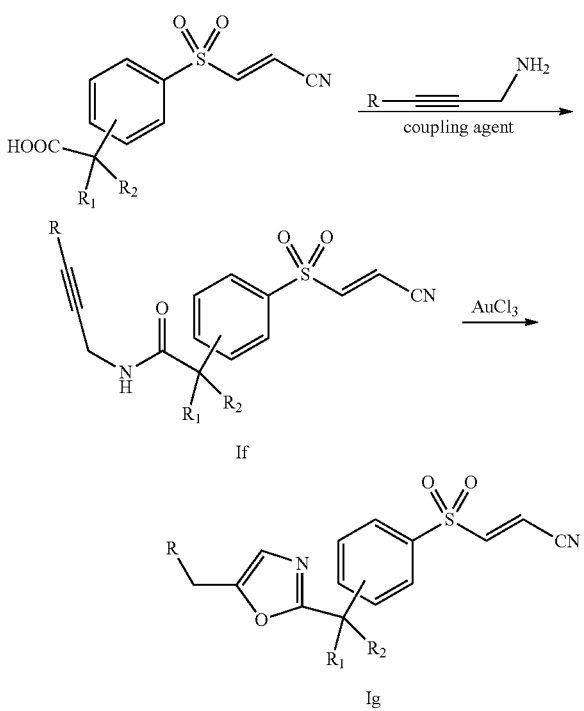

Scheme 6 describes the preparation of oxazole derivatives of general formula If, where $R_1$ and $R_2$ are as defined herein and R is a substituent as defined herein. A propargylic amine is coupled to a carboxylic acid to furnish a propargylic amide of general formula If by means of an amide coupling as described in Scheme 3. Treatment of the propargylic amide with catalytic gold(III) chloride in acetonitrile by methods known in the art (Hashmi, A. S. K.; Weyrauch, J. P.; Frey, W.; Bats, J. W. Org. Lett. 2004, 6, 4391.) furnishes the cycloisomerized product of general formula Ig.

Scheme 7

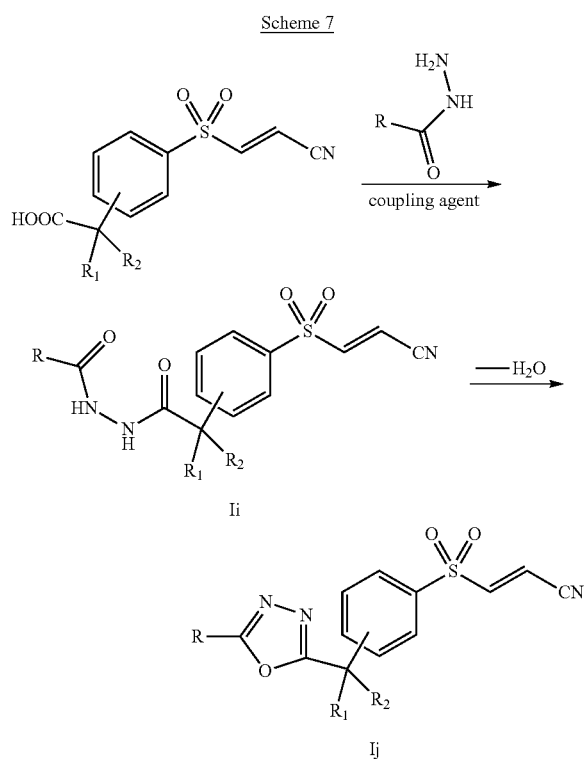

Compounds of general formula Ij, where $R_1$ and $R_2$ are as defined herein and R is a substituent as defined herein may be prepared from, for example, 2-[4-((E)-2-cyano-ethene-sulfonyl)-phenyl]-2-methyl-propionic acid or 2-[3-((E)-2-cyano-ethenesulfonyl)-phenyl]-2-methyl-propionic acid, by coupling with an acyl hydrazide in the presence of N-(3-dimethylaminopropyl)-N'-ethylcarbodiimide hydrochloride or other suitable amide coupling reagent in a polar aprotic solvent such as acetonitrile to afford the acylhydrazide of general formula Ii. 2-Substituted-1,3,4-oxadiazoles of general formula Ij may be prepared from the acylhydrazide by dehydration, which may be accomplished with a reagent such as phosphorous oxychloride, thionyl chloride or Burgess' reagent, with or without the presence of a polar or non-polar, aprotic solvent, such as acetonitrile or dioxane.

Preventing the implantation of rogue cancer cells within the peritoneum is critical to preventing metastasis and further disease development.

NF-kB (nuclear factor kappa B) is transiently but strongly activated during the adhesion of adenocarcinoma cells (Scaife et al. Cancer Research 2002, 62: 6870-78). Treatment of suspended adenocarcinoma cells with compounds of the invention resulted in an induction of apoptosis during adhesion. In a peritoneal carcinomatosis model in mice, pretreatment 4 hours before IP injection of human colon and pancreatic adenocarcinoma cells followed by 3 more treatments over 9 days with compounds of the invention (e.g., 1 mg/kg) significantly inhibited peritoneal tumor implantation. Compounds of the invention also inhibited colon cancer cell proliferation (e.g., 10 μM) and colon cancer xenografts in athymic mice.

Compounds of the invention target multiple kinases in cancer cells. Compounds of the invention inhibit IKK-mediated phosphorylation of IkB, the endogenous inhibitor of NF-kB, but activate JNK and p38/SAPK as well (Pierce et al. J Biol Chem 1999). It has now been shown that JNK activation is important for the apoptotic activity of compounds of the invention in human colon and pancreatic cancer cells. Furthermore, JNK activation targets FLIP (FLICE inhibitory protein) for degradation in cancer cells. FLICE (caspase 8) is commonly overexpressed in cancers and a critical mediator of death receptor-induced apoptosis. FLIP expression is regulated by NF-kB and treatment of cancer cells with compounds of the invention rapidly decreases FLIP expression in a JNK-dependent fashion. Inhibition of FLIP expression in colon and pancreatic cancer cells enhanced the ability of compounds of the invention to induce apoptosis of the cells during adhesion while overexpression of FLIP in colon and pancreatic cancer cells rendered them resistant to the apoptotic effects of compounds of the invention. It has thus been determined that the apoptotic activity in cancer cells of the compounds of the invention requires the dual activities on NF-kB and JNK.

The results of testing certain compounds of the invention against various cell lines is shown in Table I below. SU86 is a pancreatic cancer cell line. HT29 is a colon cancer cell line. BxPC3 is a pancreatic cell line. A2780 is an ovarian cancer cell line.

TABLE I

| No. | Compound | SU86 10 μM | HT29 10 μM | BxPC3 10 μM | A2780 10 μM |
|---|---|---|---|---|---|
| 1 | ![structure] | ** | ** | * | * |
| 2 | ![structure] | * | ** | ** | * |

TABLE I-continued
| No. | Compound | SU86 10 μM | HT29 10 μM | BxPC3 10 μM | A2780 10 μM |
|---|---|---|---|---|---|
| 3 | 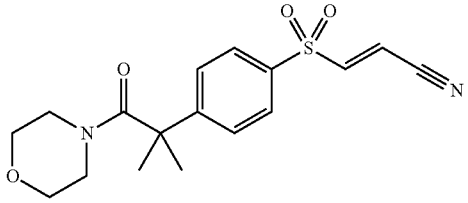 [SMILES: CC(C)(C(=O)N1CCOCC1)c1ccc(S(=O)(=O)/C=C/C#N)cc1] | * | * |  |  |
| 4 | 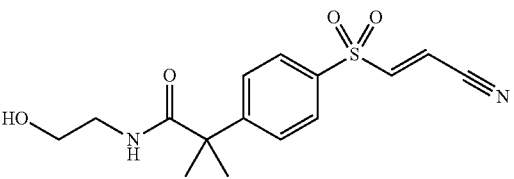 [SMILES: CC(C)(C(=O)NCCO)c1ccc(S(=O)(=O)/C=C/C#N)cc1] | * | ** | * | * |
| 5 | 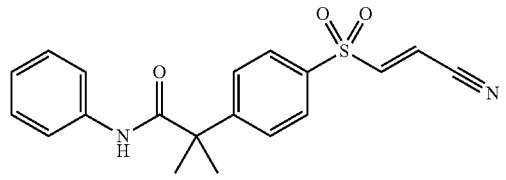 [SMILES: CC(C)(C(=O)Nc1ccccc1)c1ccc(S(=O)(=O)/C=C/C#N)cc1] | ** | * | * | * |
| 6 | 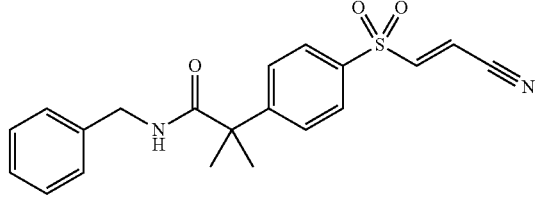 [SMILES: CC(C)(C(=O)NCc1ccccc1)c1ccc(S(=O)(=O)/C=C/C#N)cc1] | *** | * | * | ** |
| 7 | 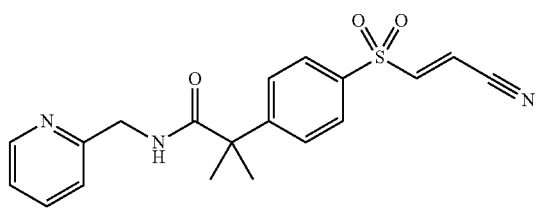 [SMILES: CC(C)(C(=O)NCc1ccccn1)c1ccc(S(=O)(=O)/C=C/C#N)cc1] | ** | * |  |  |
| 8 | 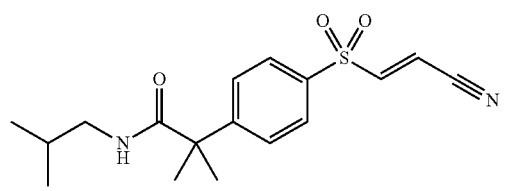 [SMILES: CC(C)CNC(=O)C(C)(C)c1ccc(S(=O)(=O)/C=C/C#N)cc1] | * |  | * | * |
| 9 | 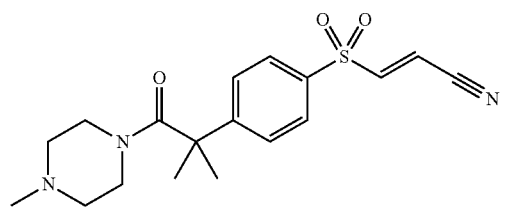 [SMILES: CN1CCN(C(=O)C(C)(C)c2ccc(S(=O)(=O)/C=C/C#N)cc2)CC1] | * | * | * | * |

TABLE I-continued
| No. | Compound | SU86 10 μM | HT29 10 μM | BxPC3 10 μM | A2780 10 μM |
|---|---|---|---|---|---|
| 10 | 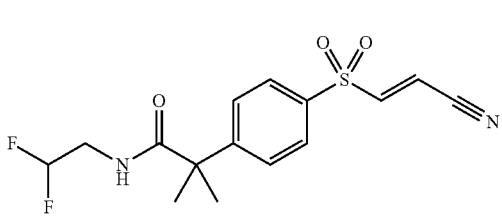 [SMILES: CC(C)(C(=O)NCC(F)F)c1ccc(S(=O)(=O)/C=C/C#N)cc1] | ** | * |  | * |
| 11 | 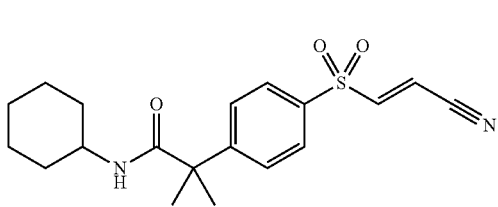 | ** | * |  |  |
| 12 | 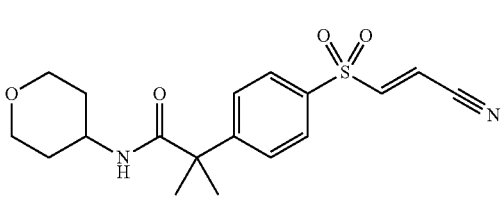 [SMILES: CC(C)(C(=O)NC1CCOCC1)c1ccc(S(=O)(=O)/C=C/C#N)cc1] | *** | * | * | * |
| 13 | 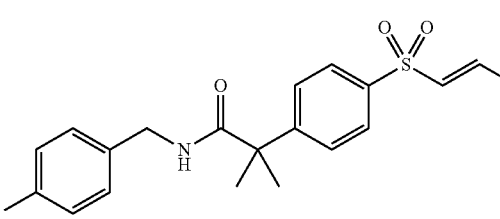 | * | ** | * | * |
| 14 | 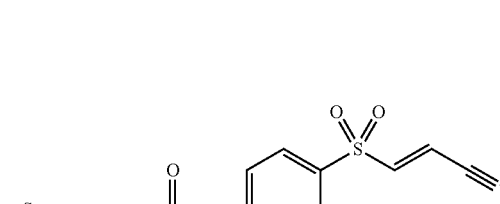 | * |  | * | ** |
| 15 | 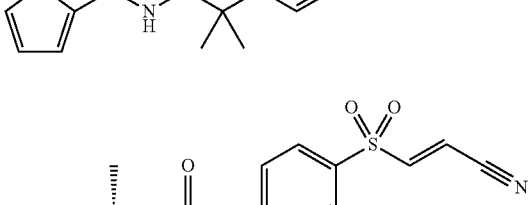 | *** | * | * | ** |
| 16 |  | * | | * | **** |

TABLE I-continued

| No. | Compound | SU86 10 μM | HT29 10 μM | BxPC3 10 μM | A2780 10 μM |
|-----|----------|------------|------------|-------------|-------------|
| 17 | | *** | | *** | **** |
| 18 | | *** | | *** | **** |
| 19 | | ** | | ** | ** |
| 20 | | *** | | **** | **** |
| 21 | | *** | | *** | *** |
| 22 | | *** | | **** | **** |
| 23 | | *** | | *** | **** |

TABLE I-continued

| No. | Compound | SU86 10 μM | HT29 10 μM | BxPC3 10 μM | A2780 10 μM |
|---|---|---|---|---|---|
| 24 | | *** | | *** | **** |
| 25 | | *** | | *** | **** |
| 26 | | * | * | * | |
| 27 | | * | ** | * | |
| 28 | | ** | **** | *** | |
| 29 | | * | *** | * | |
| 30 | | * | *** | * | |

TABLE I-continued

| No. | Compound | SU86 10 μM | HT29 10 μM | BxPC3 10 μM | A2780 10 μM |
|---|---|---|---|---|---|
| 31 | | ** | *** | *** | |
| 32 | | ** | *** | ** | |
| 33 | | * | *** | ** | |
| 34 | | | | | * |
| 35 | | | | | *** |
| 36 | | | | | *** |
| 37 | | | | | *** |
| 38 | | | | | ** |

TABLE I-continued

| No. | Compound | SU86 10 μM | HT29 10 μM | BxPC3 10 μM | A2780 10 μM |
|---|---|---|---|---|---|
| 39 | | | | | ** |
| 40 | | *** | **** | **** | |
| 41 | | *** | **** | **** | |
| 42 | | *** | **** | *** | |
| 43 | | * | * | * | |
| 44 | | *** | **** | **** | |
| 45 | | *** | **** | **** | |

TABLE I-continued

| No. | Compound | SU86 10 μM | HT29 10 μM | BxPC3 10 μM | A2780 10 μM |
|---|---|---|---|---|---|
| 46 | | *** | **** | **** | |
| 47 | | ** | | *** | *** |
| 48 | | * | | * | ** |
| 49 | | * | | * | * |
| 50 | | *** | **** | **** | |
| 51 | | *** | **** | **** | |
| 52 | | ** | *** | * | |
| 53 | | *** | **** | **** | |

TABLE I-continued

| No. | Compound | SU86 10 μM | HT29 10 μM | BxPC3 10 μM | A2780 10 μM |
| --- | --- | --- | --- | --- | --- |
| 54 | (3-tert-butylphenyl sulfonyl acrylonitrile) | **** | * | **** | **** |
| 55 | (4-tert-butylphenyl sulfonyl acrylamide) | ** | ** | *** | ** |
| 56 | (4-tert-butylphenyl sulfonyl propene) | * | * | * | * |
| 57 | (4-tert-butylphenyl sulfonyl styrene) | * | * | * | * |
| 58 | (4-tert-butylphenyl sulfonyl α-phenyl vinyl) | ** | ** | *** | * |
| 59 | (4-tert-butylphenyl sulfonyl acrylate ethyl ester) | ** | ** | *** | *** |
| 60 | (4-tert-butylphenyl thio acrylonitrile) | * | * | * | * |
| 61 | (2-tert-butyl-4-sulfonyl acrylonitrile phenoxyacetic acid) | * | * | ** | * |

TABLE I-continued

| No. | Compound | SU86 10 μM | HT29 10 μM | BxPC3 10 μM | A2780 10 μM |
|---|---|---|---|---|---|
| 62 | | ** | * | * | ** |
| 63 | | *** | **** | **** | **** |
| 64 | | *** | **** | **** | **** |
| 65 | | *** | **** | *** | **** |
| 66 | | *** | **** | *** | **** |
| 67 | | | | *** | **** |
| 68 | | | | *** | **** |

TABLE I-continued

| No. | Compound | SU86 10 μM | HT29 10 μM | BxPC3 10 μM | A2780 10 μM |
|---|---|---|---|---|---|
| 69 | | ** | *** | ** | *** |
| 70 | | *** | **** | *** | **** |
| 71 | | *** | **** | **** | **** |
| 72 | | *** | **** | *** | **** |
| 73 | | ** | **** | *** | *** |
| 74 | | | | * | * |
| 75 | | | | **** | *** |

TABLE I-continued

| No. | Compound | SU86 10 μM | HT29 10 μM | BxPC3 10 μM | A2780 10 μM |
|---|---|---|---|---|---|
| 76 | | | | *** | **** |
| 77 | | | | *** | **** |
| 78 | | *** | **** | *** | **** |
| 79 | | | | **** | **** |
| 80 | | ** | **** | *** | *** |
| 81 | | | | *** | **** |
| 82 | | | | * | * |

TABLE I-continued

| No. | Compound | SU86 10 μM | HT29 10 μM | BxPC3 10 μM | A2780 10 μM |
|---|---|---|---|---|---|
| 83 | | | | ** | * |
| 84 | | | | ** | ** |
| 85 | | | | *** | *** |
| 86 | | ** | **** | *** | ** |

\* = <10% relative reduction in Luciferase activity
\*\* = 10-50% relative reduction in Luciferase activity
\*\*\* = 50-85% relative reduction in Luciferase activity
\*\*\*\* = >85% relative reduction in Luciferase activity Experimental Section All reagents and solvents were obtained from commercial sources and used as received. $^1$H-NMR spectra were obtained on a Bruker Avance at 400 MHz in the solvent indicated with tetramethylsilane as an internal standard. Analytical HPLC was run using a Zorbax Eclipse XDB-C8 3.5 μm 4.6×75 mm column eluting with a mixture of acetonitrile and water containing 0.1% trifluoroacetic acid with a 5 minute gradient of 10-100%. LCMS results were obtained on either of two instruments. A Waters Aquity Ultra Performance LC with a Waters Aquity UPLC BEH C18 1.7 μm 2.1×50 mm column was paired with a Micromass-ZQ 2000 quadrupole mass spectrometer with electrospray ionization. Alternatively, an Agilent 1100 series HPLC with a Zorbax Eclipse XDB-C8-3.5 μm 2.1×30 mm column was paired with a Bruker Esquire 3000 mass spectrometer with electrospray ionization. Preparative HPLC was performed on a Gilson HPLC using a Phenomenex Gemini NX 5 μm C18, 21.2×100 mm column with UV detection or a Waters HPLC using a Waters XBridge PrepC8 5 μm OBD 30×75 mm column with MS detection on a Micromass-ZQ 2000 quadrupole mass spectrometer with electrospray ionization. Automated column chromatography was performed on a CombiFlash Companion (Teledyne Isco Inc.). Melting points were taken on a Mel-Temp apparatus and are uncorrected.

Example 1

2-[4-((E)-2-Cyano-ethenesulfonyl)-phenyl]-2-methyl-propionic acid

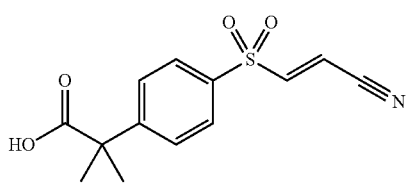 [SMILES: CC(C)(C(=O)O)c1ccc(S(=O)(=O)/C=C/C#N)cc1]

To a solution of 2-(4-bromophenyl)-2-methylpropanoic acid (2.43 g, 10 mmol) in anhydrous THF (150 ml) under nitrogen at −80° C. (ether/dry ice), was added slowly phenyl lithium in toluene (1.8 M, 11 mmol). After 5 min, to this mixture, n-BuLi (2.5 M in hexane, 11 mmol) was added. A cloudy suspension was slowly formed. Twenty minutes after BuLi addition, a stream of $SO_2$ was bubbled through the mixture for 15 min. The reaction mixture was then allowed to warm up to room temperature and the solvent was removed in vacuo. The sulfinate residue was dissolved in water (15 ml), acetic acid (8 ml), and MeOH (20 ml), followed by addition of 2-chloroacrylonitrile (18 mmol). The resulting mixture was stirred at room temperature overnight. The organic solvents were removed in vacuo and the residue was diluted with 20 ml of water. The solution was adjusted to pH5-6 with sat. $K_2HPO_4$ aq. solution then extracted with dichloromethane (2×100 ml) and dried over $MgSO_4$. After filtration, the filtrate was stirred with triethylamine (20 mmol) for 1 h. The solution was washed with 10% aq citric acid and brine, and then dried over $MgSO_4$. The final product was purified by flash column chromatography (silica gel, dichloromethane/EtOAc, gradient) to give 2-[4-((E)-2-Cyano-ethenesulfonyl)-phenyl]-2-methyl-propionic acid (1.2 g, 43%) as a white solid. 1H-NMR (DMSO-d6, 400 MHz) δ 12.65 (s, 1H), 8.23 (d, 1H, J=15.6 Hz), 7.88 (m, 2H), 7.68 (m, 2H), 6.91 (d, 1H, J=15.6 Hz), 1.51 (s, 6H); $^{13}$C-NMR: (DMSO-$d_6$, 100 MHz) δ 176.7, 152.4, 149.1, 135.6, 128.2, 127.5, 114.6, 112.0, 46.4, 26.1.

Example 2

2-[3-((E)-2-Cyano-ethenesulfonyl)-phenyl]-2-methyl-propionic acid

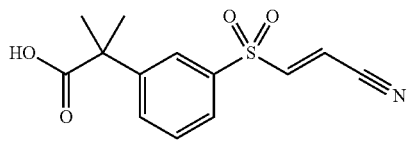 [SMILES: CC(C)(C(=O)O)c1cccc(S(=O)(=O)/C=C/C#N)c1]

To a solution of 2-(3-bromophenyl)-2-methylpropanoic acid (7.3 g, 30 mmol) in anhydrous THF (300 ml) under $N_2$ at −80° C. (ether/dry ice), was added slowly phenyl lithium in toluene (1.8 M, 33 mmol). After 5 min, to this mixture, n-BuLi (2.5 M in hexane, 33 mmol) was added. A cloudy suspension was slowly formed. Twenty minutes after BuLi addition, a stream of $SO_2$ was bubbled through the mixture for about 15 min. The reaction mixture was then allowed to warm up to room temperature and the solvent was removed in vacuo. The sulfinate residue was dissolved in water (50 ml), acetic acid (25 ml), and MeOH (50 ml), followed by addition of 2-chloroacrylonitrile (60 mmol). The resulting mixture was stirred at room temperature overnight. The organic solvents were removed in vacuo and the residue was diluted with 50 ml of water. The solution was adjusted to pH~5-6 with sat. $K_2HPO_4$ aq. solution, then extracted with dichloromethane (2×100 mL) and dried over $MgSO_4$. After filtration, the filtrate was stirred with triethylamine (20 mmol) for 1 h. The solution was washed with 10% aq. citric acid and brine, dried over $MgSO_4$. The final product was purified by flash column chromatography (silica gel, dichloromethane/EtOAc, gradient) to give 2-[3-((E)-2-Cyano-ethenesulfonyl)-phenyl]-2-methyl-propionic acid (4.1 g, 49%) as a white solid. 1H-NMR (DMSO-d6, 400 MHz) δ 12.65 (s, 1H), 8.30 (d, 1H, J=15.6 Hz), 7.82 (m, 2H), 7.80 (m, 1H), 7.69 (m, 1H), 6.94 (d, 1H, J=15.6 Hz), 1.53 (s, 6H); $^{13}$C-NMR: (DMSO-d6, 100 MHz) δ 176.8, 149.0, 147.2, 137.6, 132.7, 130.1, 126.4, 124.8, 114.6, 112.3, 46.1, 26.1.

Example 3

(E)-3-[4-(1,1-Dimethyl-2-morpholin-4-yl-2-oxo-ethyl)-benzenesulfonyl]-acrylonitrile

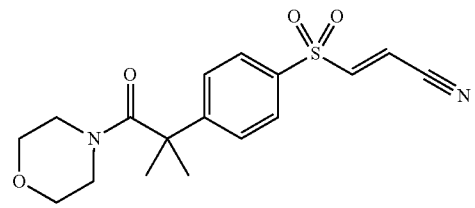 [SMILES: CC(C)(C(=O)N1CCOCC1)c1ccc(S(=O)(=O)/C=C/C#N)cc1]

2-[4-((E)-2-Cyano-ethenesulfonyl)-phenyl]-2-methyl-propionic acid (50.0 mg, 0.179 mmol), morpholine (0.0156 mL, 0.179 mmol), N-(3-dimethylaminopropyl)-N'-ethylcarbodiimide hydrochloride (34.3 mg, 0.179 mmol) and 1-hydroxybenzotriazole (12.1 mg, 0.0895 mmol) were dissolved in tetrahydrofuran (5.0 mL) and the reaction mixture was allowed to stir overnight at room temperature. The reaction mixture was poured over saturated sodium bicarbonate and organics were extracted with dichloromethane/ethyl acetate. Combined extracts were then dried over sodium sulfate, filtered and concentrated. The crude reaction mixture was purified via Gilson reverse phase chromatography. Combined fractions were lyophilized to afford (E)-3-[4-(1,1-Dimethyl-2-morpholin-4-yl-2-oxo-ethyl)-benzenesulfonyl]-acrylonitrile (11 mg, 17%). MS: 349 (M+H); 1H-NMR (DMSO-d6 400 MHz) δ 8.24 (d, 1H, J=15.7 Hz), 7.91 (d, 2H, J=7.7 Hz), 7.55 (d, 2H, J=7.7 Hz), 6.90 (d, 1H, J=15.7 Hz), 3.57 (br s, 8H), 1.47 (s, 6H).

Example 4

2-[4-((E)-2-Cyano-ethenesulfonyl)-phenyl]-N-(2-hydroxy-ethyl)-isobutyramide

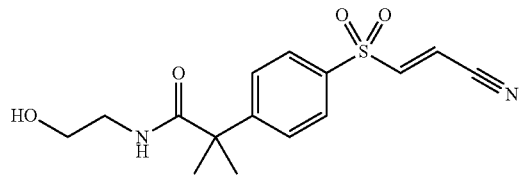 [SMILES: CC(C)(C(=O)NCCO)c1ccc(S(=O)(=O)/C=C/C#N)cc1]

2-[4-((E)-2-Cyano-ethenesulfonyl)-phenyl]-2-methyl-propionic acid (75.0 mg, 0.268 mmol), ethanolamine (0.0162 mL, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in tetrahydrofuran (7.5 mL) and the reaction mixture was allowed to stir overnight at room temperature. The reaction mixture was poured over saturated sodium bicarbonate and organics were extracted with dichloromethane/ethyl acetate. Combined extracts were then dried over sodium sulfate, filtered and concentrated. The crude reaction mixture was purified via Gilson reverse phase chromatography. Combined fractions were lyophilized to afford 2-[4-((E)-2-Cyano-ethenesulfonyl)-phenyl]-N-(2-hydroxyethyl)-isobutyramide as a white foam (10 mg, 12%). MS: 323 (M+H); 1H-NMR (DMSO-d6, 400 MHz) δ 8.23 (d, 1H, J=15.7 Hz), 7.85 (d, 2H, J=7.4 Hz), 7.62 (d, 2H, J=7.4 Hz), 7.45 (m, 1H), 6.90 (d, 1H, J=15.7 Hz), 4.39 (t, 1H, J=5.3 Hz), 3.40 (m, 2H), 3.11 (m, 2H), 1.47 (s, 6H).

Example 5

2-[4-((E)-2-Cyano-ethenesulfonyl)-phenyl]-N-phenyl-isobutyramide

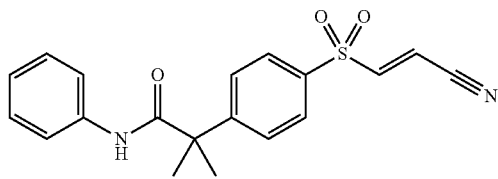 [SMILES: CC(C)(C(=O)Nc1ccccc1)c1ccc(S(=O)(=O)/C=C/C#N)cc1]

2-[4-((E)-2-Cyano-ethenesulfonyl)-phenyl]-2-methyl-propionic acid (300.0 mg, 1.074 mmol), aniline (0.0979 mL, 1.07 mmol), N-(3-dimethylaminopropyl)-N'-ethylcarbodiimide hydrochloride (206 mg, 1.07 mmol) and 1-hydroxybenzotriazole (72.6 mg, 0.537 mmol) were dissolved in tetrahydrofuran (30 mL) and the reaction mixture was allowed to stir overnight at room temperature. The reaction mixture was poured over saturated sodium bicarbonate and organics were extracted with dichloromethane/ethyl acetate. Combined extracts were then dried over sodium sulfate, filtered and concentrated. The crude reaction mixture was purified by flash column (hexanes/ethyl acetate) to afford 2-[4-((E)-2-Cyano-ethenesulfonyl)-phenyl]-N-phenyl-isobutyramide as a foam (171 mg, 45%). MS: 355 (M+H); 1H-NMR (DMSO-d6, 400 MHz) δ 9.22 (s, 1H), 8.23 (d, 1H, J=15.7 Hz), 7.90 (d, 2H, J=7.8 Hz), 7.68 (d, 2H, J=7.8 Hz), 7.57 (d, 2H, J=7.7 Hz), 7.27 (m, 2H), 7.05 (m, 1H), 6.90 (d, 1H, J=15.7 Hz), 1.60 (s, 6H); $^{13}$C-NMR: (DMSO-$d_6$, 100 MHz) δ 173.7, 153.2, 149.2, 139.0, 135.5, 128.4, 128.2, 127.6, 123.5, 120.4, 114.6, 112.0, 47.9, 26.5.

Example 6

N-Benzyl-2-[4-((E)-2-cyano-ethenesulfonyl)-phenyl]-isobutyramide

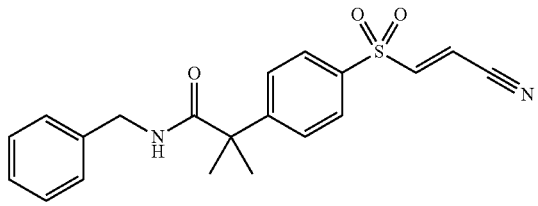 [SMILES: CC(C)(C(=O)NCc1ccccc1)c1ccc(S(=O)(=O)/C=C/C#N)cc1]

2-[4-((E)-2-Cyano-ethenesulfonyl)-phenyl]-2-methyl-propionic acid (300.0 mg, 1.074 mmol), benzylamine (0.115 g, 1.07 mmol), N-(3-dimethylaminopropyl)-N'-ethylcarbodiimide hydrochloride (206 mg, 1.07 mmol) and 1-hydroxybenzotriazole (72.6 mg, 0.537 mmol) were dissolved in tetrahydrofuran (30 mL) and the reaction mixture was allowed to stir overnight at room temperature. The reaction mixture was poured over saturated sodium bicarbonate and organics were extracted with dichloromethane/ethyl acetate. Combined extracts were then dried over sodium sulfate, filtered and concentrated. The crude reaction mixture was purified via Isco flash column (hexanes/ethyl acetate) to afford N-Benzyl-2-[4-((E)-2-cyano-ethenesulfonyl)-phenyl]-isobutyramide as a white powder (173 mg, 44%). MS: 369 (M+H); 1H-NMR (DMSO-d6, 400 MHz) δ 8.24 (d, 1H, J=15.6 Hz), 8.06 (t, 1H, J=5.6 Hz), 7.86 (d, 2H, J=7.6 Hz), 7.63 (d, 2H, J=7.6 Hz), 7.27 (m, 2H), 7.21 (m, 1H), 7.11 (d, 2H, J=7.3 Hz), 6.90 (d, 1H, J=15.6 Hz), 4.24 (d, 2H, J=5.6 Hz), 1.52 (s, 6H); $^{13}$C-NMR: (DMSO-$d_6$, 100 MHz) δ 174.6, 153.4, 149.2, 139.6, 135.3, 128.0, 127.9, 127.6, 126.7, 126.5, 114.5, 111.9, 46.6, 42.3, 26.3.

Example 7

2-[4-((E)-2-Cyano-ethenesulfonyl)-phenyl]-N-pyridin-2-ylmethyl-isobutyramide

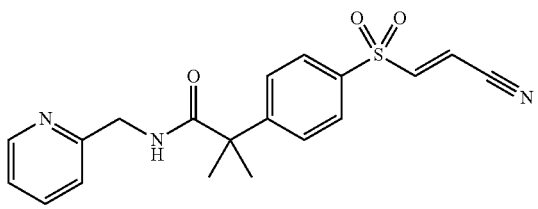 [SMILES: CC(C)(C(=O)NCc1ccccn1)c1ccc(S(=O)(=O)/C=C/C#N)cc1]

2-[4-((E)-2-Cyano-ethenesulfonyl)-phenyl]-2-methyl-propionic acid (75.0 mg, 0.268 mmol), pyridin-2-yl-methylamine (0.0290 g, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in tetrahydrofuran (7.5 mL, 92 mmol) and the reaction mixture was allowed to stir overnight at room temperature. The reaction mixture was poured over saturated sodium bicarbonate and organics were extracted with dichloromethane/ethyl acetate. Combined extracts were then dried over sodium sulfate, filtered and concentrated. The crude reaction mixture was purified via Gilson reverse phase chromatography. Combined fractions were lyophilized to afford 2-[4-((E)-2-Cyano-ethenesulfonyl)-phenyl]-N-pyridin-2-ylmethyl-isobutyramide as a TFA salt (24 mg, 24%). MS: 370 (M+H); 1H-NMR (DMSO-d6, 400 MHz) δ 8.63 (d, 1H, J=4.8 Hz), 8.26 (m, 2H), 8.06 (t, 1H, J=5.4 Hz), 7.89 (d, 2H, J=8.1 Hz), 7.67 (d, 2H, J=8.1 Hz), 7.54 (m, 1H), 7.35 (d, 1H, J=7.8 Hz), 6.92 (d, 1H, J=15.6 Hz), 4.43 (d, 2H, J=5.4 Hz), 1.57 (s, 6H).

Example 8

2-[4-((E)-2-Cyano-ethenesulfonyl)-phenyl]-N-isobutyl-isobutyramide

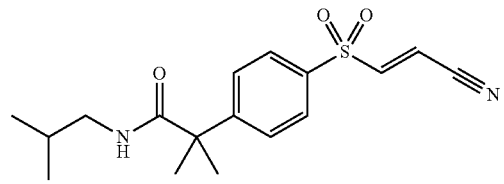 [SMILES: CC(C)CNC(=O)C(C)(C)c1ccc(S(=O)(=O)/C=C/C#N)cc1]

2-[4-((E)-2-Cyano-ethenesulfonyl)-phenyl]-2-methyl-propionic acid (75.0 mg, 0.268 mmol), isobutylamine (0.0255 mL, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in tetrahydrofuran (7.5 mL) and the reaction mixture was allowed to stir overnight at room temperature. The reaction mixture was poured over saturated sodium bicarbonate and organics were extracted with dichloromethane/ethyl acetate. Combined extracts were then dried over sodium sulfate, filtered and concentrated. The crude reaction mixture was purified via Gilson reverse phase chromatography. Combined fractions were lyophilized to afford 2-[4-((E)-2-Cyano-ethenesulfonyl)-phenyl]-N-isobutyl-isobutyramide (18 mg, 20%). MS: 335 (M+H); 1H-NMR (DMSO-d6, 400 MHz) δ 8.23 (d, 1H, J=15.9 Hz), 7.86 (d, 2H, J=7.6 Hz), 7.61 (d, 2H, J=7.6 Hz), 7.45 (m, 1H), 6.90 (d, 1H, J=15.9 Hz), 2.84 (m, 2H), 1.67 (m, 1H), 1.48 (s, 6H), 0.74 (d, 6H, J=6.6 Hz).

Example 9

(E)-3-{4-[1,1-Dimethyl-2-(4-methyl-piperazin-1-yl)-2-oxo-ethyl]-benzenesulfonyl}-acrylonitrile

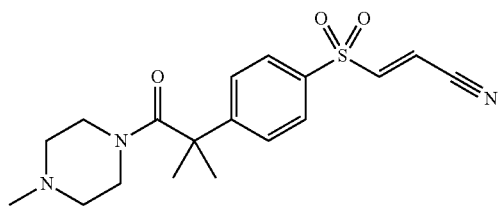 [SMILES: CN1CCN(C(=O)C(C)(C)c2ccc(S(=O)(=O)/C=C/C#N)cc2)CC1]

2-[4-((E)-2-Cyano-ethenesulfonyl)-phenyl]-2-methyl-propionic acid (75.0 mg, 0.268 mmol), 1-methylpiperazine (0.0298 mL, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in tetrahydrofuran (7.5 mL) and the reaction mixture was allowed to stir overnight at room temperature. The reaction mixture was poured over saturated sodium bicarbonate and organics were extracted with dichloromethane/ethyl acetate. Combined extracts were then dried over sodium sulfate, filtered and concentrated. The crude reaction mixture was purified via Gilson reverse phase chromatography. Combined fractions were lyophilized to afford (E)-3-{4-[1,1-Dimethyl-2-(4-methyl-piperazin-1-yl)-2-oxo-ethyl]-benzenesulfonyl}-acrylonitrile as a TFA salt (17 mg, 17%). MS: 362 (M+H); 1H-NMR (DMSO-d6, 400 MHz) δ 9.67 (br s, 1H), 8.25 (d, 1H, J=15.8 Hz), 7.92 (d, 2H, J=7.9 Hz), 7.56 (d, 2H, J=7.9 Hz), 6.91 (d, 1H, J=15.8 Hz), 3.53 (br s, 4H), 3.27 (br s, 2H), 2.84 (br s, 2H), 2.73 (s, 3H), 1.50 (s, 6H).

Example 10

2-[4-(E)-2-Cyano-ethenesulfonyl)-phenyl]-N-cyclopropylmethyl-isobutyramide

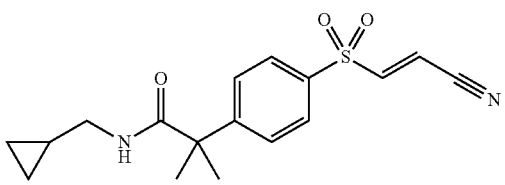 [SMILES: CC(C)(C(=O)NCC1CC1)c1ccc(S(=O)(=O)/C=C/C#N)cc1]

2-[4-((E)-2-Cyano-ethenesulfonyl)-phenyl]-2-methyl-propionic acid (100.0 mg, 0.3580 mmol), cyclopropylmethylamine (0.0307 mL, 0.358 mmol), N-(3-dimethylaminopropyl)-N'-ethylcarbodiimide hydrochloride (68.6 mg, 0.358 mmol) and 1-hydroxybenzotriazole (24.2 mg, 0.179 mmol) were dissolved in tetrahydrofuran (10 mL) and the reaction mixture was allowed to stir overnight at room temperature. The reaction mixture was poured over saturated sodium bicarbonate and organics were extracted with dichloromethane/ethyl acetate. Combined extracts were then dried over sodium sulfate, filtered and concentrated. The crude reaction mixture was purified via Gilson reverse phase chromatography. Combined fractions were lyophilized to afford 2-[4-((E)-2-Cyano-ethenesulfonyl)-phenyl]-N-cyclopropylmethyl-isobutyramide as a foam (45 mg, 38%). MS: 333 (M+H); 1H-NMR (CDCl3, 400 MHz) δ 7.87 (d, 2H, J=7.8 Hz), 7.63 (d, 2H, J=7.8 Hz), 7.21 (d, 1H, J=15.8 Hz), 6.55 (d, 1H, J=15.8 Hz), 5.36 (br s, 1H), 3.10 (m, 2H), 1.61 (s, 6H), 0.87 (m, 1H), 0.47 (m, 2H), 0.15 (m, 2H).

Example 11

2-[4-((E)-2-Cyano-ethenesulfonyl)-phenyl]-N-(2,2-difluoro-ethyl)-isobutyramide

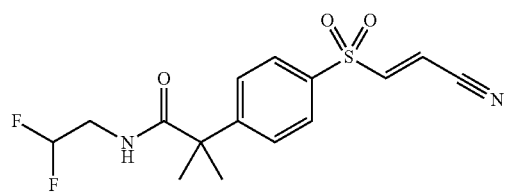 [SMILES: CC(C)(C(=O)NCC(F)F)c1ccc(S(=O)(=O)/C=C/C#N)cc1]

2-[4-((E)-2-Cyano-ethenesulfonyl)-phenyl]-2-methyl-propionic acid (100.0 mg, 0.3580 mmol), 2,2-difluoro-ethylamine (0.0290 g, 0.358 mmol), N-(3-dimethylaminopropyl)-N'-ethylcarbodiimide hydrochloride (68.6 mg, 0.358 mmol) and 1-hydroxybenzotriazole (24.2 mg, 0.179 mmol) were dissolved in tetrahydrofuran (10 mL) and the reaction mixture was allowed to stir overnight at room temperature. The reaction mixture was poured over saturated sodium bicarbonate and organics were extracted with dichloromethane/ethyl acetate. Combined extracts were then dried over sodium sulfate, filtered and concentrated. The crude reaction mixture was purified via Gilson reverse phase chromatography. Combined fractions were lyophilized to afford 2-[4-((E)-2-Cyano-ethenesulfonyl)-phenyl]-N-(2,2-difluoro-ethyl)-isobutyramide as a white foam (40 mg, 32%). 1H-NMR (CDCl3, 400 MHz) δ 7.89 (d, 2H, J=7.6 Hz), 7.60 (d, 2H, J=7.6 Hz), 7.23 (d, 1H, J=15.7 Hz), 6.57 (d, 1H, J=15.7 Hz), 5.84 (tt, 1H, J=4.0, 56 Hz), 5.46 (m, 1H), 3.61 (m, 2H), 1.62 (s, 6H).

Example 12

2-[4-((E)-2-Cyano-ethenesulfonyl)-phenyl]-N-cyclohexyl-isobutyramide

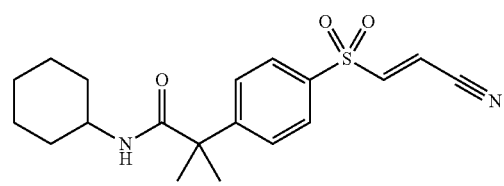 [SMILES: CC(C)(C(=O)NC1CCCCC1)c1ccc(S(=O)(=O)/C=C/C#N)cc1]

2-[4-((E)-2-Cyano-ethenesulfonyl)-phenyl]-2-methyl-propionic acid (100 mg, 0.358 mmol), cyclohexanamine (35.5 mg, 0.358 mmol), N-(3-dimethylaminopropyl)-N'-ethylcarbodiimide hydrochloride (68.6 mg, 0.358 mmol) and 1-hydroxybenzotriazole (24.2 mg, 0.179 mmol) were dissolved in tetrahydrofuran (10.0 mL) and the reaction mixture was allowed to stir overnight at room temperature. The reaction was concentrated under reduced pressure and the residue was taken up in 1.2 mL of acetonitrile. Purification by mass-directed HPLC using a gradient of 25-75% MeCN/water both containing 0.1% TFA as the eluting solvent to afford 2-[4-((E)-2-Cyano-ethenesulfonyl)-phenyl]-N-cyclohexylisobutyramide (79 mg, 61%), mp=191-193° C. MS: 361 (M+H); 1H-NMR (CDCl3, 400 MHz) δ 7.86 (d, 2H, J=8.1 Hz), 7.60 (d, 2H, J=8.1 Hz), 7.21 (d, 1H, J=15.6 Hz), 6.55 (d, 1H, J=15.6 Hz), 5.05 (m, 1H), 3.76 (m, 1H), 1.83 (m, 2H), 1.64 (m, 3H), 1.62 (s, 6H), 1.34 (m, 2H), 1.13 (m, 1H), 1.00 (m, 2H).

Example 13

2-[4-((E)-2-Cyano-ethenesulfonyl)-phenyl]-N-(tetrahydro-pyran-4-yl)-isobutyramide

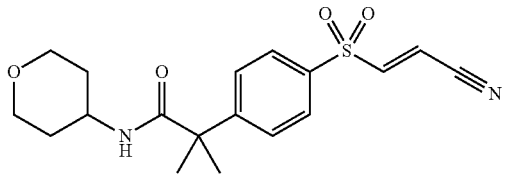 [SMILES: CC(C)(C(=O)NC1CCOCC1)c1ccc(S(=O)(=O)/C=C/C#N)cc1]

2-[4-((E)-2-Cyano-ethenesulfonyl)-phenyl]-2-methyl-propionic acid (100.0 mg, 0.3580 mmol), tetrahydro-pyran-4-ylamine (0.0362 g, 0.358 mmol), N-(3-dimethylaminopropyl)-N'-ethylcarbodiimide hydrochloride (68.6 mg, 0.358 mmol) and 1-hydroxybenzotriazole (24.2 mg, 0.179 mmol) were dissolved in tetrahydrofuran (10 mL) and the reaction mixture was allowed to stir overnight at room temperature. The reaction mixture was poured over saturated sodium bicarbonate and organics were extracted with dichloromethane/ethyl acetate. Combined extracts were then dried over sodium sulfate, filtered and concentrated. The crude reaction mixture was purified via Gilson reverse phase chromatography. Combined fractions were lyophilized to afford 2-[4-((E)-2-Cyano-ethenesulfonyl)-phenyl]-N-(tetrahydro-pyran-4-yl)-isobutyramide as a white powder (45 mg, 35%). MS: 363 (M+H); 1H-NMR (CDCl3, 400 MHz) δ 7.87 (d, 2H, J=7.6 Hz), 7.60 (d, 2H, J=7.6 Hz), 7.21 (d, 1H, J=15.6 Hz), 6.56 (d, 1H, J=15.6 Hz), 5.08 (m, 1H), 3.98 (m, 1H), 3.90 (m, 2H), 3.44 (m, 2H), 1.83 (m, 2H), 1.59 (s, 6H), 1.34 (m, 2H).

Example 14

N-(4-Chloro-benzyl)-2-[4-((E)-2-cyano-ethenesulfonyl)-phenyl]-isobutyramide

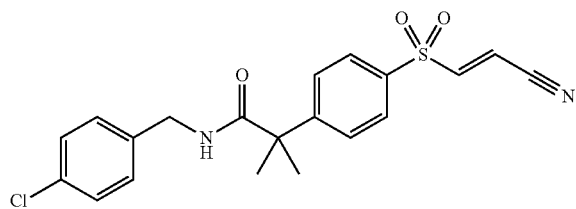 [SMILES: CC(C)(C(=O)NCc1ccc(Cl)cc1)c1ccc(S(=O)(=O)/C=C/C#N)cc1]

2-[4-((E)-2-Cyano-ethenesulfonyl)-phenyl]-2-methyl-propionic acid (100.0 mg, 0.3580 mmol), p-chlorobenzylamine (0.0507 g, 0.358 mmol), N-(3-dimethylaminopropyl)-N'-ethylcarbodiimide hydrochloride (68.6 mg, 0.358 mmol) and 1-hydroxybenzotriazole (24.2 mg, 0.179 mmol) were dissolved in tetrahydrofuran (10 mL) and the reaction mixture was allowed to stir overnight at room temperature. The reaction mixture was poured over saturated sodium bicarbonate and organics were extracted with dichloromethane/ethyl acetate. Combined extracts were then dried over sodium sulfate, filtered and concentrated. The crude reaction mixture was purified via Gilson reverse phase chromatography. Combined fractions were lyophilized to afford N-(4-Chloro-benzyl)-2-[4-((E)-2-cyano-ethenesulfonyl)-phenyl]-isobutyramide as a white powder (69 mg, 48%). 1H-NMR (CDCl3, 400 MHz) δ 7.86 (d, 2H, J=7.4 Hz), 7.60 (d, 2H, J=7.4 Hz), 7.27 (d, 2H, J=7.4 Hz), 7.20 (d, 1H, J=15.6 Hz), 7.11 (d, 2H, J=7.4 Hz), 6.55 (d, 1H, J=15.6 Hz), 5.53 (br s, 1H), 4.37 (d, 2H, J=5.6 Hz), 1.62 (s, 6H).

Example 15

2-[4-((E)-2-Cyano-ethenesulfonyl)-phenyl]-N-thiophen-2-ylmethyl-isobutyramide

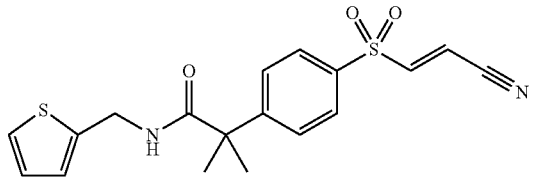 [SMILES: CC(C)(C(=O)NCc1cccs1)c1ccc(S(=O)(=O)/C=C/C#N)cc1]

2-[4-((E)-2-Cyano-ethenesulfonyl)-phenyl]-2-methyl-propionic acid (100.0 mg, 0.3580 mmol), thiophene-2-methanamine (0.0405 g, 0.358 mmol), N-(3-dimethylaminopropyl)-N'-ethylcarbodiimide hydrochloride (68.6 mg, 0.358 mmol) and 1-hydroxybenzotriazole (24.2 mg, 0.179 mmol) were dissolved in tetrahydrofuran (10 mL) and the reaction mixture was allowed to stir overnight at room temperature. The reaction mixture was poured over saturated sodium bicarbonate and organics were extracted with dichloromethane/ethyl acetate. Combined extracts were then dried over sodium sulfate, filtered and concentrated. The crude reaction mixture was purified via Gilson reverse phase chromatography. Combined fractions were lyophilized to afford 2-[4-((E)-2-Cyano-ethenesulfonyl)-phenyl]-N-thiophen-2-ylmethyl-isobutyramide as a white powder (67 mg, 50%). MS: 375 (M+H); 1H-NMR (CDCl3, 400 MHz) δ 7.85 (d, 2H, J=7.4 Hz), 7.60 (d, 2H, J=7.4 Hz), 7.20 (m, 2H), 6.90 (m, 2H), 6.54 (d, 1H, J=15.4 Hz), 5.55 (br s, 1H), 4.59 (d, 2H, J=5.4 Hz), 1.62 (s, 6H).

Example 16

2-[4-((E)-2-Cyano-ethenesulfonyl)-phenyl]-N—((S)-1-phenyl-ethyl)-isobutyramide

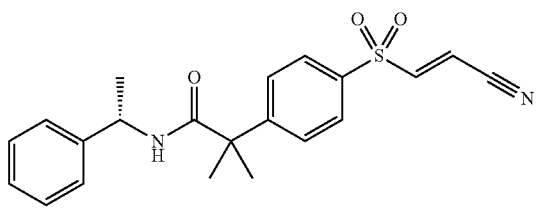 [SMILES: C[C@H](NC(=O)C(C)(C)c1ccc(S(=O)(=O)/C=C/C#N)cc1)c1ccccc1]

2-[4-((E)-2-Cyano-ethenesulfonyl)-phenyl]-2-methyl-propionic acid (75.0 mg, 0.268 mmol), (S)-1-phenyl-ethyl-amine (34.3 uL, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in methylene chloride (7.50 mL) and the reaction mixture was allowed to stir overnight at room temperature. The reaction was concentrated under reduced pressure and the residue was taken up in 1.3 mL of acetonitrile. Purification by mass-directed HPLC using a gradient of 25-75% MeCN/water both containing 0.1% TFA as the eluting solvent afforded 2-[4-((E)-2-Cyano-ethenesulfonyl)-phenyl]-N—((S)-1-phenyl-ethyl)-isobutyramide as an amorphous white solid (66 mg, 64%). MS: 383 (M+H); 1H-NMR (CDCl3, 400 MHz) δ 7.84 (d, 2H, J=7.6 Hz), 7.55 (d, 2H, J=7.6 Hz), 7.37-7.25 (m, 3H), 7.24-7.14 (m, 3H), 6.53 (d, 1H, J=15.7 Hz), 5.59 (d, 1H, J=7.1 Hz), 5.16-5.06 (m, 1H), 1.61 (s, 3H), 1.60 (s, 3H), 1.43 (d, 3H, J=6.8 Hz).

Example 17

2-[4-((E)-2-Cyano-ethenesulfonyl)-phenyl]-N—((R)-1-phenyl-ethyl)-isobutyramide

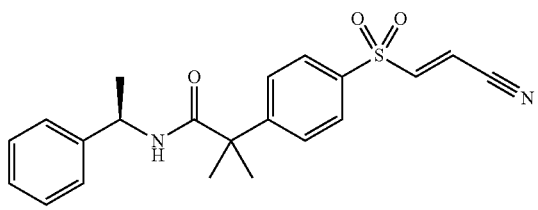 [SMILES: C[C@@H](NC(=O)C(C)(C)c1ccc(S(=O)(=O)/C=C/C#N)cc1)c1ccccc1]

2-[4-((E)-2-Cyano-ethenesulfonyl)-phenyl]-2-methyl-propionic acid (75.0 mg, 0.268 mmol), (R)-1-phenyl-ethyl-amine (34.2 uL, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in methylene chloride (7.50 mL) and the reaction mixture was allowed to stir overnight at room temperature. The reaction was concentrated under reduced pressure and the residue was taken up in 1.3 mL of acetonitrile. Purification by mass-directed HPLC using a gradient of 25-75% MeCN/water both containing 0.1% TFA as the eluting solvent afforded 2-[4-((E)-2-Cyano-ethenesulfonyl)-phenyl]-N—((R)-1-phenyl-ethyl)-isobutyramide as an amorphous white solid (69 mg, 67%). MS: 383 (M+H); 1H-NMR (CDCl3, 400 MHz) δ 7.84 (d, 2H, J=7.3 Hz), 7.54 (d, 2H, J=7.3 Hz), 7.37-7.26 (m, 3H), 7.23-7.15 (m, 3H), 6.54 (d, 1H, J=15.6 Hz), 5.68 (d, 1H, J=6.8 Hz), 5.16-5.06 (m, 1H), 1.62 (s, 3H), 1.60 (s, 3H), 1.44 (d, 3H, J=6.8 Hz).

Example 18

2-[4-((E)-2-Cyano-ethenesulfonyl)-phenyl]-N-(4-fluoro-benzyl)-isobutyramide

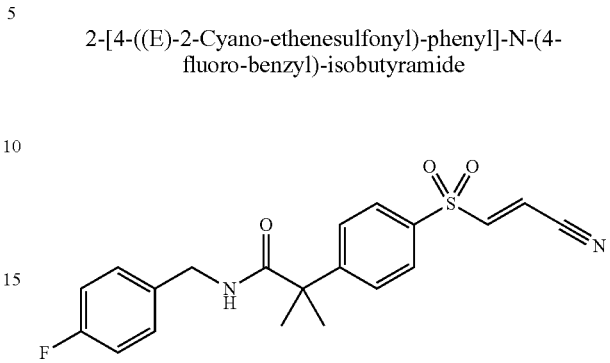

2-[4-((E)-2-Cyano-ethenesulfonyl)-phenyl]-2-methyl-propionic acid (75.0 mg, 0.268 mmol), 4-fluoro-benzylamine (30.5 uL, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in methylene chloride (7.50 mL) and the reaction mixture was allowed to stir overnight at room temperature. The reaction was concentrated under reduced pressure and the residue was taken up in 1.2 mL of acetonitrile. Purification by mass-directed HPLC using a gradient of 25-75% MeCN/water both containing 0.1% TFA as the eluting solvent afforded 2-[4-((E)-2-Cyano-ethenesulfonyl)-phenyl]-N-(4-fluoro-benzyl)-isobutyramide as a white foam (34 mg, 34%). MS: 387 (M+H); 1H-NMR (CDCl3, 400 MHz) δ 7.85 (d, 2H, J=7.4 Hz), 7.59 (d, 2H, J=7.4 Hz), 7.30-7.24 (m, 1H), 7.20-7.10 (m, 2H), 7.04-6.95 (m, 2H), 6.55 (d, 1H, J=15.6 Hz), 5.63-5.50 (m, 1H), 4.37 (d, 2H, J=5.6 Hz), 1.63 (s, 6H).

Example 19

2-[4-((E)-2-Cyano-ethenesulfonyl)-phenyl]-N-prop-2-ynyl-isobutyramide

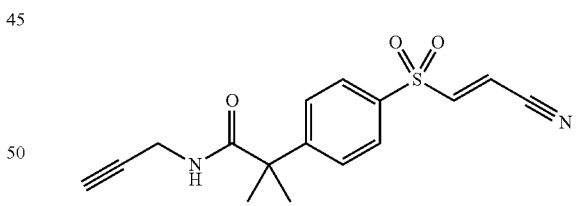

2-[4-((E)-2-Cyano-ethenesulfonyl)-phenyl]-2-methyl-propionic acid (145 mg, 0.519 mmol), prop-2-ynylamine (50.0 uL, 0.729 mmol), N-(3-dimethylaminopropyl)-N'-ethylcarbodiimide hydrochloride (139 mg, 0.727 mmol) and 1-hydroxybenzotriazole (37 mg, 0.28 mmol) were combined in methylene chloride (3.00 mL). After 1 h, the mixture was conc. to dryness. The residue was taken up in DMSO and purified (mass-directed HPLC, 15-55% MeCN:H2O, TFA modifier) to afford 2-[4-((E)-2-Cyano-ethenesulfonyl)-phenyl]-N-prop-2-ynyl-isobutyramide as an off-white foam (66 mg, 40%). MS: 317 (M+H); 1H-NMR (CDCl3, 400 MHz) δ 7.88 (d, 2H, J=8.1 Hz), 7.61 (d, 2H, J=8.1 Hz), 7.23 (d, 1H, J=15.7 Hz), 6.56 (d, 1H, J=15.7 Hz), 5.40 (s, 1H), 4.03 (m, 2H), 2.21 (s, 1H), 1.62 (s, 6H).

Example 20

(E)-3-{4-[2-(3,4-Dihydro-1H-isoquinolin-2-yl)-1,1-dimethyl-2-oxo-ethyl]-benzenesulfonyl}-acrylonitrile

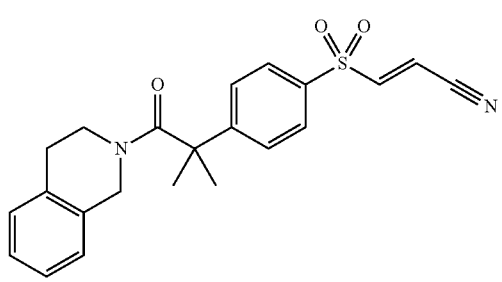 [SMILES: CC(C)(C(=O)N1CCc2ccccc2C1)c1ccc(S(=O)(=O)/C=C/C#N)cc1]

2-[4-((E)-2-Cyano-ethenesulfonyl)-phenyl]-2-methyl-propionic acid (75.0 mg, 0.268 mmol), 1,2,3,4-tetrahydroisoquinoline (35.8 mg, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in methylene chloride (7.50 mL) and the reaction mixture was allowed to stir overnight at room temperature. The reaction was concentrated under reduced pressure and the residue was taken up in 1.2 mL of acetonitrile. Purification by mass-directed HPLC using a gradient of 25-75% MeCN/water both containing 0.1% TFA as the eluting solvent to afford (E)-3-{4-[2-(3,4-Dihydro-1H-isoquinolin-2-yl)-1,1-dimethyl-2-oxo-ethyl]-benzenesulfonyl}-acrylonitrile as a white solid (23 mg, 22%), mp=54-60° C. MS: 395 (M+H); 1H-NMR (CDCl3, 400 MHz) δ 8.00-7.60 (m, 2H), 7.60-7.33 (m, 2H), 7.25-6.87 (m, 5H), 6.65-6.41 (m, 1H), 4.93-4.62 (m, 1H), 4.22-3.72 (m, 2H), 3.31-3.03 (m, 1H), 3.00-2.78 (m, 1H), 2.52-2.23 (m, 1H), 1.62 (s, 6H).

Example 21

2-[4-((E)-2-Cyano-ethenesulfonyl)-phenyl]-N-(4-pyrazol-1-yl-benzyl)-isobutyramide

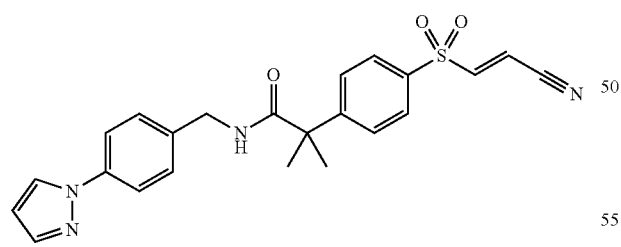

2-[4-((E)-2-Cyano-ethenesulfonyl)-phenyl]-2-methyl-propionic acid (75.0 mg, 0.268 mmol), 4-Pyrazol-1-yl-benzylamine (46.5 mg, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in methylene chloride (7.50 mL) and the reaction mixture was allowed to stir overnight at room temperature. The reaction was concentrated under reduced pressure and the residue was taken up in 1.2 mL of acetonitrile. Purification by mass-directed HPLC using a gradient of 25-75% MeCN/water both containing 0.1% TFA as the eluting solvent to afford 2-[4-((E)-2-Cyano-ethenesulfonyl)-phenyl]-N-(4-pyrazol-1-yl-benzyl)-isobutyramide trifluoroacetic acid salt as a pale-yellow solid (33 mg, 28%), mp=47-53° C. MS: 435 (M+H); 1H-NMR (CDCl3, 400 MHz) δ 7.92-7.83 (m, 3H), 7.80-7.76 (m, 1H), 7.64-7.57 (m, 4H), 7.30-7.25 (m, 2H), 7.21 (d, 1H, J=15.6 Hz), 6.55 (d, 1H, J=15.6 Hz), 6.52-6.47 (m, 1H), 5.73-5.63 (m, 1H), 4.44 (d, 2H, J=5.7 Hz), 1.64 (s, 6H).

Example 22

N-Benzyl-2-[4-((E)-2-cyano-ethenesulfonyl)-phenyl]-N-methyl-isobutyramide

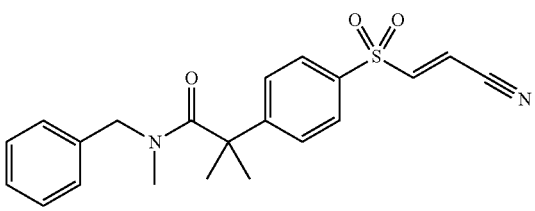 [SMILES: CN(Cc1ccccc1)C(=O)C(C)(C)c1ccc(S(=O)(=O)/C=C/C#N)cc1]

2-[4-((E)-2-Cyano-ethenesulfonyl)-phenyl]-2-methyl-propionic acid (75.0 mg, 0.268 mmol), N-methyl-benzenemethanamine, (34.6 uL, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in methylene chloride (7.50 mL) and the reaction mixture was allowed to stir overnight at room temperature. The reaction was concentrated under reduced pressure and the residue was taken up in 1.2 mL of acetonitrile. Purification by mass-directed HPLC using a gradient of 25-75% MeCN/water both containing 0.1% TFA as the eluting solvent to afford N-Benzyl-2-[4-((E)-2-cyano-ethenesulfonyl)-phenyl]-N-methyl-isobutyramide as a white foam (33 mg, 32%). MS: 383 (M+H); 1H-NMR (CDCl3, 400 MHz, mixture of rotamers) δ 7.92-7.76 (m, 2H), 7.49 (d, 2H, J=8.0 Hz), 7.40-7.01 (m, 6H), 6.55 (d, 1H, J=14.7 Hz), 4.72-3.94 (m, 2H), 3.02-2.31 (m, 3H), 1.63 (s, 6H).

Example 23

2-[4-((E)-2-Cyano-ethenesulfonyl)-phenyl]-N-(4-methoxy-phenyl)-isobutyramide

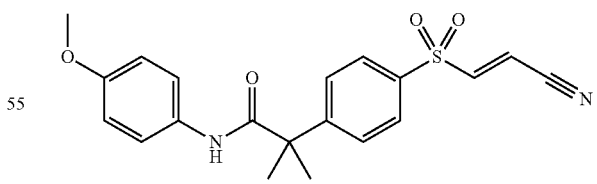

2-[4-((E)-2-Cyano-ethenesulfonyl)-phenyl]-2-methyl-propionic acid (75.0 mg, 0.268 mmol), 4-methoxybenzenamine (33.1 mg, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in methylene chloride (7.50 mL) and the reaction mixture was allowed to stir overnight at room temperature. The reaction was concentrated under reduced pressure and the residue was taken up in 1.2 mL of acetonitrile. Purification by mass-directed HPLC using a gradient of 25-75% MeCN/water both containing 0.1% TFA as the eluting solvent to afford 2-[4-((E)-2-Cyano-ethenesulfonyl)-phenyl]-N-(4-methoxy-phenyl)-isobutyramide as a white solid (53 mg, 52%), mp=123-126° C. MS: 385 (M+H); 1H-NMR (CDCl3, 400 MHz) δ 7.90 (d, 2H, J=8.2 Hz), 7.69 (d, 2H, J=8.2 Hz), 7.28 (d, 2H, J=8.6 Hz), 7.21 (d, 1H, J=15.7 Hz), 6.83 (d, 2H, J=8.6 Hz), 6.77 (bs, 1H), 6.57 (d, 1H, J=15.7 Hz), 3.78 (s, 3H), 1.71 (s, 6H).

Example 24

2-[4-((E)-2-Cyano-ethenesulfonyl)-phenyl]-N-phenethyl-isobutyramide

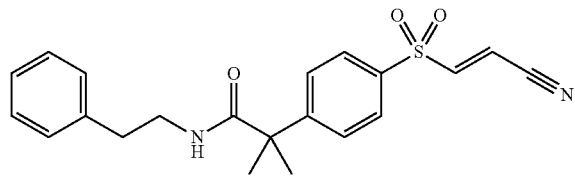 [SMILES: CC(C)(C(=O)NCCc1ccccc1)c1ccc(S(=O)(=O)/C=C/C#N)cc1]

2-[4-((E)-2-Cyano-ethenesulfonyl)-phenyl]-2-methyl-propionic acid (75.0 mg, 0.268 mmol), phenylethylamine (33.7 uL, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in methylene chloride (7.50 mL) and the reaction mixture was allowed to stir overnight at room temperature. The reaction was concentrated under reduced pressure and the residue was taken up in 1.2 mL of acetonitrile. Purification by mass-directed HPLC using a gradient of 25-75% MeCN/water both containing 0.1% TFA as the eluting solvent to afford 2-[4-((E)-2-Cyano-ethenesulfonyl)-phenyl]-N-phenethylisobutyramide as a white foam (39 mg, 38%). MS: 383 (M+H); 1H-NMR (CDCl3, 400 MHz) δ 7.79 (d, 2H, J=8.6 Hz), 7.49 (d, 2H, J=8.6 Hz), 7.29-7.21 (m, 3H), 7.19 (d, 1H, J=15.7 Hz), 7.07-7.02 (m, 2H), 6.55 (d, 1H, J=15.7 Hz), 5.20-5.08 (m, 1H), 3.53-3.46 (m, 2H), 2.76 (t, 2H, J=6.7 Hz), 1.54 (s, 6H).

Example 25

2-[4-((E)-2-Cyano-ethenesulfonyl)-phenyl]-N-(3-methoxy-phenyl)-isobutyramide

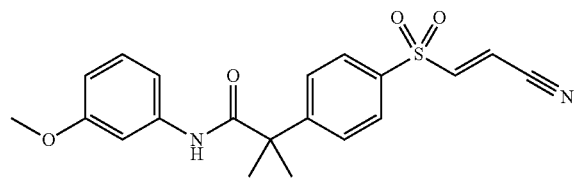 [SMILES: COc1cccc(NC(=O)C(C)(C)c2ccc(S(=O)(=O)/C=C/C#N)cc2)c1]

2-[4-((E)-2-Cyano-ethenesulfonyl)-phenyl]-2-methyl-propionic acid (150.0 mg, 0.5370 mmol), 3-methoxyaniline (80.3 uL, 0.715 mmol), N-(3-dimethylaminopropyl)-N'-ethylcarbodiimide hydrochloride (143 mg, 0.745 mmol) and 1-hydroxybenzotriazole (36.1 mg, 0.267 mmol) were dissolved in acetonitrile (2.50 mL) and the reaction mixture was allowed to stir at room temperature overnight. The reaction was diluted with 0.4 mL DMSO, filtered and purified. Purification by mass-directed HPLC using a gradient of 25-75% MeCN/water both containing 0.1% TFA as the eluting solvent to afford 2-[4-((E)-2-Cyano-ethenesulfonyl)-phenyl]-N-(3-methoxy-phenyl)-isobutyramide (108 mg, 52.3%) as a white foam. MS: 385 (M+H); 1H-NMR (CDCl3, 400 MHz) δ 7.91 (d, 2H, J=8.5 Hz), 7.68 (d, 2H, J=8.5 Hz), 7.25-7.16 (m, 3H), 6.86-6.78 (m, 2H), 6.67 (dd, 1H, J=1.9, 8.3 Hz), 6.57 (d, 1H, J=15.7 Hz), 3.79 (s, 3H), 1.71 (s, 6H).

Example 26

2-[4-((E)-2-Cyano-ethenesulfonyl)-phenyl]-N-(4-sulfamoyl-benzyl)-isobutyramide

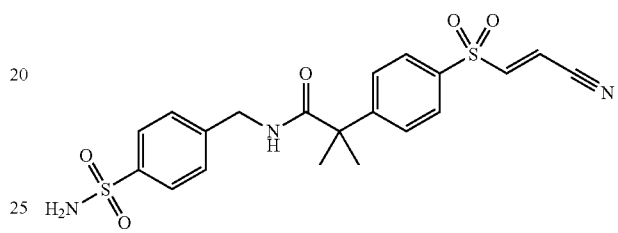

4-Aminomethyl-benzenesulfonamide hydrochloride (59.8 mg, 0.268 mmol) was placed in methylene chloride (10.00 mL) and macroporous carbonate resin (3.16 mmol/g loading, 255 mg, 0.806 mmol) was added. The reaction was stirred at room temperature for 30 minutes and then filtered to remove the resin. The solution was added to a vial containing 2-[4-((E)-2-Cyano-ethenesulfonyl)-phenyl]-2-methyl-propionic acid (75.0 mg, 0.268 mmol), 1-hydroxybenzotriazole (18.1 mg, 0.134 mmol), and N-(3-dimethylaminopropyl)-N'-ethylcarbodiimide hydrochloride (51.5 mg, 0.268 mmol). The reaction was stirred at 40° C. overnight and then concentrated under reduced pressure. The residue was taken up in 1.6 mL of DMSO and purified by prep-HPLC using a gradient of 10-45% MeCN/water both containing 0.1% TFA as the eluting solvent to afford 2-[4-((E)-2-Cyano-ethenesulfonyl)-phenyl]-N-(4-sulfamoyl-benzyl)-isobutyramide as a white foam (17 mg, 14%). MS: 448 (M+H); 1H-NMR (DMSO-d6, 400 MHz) δ 8.24 (d, 1H, J=15.6 Hz), 8.16 (t, 1H, J=5.8 Hz), 7.88 (d, 2H, J=8.4 Hz), 7.73 (d, 2H, J=8.1 Hz), 7.64 (d, 2H, J=8.4 Hz), 7.35-7.26 (m, 4H), 6.91 (d, 1H, J=15.6 Hz), 4.28 (d, 2H, J=5.8 Hz), 1.52 (s, 6H).

Example 27

2-[4-((E)-2-Cyano-ethenesulfonyl)-phenyl]-N-(4-methanesulfonyl-benzyl)-isobutyramide

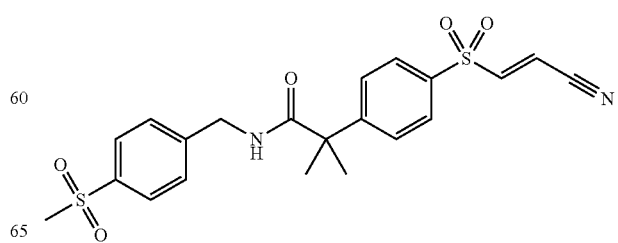

4-Methanesulfonyl-benzylamine hydrochloride (59.5 mg, 0.268 mmol) was placed in methylene chloride (10.00 mL) and macroporous carbonate resin (3.16 mmol/g loading, 255 mg, 0.806 mmol) was added. The reaction was stirred at room temperature for 30 minutes and then filtered to remove the macroporous carbonate resin. The solution was added to a vial containing 2-[4-((E)-2-Cyano-ethenesulfonyl)-phenyl]-2-methyl-propionic acid (75.0 mg, 0.268 mmol), 1-hydroxybenzotriazole (18.1 mg, 0.134 mmol), and N-(3-dimethylaminopropyl)-N'-ethylcarbodiimide hydrochloride (51.5 mg, 0.268 mmol). The reaction was stirred at 40° C. overnight and was then concentrated under reduced pressure. The residue was taken up in 1.6 mL of DMSO and purified by prep-HPLC using a gradient of 10-45% MeCN/water both containing 0.1% TFA as the eluting solvent to afford 2-[4-((E)-2-Cyano-ethenesulfonyl)-phenyl]-N-(4-methanesulfonyl-benzyl)-isobutyramide as a white foam (33 mg, 28%). MS: 447 (M+H); 1H-NMR (CDCl3, 400 MHz) δ 7.87 (d, 2H, J=8.4 Hz), 7.80 (d, 2H, J=8.2 Hz), 7.62 (d, 2H, J=8.4 Hz), 7.32 (d, 2H, J=8.2 Hz), 7.22 (d, 1H, J=15.6 Hz), 6.57 (d, 1H, J=15.6 Hz), 5.99 (t, 1H, J=5.6 Hz), 4.49 (d, 2H, J=6.0 Hz), 3.03 (s, 3H), 1.66 (s, 6H).

Example 28

(E)-3-[4-(1,1-Dimethyl-2-oxo-2-piperidin-1-yl-ethyl)-benzenesulfonyl]-acrylonitrile

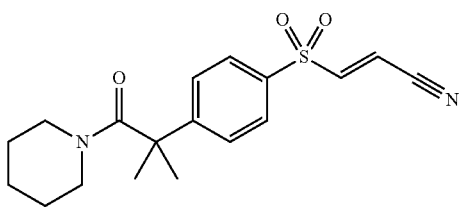 [SMILES: CC(C)(C(=O)N1CCCCC1)c1ccc(S(=O)(=O)/C=C/C#N)cc1]

2-[4-((E)-2-Cyano-ethenesulfonyl)-phenyl]-2-methyl-propionic acid (75.0 mg, 0.268 mmol), piperidine (26.6 uL, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in methylene chloride (7.50 mL) and the reaction mixture was allowed to stir overnight at room temperature. The reaction was concentrated under reduced pressure and the residue was taken up in 1.6 mL of DMSO. Purification by mass-directed HPLC using a gradient of 25-75% MeCN/water both containing 0.1% TFA as the eluting solvent to afford (E)-3-[4-(1,1-Dimethyl-2-oxo-2-piperidin-1-yl-ethyl)-benzenesulfonyl]-acrylonitrile as a yellow oil (25 mg, 27%). MS: 347 (M+H); 1H-NMR (CDCl3, 400 MHz) δ 7.88 (d, 2H, J=8.4 Hz), 7.49 (d, 2H, J=8.4 Hz), 7.22 (d, 1H, J=15.6 Hz), 6.56 (d, 1H, J=15.6 Hz), 3.26-2.64 (m, 3H), 1.93-1.68 (m, 1H), 1.57 (s, 6H), 1.56-1.44 (m, 4H), 1.25-0.95 (m, 2H); 13C-NMR: (DMSO-d6, 100 MHz, 95° C.) δ 172.3, 153.9, 149.6, 135.7, 128.6, 126.4, 114.3, 111.5, 47.1, 45.1, 28.1, 24.9, 23.7.

Example 29

2-[4-((E)-2-Cyano-ethenesulfonyl)-phenyl]-N—((S)-2-hydroxy-1-phenyl-ethyl)-isobutyramide

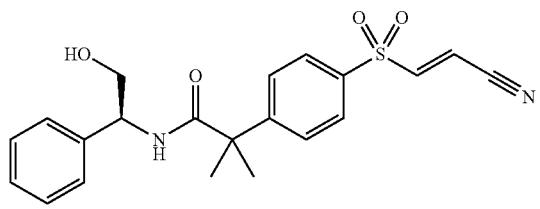 [SMILES: CC(C)(C(=O)N[C@H](CO)c1ccccc1)c1ccc(S(=O)(=O)/C=C/C#N)cc1]

N-(3-dimethylaminopropyl)-N'-ethylcarbodiimide hydrochloride (116 mg, 0.602 mmol) was added to 2-[4-((E)-2-Cyano-ethenesulfonyl)-phenyl]-2-methyl-propionic acid (153 mg, 0.548 mmol), (S)-2-amino-2-phenyl-ethanol (86.0 mg, 0.627 mmol) and 1-hydroxybenzotriazole (6.8 mg, 0.050 mmol) in methylene chloride (6.0 mL) and stirred for 1 h. The mixture was conc. in vacuo, dissolved in DMSO and purified (mass-directed HPLC, 15-55% MeCN/water, TFA modifier). Concentration of the product fractions afforded 2-[4-((E)-2-Cyano-ethenesulfonyl)-phenyl]-N—((S)-2-hydroxy-1-phenyl-ethyl)-isobutyramide (143 mg, 65.5%) as a white foam. MS: 399 (M+H); 1H-NMR (DMSO-d6, 400 MHz) δ 8.25 (d, 1H, J=15.6 Hz), 7.83 (d, 2H, J=8.4 Hz), 7.69 (d, 1H, J=8.0 Hz), 7.61 (d, 2H, J=8.4 Hz), 7.25 (m, 2H), 7.17 (m, 3H), 6.91 (d, 1H, J=15.6 Hz), 4.87 (m, 1H), 3.53 (d, 2H, J=6.7 Hz), 1.51 (s, 6H).

Example 30

2-[4-((E)-2-Cyano-ethenesulfonyl)-phenyl]-N—((S)-2-oxo-azepan-3-yl)-isobutyramide

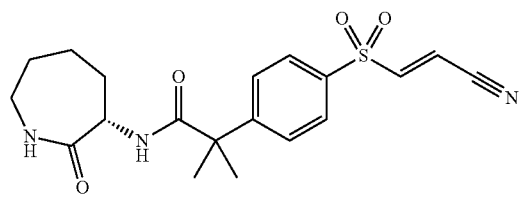 [SMILES: CC(C)(C(=O)N[C@H]1CCCCNC1=O)c1ccc(S(=O)(=O)/C=C/C#N)cc1]

(S)-3-Amino-azepan-2-one hydrochloride (44.2 mg, 0.268 mmol) was placed in methylene chloride (10.00 mL) and macroporous carbonate resin (3.16 mmol/g loading, 255 mg, 0.806 mmol) was added. The reaction was stirred at room temperature for 30 minutes and then filtered to remove the resin. The solution was added to a vial containing 2-[4-((E)-2-Cyano-ethenesulfonyl)-phenyl]-2-methyl-propionic acid (75.0 mg, 0.268 mmol), 1-hydroxybenzotriazole (18.1 mg, 0.134 mmol), and N-(3-dimethylaminopropyl)-N'-ethylcarbodiimide hydrochloride (51.5 mg, 0.268 mmol). The reaction was stirred at 40° C. overnight and was then concentrated under reduced pressure. The residue was taken up in 1.6 mL of DMSO and purified by prep-HPLC using a gradient of 10-45% MeCN/water both containing 0.1% TFA as the eluting solvent to afford 2-[4-((E)-2-Cyano-ethenesulfonyl)-phenyl]-N—((S)-2-oxo-azepan-3-yl)-isobutyramide (60 mg, 57%) as a white foam. MS: 390 (M+H); HNMR (DMSO-d6, 400 MHz) δ 8.23 (d, 1H, J=15.6 Hz), 7.90-7.84 (m, 1H), 7.86 (d, 2H, J=8.5 Hz), 7.69 (d, 2H, J=6.5 Hz), 7.23 (d, 1H, J=6.2 Hz), 6.90 (d, 1H, J=15.6 Hz), 4.41-4.30 (m, 1H), 3.23-3.10 (m, 1H), 3.10-2.97 (m, 1H), 1.93-1.82 (m, 1H), 1.82-1.69 (m, 2H), 1.69-1.55 (m, 1H), 1.51 (s, 6H), 1.41-1.26 (m, 1H), 1.25-1.10 (m, 1H).

Example 31

2-[4-((E)-2-Cyano-ethenesulfonyl)-phenyl]-N-[4-(2-methoxy-ethoxymethyl)-phenyl]-isobutyramide

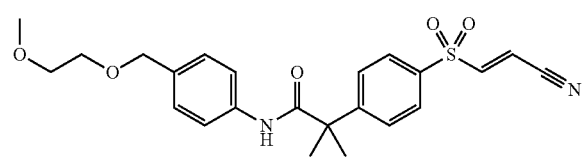 [SMILES: COCCOCc1ccc(NC(=O)C(C)(C)c2ccc(S(=O)(=O)/C=C/C#N)cc2)cc1]

a) Potassium hydroxide (0.682 g, 10.3 mmol) was added to a suspension of p-nitrobenzylbromide (2.048 g, 9.480 mmol) in 2-methoxyethanol (20.0 mL, 254 mmol) and the mixture was heated in a vial at 105° C. After 90 min, the mixture was cooled to room temperature. The mixture was poured into EtOAc (100 mL) and washed with water (3×10 mL), brine (20 mL) and dried over sodium sulfate. Concentration in vacuo after filtration gave an oil, which was purified on ISCO (25 g preload w/DCM, 80 g column, 5-40% EtOAc:Hex). Pure fractions were combined and conc. to afford 1-(2-Methoxy-ethoxymethyl)-4-nitro-benzene (1.245 g, 62.18%) as an orange oil.

b) 1-(2-Methoxy-ethoxymethyl)-4-nitro-benzene (200 mg, 0.947 mmol was dissolved in methanol (9.5 mL) and 5% Platinum on Carbon, Sulfided (0.5%) (36.9 mg, 0.00947 mmol) was added. The reaction was hydrogenated at 50 psi for 60 minutes and then filtered through celite to remove the catalyst. The filtrate was then concentrated under reduced pressure to afford 4-(2-Methoxy-ethoxymethyl)-phenylamine as a yellow oil.

c) 2-[4-((E)-2-Cyano-ethenesulfonyl)-phenyl]-2-methyl-propionic acid (75.0 mg, 0.268 mmol), 4-(2-Methoxy-ethoxymethyl)-phenylamine (48.7 mg, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in methylene chloride (7.50 mL) and the reaction mixture was allowed to stir overnight at room temperature. The reaction was concentrated under reduced pressure and the residue was taken up in 1.6 mL of DMSO. Purification by mass-directed HPLC using a gradient of 25-75% MeCN/water both containing 0.1% TFA as the eluting solvent to afford 2-[4-((E)-2-Cyano-ethenesulfonyl)-phenyl]-N-[4-(2-methoxy-ethoxymethyl)-phenyl]-isobutyramide as an orange oil (57 mg, 48%). MS: 465 (M+Na); HNMR (DMSO-d6, 400 MHz) δ 9.23 (s, 1H), 8.23 (d, 1H, J=15.7 Hz), 7.89 (d, 2H, J=8.6 Hz), 7.67 (d, 2H, J=8.6 Hz), 7.54 (d, 2H, J=8.6 Hz), 7.22 (d, 2H, J=8.6 Hz), 6.0 (d, 1H, J=15.7 Hz), 4.40 (s, 2H), 3.53-3.43 (m, 4H), 3.24 (s, 3H), 1.60 (s, 6H).

Example 32

(2-{2-[4-((E)-2-Cyano-ethenesulfonyl)-phenyl]-2-methyl-propionylamino}-ethyl)-carbamic acid tert-butyl ester 2-[4-((E)-2-Cyano-ethenesulfonyl)-phenyl]-2-methyl-propionic acid (1.00E2 mg, 0.358 mmol), N-(2-aminoethyl)(tert-butoxy)carboxamide (62.3 uL, 0.394 mmol), and N,N-diisopropylethylamine (168 uL, 0.967 mmol) were placed in methylene chloride (3.00 mL) and bromotris(pyrrolydino)phosphonium hexafluorophosphate (184 mg, 0.394 mmol) was added. The reaction was stirred at room temperature for 45 minutes and then concentrated under reduced pressure. The residue was taken up in DMSO and purified by prep-HPLC using a gradient of 25-75% MeCN/water both containing 0.1% TFA as the eluting solvent to afford (2-{2-[4-((E)-2-Cyano-ethenesulfonyl)-phenyl]-2-methyl-propionylamino}-ethyl)-carbamic acid tert-butyl ester as a white foam (101 mg, 67%). MS: 444 (M+Na); HNMR (CDCl3, 400 MHz) δ 7.85 (d, 2H, J=8.6 Hz), 7.61 (d, 2H, J=8.6 Hz), 7.20 (d, 1H, J=15.6 Hz), 6.77-6.66 (m, 1H), 6.53 (d, 1H, J=15.6 Hz), 4.93-4.80 (m, 1H), 3.38-3.21 (m, 4H), 1.61 (s, 6H), 1.41 (s, 9H).

Example 33

(6-{2-[4-((E)-2-Cyano-ethenesulfonyl)-phenyl]-2-methyl-propionylamino}-hexyl)-carbamic acid tert-butyl ester N-tert-Butyloxycarbonyl-1,6-diaminohexane hydrochloride (90.5 mg, 0.358 mmol) was placed in 5.0 mL of DCM with 450 mg of macroporous carbonate resin (3 mmol/g) and stirred for 30 minutes and then filtered to remove the resin. 2-[4-((E)-2-Cyano-ethenesulfonyl)-phenyl]-2-methyl-propionic acid (100 mg, 0.358 mmol), 1-hydroxybenzotriazole (24.2 mg, 0.179 mmol), N-(3-dimethylaminopropyl)-N'-ethylcarbodiimide hydrochloride (68.6 mg, 0.358 mmol), and N,N-diisopropylethylamine (187 uL, 1.07 mmol) were placed in 5.0 mL of DCM and the solution of N-tert-butyloxycarbonyl-1,6-diaminohexane was added. The reaction was stirred at room temperature for 2 hours and then concentrated under reduced pressure. The residue was taken up in 1.5 mL of DMSO and purified by Prep-HPLC using a gradient of 25-75% MeCN/water both containing 0.1% TFA as the eluting solvent to afford (6-{2-[4-((E)-2-Cyano-ethenesulfonyl)-phenyl]-2-methyl-propionylamino}-hexyl)-carbamic acid tert-butyl ester as a white foam (119 mg, 70%). MS: 500 (M+H); HNMR (CDCl3, 400 MHz) δ 7.86 (d, 2H, J=8.5 Hz), 7.61 (d, 2H, J=8.5 Hz), 7.23 (d, 1H, J=15.7 Hz), 6.56 (d, 1H, J=15.7 Hz), 5.61-5.42 (m, 1H), 4.64-4.42 (m, 1H), 3.25-3.15 (m, 2H), 3.11-3.00 (m, 2H), 1.60 (s, 6H), 1.53-1.34 (m, 13H), 1.34-1.16 (m, 4H).

Example 34

{2-[2-(2-{2-[4-((E)-2-Cyano-ethenesulfonyl)-phenyl]-2-methyl-propionylamino}-ethoxy)-ethoxy]-ethyl}-carbamic acid tert-butyl ester

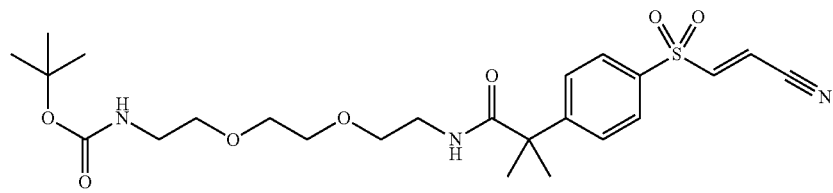 [SMILES: CC(C)(C)OC(=O)NCCOCCOCCNC(=O)C(C)(C)c1ccc(S(=O)(=O)/C=C/C#N)cc1]

2-[4-((E)-2-Cyano-ethenesulfonyl)-phenyl]-2-methyl-propionic acid (150 mg, 0.537 mmol), {2-[2-(2-amino-ethoxy)-ethoxy]-ethyl}-carbamic acid tert-butyl ester (147 mg, 0.591 mmol), N,N-diisopropylethylamine (252 uL, 1.45 mmol) were placed in methylene chloride (4.50 mL) and bromotris(pyrrolydino)phosphonium hexafluorophosphate (275 mg, 0.591 mmol) was added. The reaction was stirred at room temperature for 45 minutes and then concentrated under reduced pressure. The residue was taken up in DMSO and purified by prep-HPLC using a gradient of 25-75% MeCN/water both containing 0.1% TFA as the eluting solvent to afford {2-[2-(2-{2-[4-((E)-2-Cyano-ethenesulfonyl)-phenyl]-2-methyl-propionylamino}-ethoxy)-ethoxy]-ethyl}-carbamic acid tert-butyl ester as an oil (214 mg, 78%). MS: 532 (M+Na); HNMR (CDCl3, 400 MHz) δ 7.86 (d, 2H, J=8.4 Hz), 7.61 (d, 2H, J=8.4 Hz), 7.23 (d, 1H, J=15.7 Hz), 6.55 (d, 1H, J=15.7 Hz), 5.83-5.30 (m, 2H), 3.60-3.48 (m, 8H), 3.48-3.38 (m, 2H), 3.34-3.20 (m, 2H), 1.61 (s, 6H), 1.45 (s, 9H).

Example 35

2-[3-((E)-2-Cyano-ethenesulfonyl)-phenyl]-N-cyclohexyl-isobutyramide

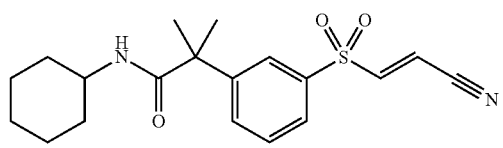 [SMILES: CC(C)(C(=O)NC1CCCCC1)c1cccc(S(=O)(=O)/C=C/C#N)c1]

2-[3-((E)-2-Cyano-ethenesulfonyl)-phenyl]-2-methyl-propionic acid (83.0 mg, 0.297 mmol), cyclohexanamine (45.2 uL, 0.396 mmol), N-(3-dimethylaminopropyl)-N'-ethylcarbodiimide hydrochloride (79.0 mg, 0.412 mmol) and 1-hydroxybenzotriazole (20.0 mg, 0.148 mmol) were dissolved in acetonitrile (1.50 mL) and the reaction mixture was allowed to stir 1 h at room temperature. The reaction was diluted with 0.4 mL DMSO, filtered and purified. Purification by mass-directed HPLC using a gradient of 25-75% MeCN/water both containing 0.1% TFA as the eluting solvent to afford 2-[3-((E)-2-Cyano-ethenesulfonyl)-phenyl]-N-cyclohexyl-isobutyramide (78 mg, 73%) as an off white foam. MS: 361 (M+H); 1H-NMR (DMSO-d6, 400 MHz) δ 8.25 (d, 1H, J=15.6 Hz), 7.78 (m, 1H), 7.74 (m, 2H), 7.67 (m, 1H), 7.20 (d, 1H, J=8.0 Hz), 6.90 (d, 1H, J=15.6 Hz), 3.55 (m, 1H), 1.64 (m, 4H), 1.55 (m, 1H), 1.47 (s, 6H), 1.0-1.3 (m, 5H).

Example 36

2-[3-((E)-2-Cyano-ethenesulfonyl)-phenyl]-N-(3-methoxy-phenyl)-isobutyramide

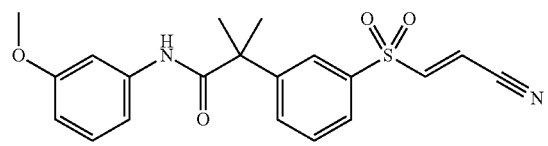 [SMILES: COc1cccc(NC(=O)C(C)(C)c2cccc(S(=O)(=O)/C=C/C#N)c2)c1]

2-[3-((E)-2-Cyano-ethenesulfonyl)-phenyl]-2-methyl-propionic acid (83.0 mg, 0.297 mmol), 3-methoxyaniline (44.4 uL, 0.396 mmol), N-(3-dimethylaminopropyl)-N'-ethylcarbodiimide hydrochloride (79.0 mg, 0.412 mmol) and 1-hydroxybenzotriazole (20.0 mg, 0.148 mmol) were dissolved in acetonitrile (1.50 mL) and the reaction mixture was allowed to stir 1 h at room temperature. The reaction was diluted with 0.4 mL DMSO, filtered and purified. Purification by mass-directed HPLC using a gradient of 25-75% MeCN/water both containing 0.1% TFA as the eluting solvent to afford 2-[3-((E)-2-Cyano-ethenesulfonyl)-phenyl]-N-(3-methoxy-phenyl)-isobutyramide (29 mg, 25%) as a light pink lyophilate. MS: 385 (M+H); 1H-NMR (DMSO-d6, 400 MHz) δ 9.19 (s, 1H), 8.28 (d, 1H, J=15.6 Hz), 7.85 (m, 1H), 7.82 (m, 1H), 7.77 (m, 1H), 7.70 (m, 1H), 7.25 (m, 1H), 7.16 (m, 2H), 6.91 (d, 1H, J=15.6 Hz), 6.62 (m, 1H), 3.70 (s, 3H), 1.61 (s, 6H).

Example 37

2-[3-((E)-2-Cyano-ethenesulfonyl)-phenyl]-N-(4-fluoro-benzyl)-isobutyramide

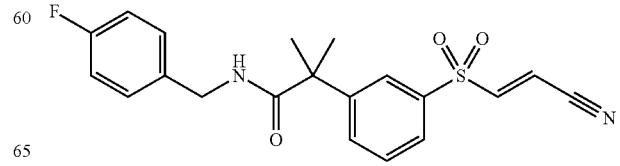

2-[3-((E)-2-Cyano-ethenesulfonyl)-phenyl]-2-methyl-propionic acid (83.0 mg, 0.297 mmol), 4-fluoro-benzylamine (45.0 uL, 0.396 mmol), N-(3-dimethylaminopropyl)-N'-ethylcarbodiimide hydrochloride (79.0 mg, 0.412 mmol) and 1-hydroxybenzotriazole (20.0 mg, 0.148 mmol) were dissolved in acetonitrile (1.50 mL) and the reaction mixture was allowed to stir 1 h at room temperature. The reaction was diluted with 0.4 mL DMSO, filtered and purified. Purification by mass-directed HPLC using a gradient of 25-75% MeCN/water both containing 0.1% TFA as the eluting solvent afforded 2-[3-((E)-2-Cyano-ethenesulfonyl)-phenyl]-N-(4-fluoro-benzyl)-isobutyramide (61 mg, 53%) as a beige lyophilate. MS: 387 (M+H); 1H-NMR (DMSO-d6, 400 MHz) δ 8.25 (d, 1H, J=15.6 Hz), 8.08 (m, 1H), 7.90 (m, 2H), 7.73 (m, 1H), 7.70 (m, 1H), 7.15 (m, 2H), 7.08 (m, 2H), 6.91 (d, 1H, J=15.6 Hz), 4.22 (d, 2H, J=6.0 Hz), 1.53 (s, 6H).

Example 38

N-(4-Amino-benzyl)-2-[4-((E)-2-cyano-ethenesulfonyl)-phenyl]-isobutyramide

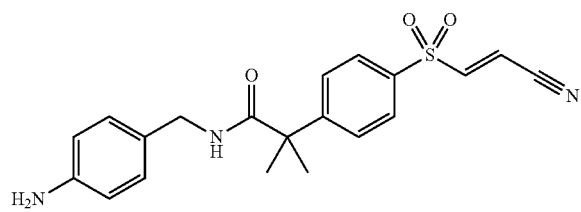 [SMILES: CC(C)(C(=O)NCc1ccc(N)cc1)c1ccc(S(=O)(=O)/C=C/C#N)cc1]

2-[4-((E)-2-Cyano-ethenesulfonyl)-phenyl]-2-methyl-propionic acid (83.0 mg, 0.297 mmol), 4-aminobenzylamine (44.8 uL, 0.396 mmol), N-(3-dimethylaminopropyl)-N'-ethylcarbodiimide hydrochloride (79.0 mg, 0.412 mmol) and 1-hydroxybenzotriazole (20.0 mg, 0.148 mmol) were dissolved in acetonitrile (1.50 mL) and the reaction mixture was allowed to stir 1 h at room temperature. The reaction was diluted with 0.4 mL DMSO, filtered and purified. Purification by mass-directed HPLC using a gradient of 25-75% MeCN/water both containing 0.1% TFA as the eluting solvent to afford N-(4-Amino-benzyl)-2-[4-((E)-2-cyano-ethenesulfonyl)-phenyl]-isobutyramide trifluoroacetic acid salt (69 mg, 47%) as a white lyophilate. MS: 384 (M+H); 1H-NMR (DMSO-d6, 400 MHz) δ 8.23 (d, 1H, J=15.7 Hz), 8.05 (t, 1H, J=5.9 Hz), 7.86 (d, 2H, J=8.6 Hz), 7.62 (d, 2H, J=8.6 Hz), 7.12 (d, 2H, J=8.4 Hz), 7.02 (d, 2H, J=8.4 Hz), 6.90 (d, 1H, J=15.7 Hz), 4.35 (br s, 3H), 4.19 (d, 2H, J=5.9 Hz), 1.51 (s, 6H).

Example 39

2-[4-((E)-2-Cyano-ethenesulfonyl)-phenyl]-N-(3-fluoro-benzyl)-isobutyramide

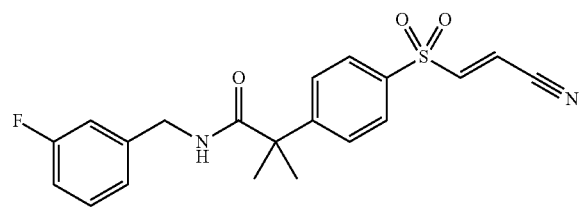 [SMILES: CC(C)(C(=O)NCc1cccc(F)c1)c1ccc(S(=O)(=O)/C=C/C#N)cc1]

2-[4-((E)-2-Cyano-ethenesulfonyl)-phenyl]-2-methyl-propionic acid (75.0 mg, 0.268 mmol), 3-fluorobenzylamine (30.6 uL, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in acetonitrile (1.00 mL) and the reaction mixture was allowed to stir for 2 hours at room temperature. The reaction was concentrated under reduced pressure and the residue was taken up in 1.6 mL of DMSO. Purification by mass-directed HPLC using a gradient of 25-75% MeCN/water both containing 0.1% TFA as the eluting solvent to afford 2-[4-((E)-2-Cyano-ethenesulfonyl)-phenyl]-N-(3-fluoro-benzyl)-isobutyramide (17 mg, 16%) as a white lyophilate. MS: 387 (M+H); 1H-NMR (CDCl3, 400 MHz) δ 7.87 (d, 2H, J=8.7 Hz), 7.61 (d, 2H, J=8.7 Hz), 7.32-7.23 (m, 1H), 7.20 (d, 1H, J=15.6 Hz), 7.00-6.91 (m, 2H), 6.84-6.78 (m, 1H), 6.55 (d, 1H, J=15.6 Hz), 5.62-5.49 (m, 1H), 4.40 (d, 2H, J=5.9 Hz), 1.64 (s, 6H).

Example 40

2-[4-((E)-2-Cyano-ethenesulfonyl)-phenyl]-N-(2-fluoro-benzyl)-isobutyramide

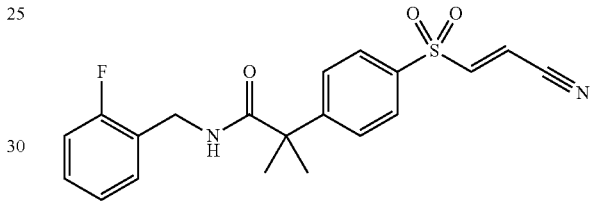

2-[4-((E)-2-Cyano-ethenesulfonyl)-phenyl]-2-methyl-propionic acid (75.0 mg, 0.268 mmol), 2-fluorobenzylamine (30.6 uL, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in acetonitrile (1.00 mL) and the reaction mixture was allowed to stir for 2 hours at room temperature. The reaction was concentrated under reduced pressure and the residue was taken up in 1.6 mL of DMSO. Purification by mass-directed HPLC using a gradient of 25-75% MeCN/water both containing 0.1% TFA as the eluting solvent to afford 2-[4-((E)-2-Cyano-ethenesulfonyl)-phenyl]-N-(2-fluoro-benzyl)-isobutyramide (40 mg, 38%) as a white lyophilate. MS: 387 (M+H); 1H-NMR (CDCl3, 400 MHz) δ 7.83 (d, 2H, J=8.7 Hz), 7.56 (d, 2H, J=8.7 Hz), 7.31-7.22 (m, 2H), 7.19 (d, 1H, J=15.6 Hz), 7.12-7.06 (m, 1H), 7.05-6.98 (m, 1H), 6.54 (d, 1H, J=15.7 Hz), 5.69-5.54 (m, 1H), 4.44 (d, 2H, J=5.9 Hz), 1.60 (s, 6H).

Example 41

2-[4-((E)-2-Cyano-ethenesulfonyl)-phenyl]-N-(4-fluoro-benzyl)-N-methyl-isobutyramide

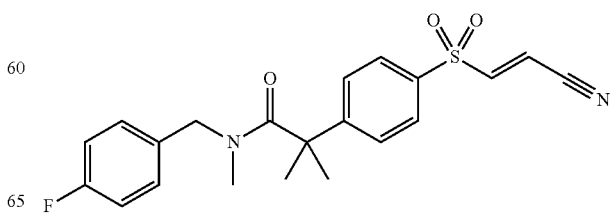

2-[4-((E)-2-Cyano-ethenesulfonyl)-phenyl]-2-methyl-propionic acid (75.0 mg, 0.268 mmol), (4-fluoro-benzyl)-methyl-amine (37.4 mg, 0.268 mmol), N-(3-dimethylamino-propyl)-N'-ethylcarbodiimide hydrochloride (51.5 mg, 0.268 mmol) and 1-hydroxybenzotriazole (18.1 mg, 0.134 mmol) were dissolved in acetonitrile (1.00 mL) and the reaction mixture was allowed to stir for 2 hours at room temperature. The reaction was concentrated under reduced pressure and the residue was taken up in 1.6 mL of DMSO. Purification by mass-directed HPLC using a gradient of 25-75% MeCN/water both containing 0.1% TFA as the eluting solvent to afford 2-[4-((E)-2-Cyano-ethenesulfonyl)-phenyl]-N-(4-fluoro-benzyl)-N-methyl-isobutyramide (24 mg, 22%) as a white lyophilate. MS: 401 (M+H); 1H-NMR (CDCl3, 400 MHz, mixture of rotamers) δ 7.84 (d, 2H, J=8.6 Hz), 7.46 (d, 2H, J=8.6 Hz), 7.32-7.13 (m, 3H), 7.06-6.96 (m, 2H), 6.55 (d, 1H, J=15.7 Hz), 4.68-3.79 (m, 2H), 3.00-2.24 (m, 3H), 1.61 (s, 6H).

Example 42

2-[4-((E)-2-Cyano-ethenesulfonyl)-phenyl]-N-[3-(2-methoxy-ethoxy)-phenyl]-isobutyramide

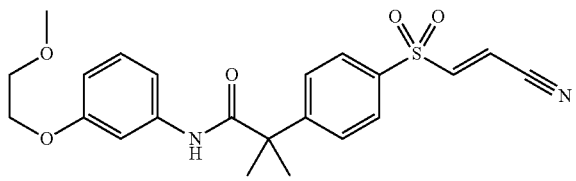 [SMILES: COCCOc1cccc(NC(=O)C(C)(C)c2ccc(S(=O)(=O)/C=C/C#N)cc2)c1]

a) 2-Bromoethyl methyl ether (0.800 mL, 8.51 mmol) was added to a mixture of m-nitrophenol (1.00 g, 7.19 mmol) and potassium carbonate (1.49 g, 10.8 mmol) in N-methylpyrrolidinone (6.0 mL) and the mixture was heated at 50° C. in a vial overnight then cooled to room temperature. The mixture was diluted with water (6 mL) and extracted with 2:1 EtOAc:Hex (3×18 mL). The combined organics were washed with satd. aq. NaHCO3 (30 mL) and brine (30 mL), dried over sodium sulfate, filtered and concentrated in vacuo to afford 1-(2-Methoxy-ethoxy)-3-nitro-benzene (1.328 g, 93%) as an orange oil.

b) 1-(2-Methoxy-ethoxy)-3-nitro-benzene (1.32 g, 6.69 mmol) and 10% palladium on carbon (50% Wet) (0.210 g, 0.0987 mmol) in Methanol (15.0 mL) was shaken under an atmosphere of hydrogen (30 psi) for 2 h, filtered through Celite and concentrated in vacuo to afford 3-(2-Methoxy-ethoxy)-phenylamine (1.064 g, 95%) as an orange oil.

c) 2-[4-((E)-2-Cyano-ethenesulfonyl)-phenyl]-2-methyl-propionic acid (85.0 mg, 0.304 mmol), 3-(2-Methoxy-ethoxy)-phenylamine (65 mg, 0.39 mmol), N-(3-dimethyl-amino-propyl)-N'-ethylcarbodiimide hydrochloride (88 mg, 0.46 mmol) and 1-hydroxybenzotriazole (41.0 mg, 0.303 mmol) were dissolved in acetonitrile (1.5 mL, 29 mmol) and the reaction mixture was allowed to stir at room temperature overnight. The reaction was diluted with 0.4 mL DMSO, filtered and purified. Purification by mass-directed HPLC using a gradient of 25-75% MeCN/water both containing 0.1% TFA as the eluting solvent afforded 2-[4-((E)-2-Cyano-ethenesulfonyl)-phenyl]-N-[3-(2-methoxy-ethoxy)-phenyl]-isobutyramide (72 mg, 55%) as a white foam. MS: 429 (M+H); 1H-NMR (CDCl3, 400 MHz) δ 7.91 (d, 2H, J=8.6 Hz), 7.68 (d, 2H, J=8.6 Hz), 7.23 (d, 1H, J=15.6 Hz), 7.22 (m, 1H), 7.18 (m, 1H), 6.84 (ddd, 1H, J=0.6, 1.9, 8.0 Hz), 6.79 (br s, 1H), 6.68 (ddd, 1H, J=0.6, 2.4, 8.3 Hz), 6.58 (d, 1H, J=15.6 Hz), 4.11 (m, 2H), 3.73 (m, 2H), 3.44 (s, 3H), 1.70 (s, 6H).

Example 43

(3-{2-[4-((E)-2-Cyano-ethenesulfonyl)-phenyl]-2-methyl-propionylamino}-phenoxy)-acetic acid

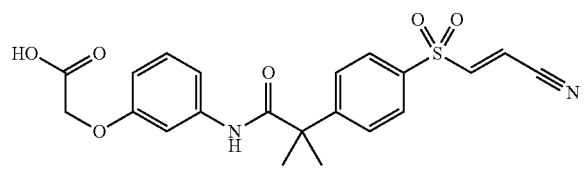 [SMILES: CC(C)(C(=O)Nc1cccc(OCC(=O)O)c1)c1ccc(S(=O)(=O)/C=C/C#N)cc1]

2-[4-((E)-2-Cyano-ethenesulfonyl)-phenyl]-2-methyl-propionic acid (85.0 mg, 0.304 mmol), (3-Amino-phenoxy)-acetic acid tert-butyl ester (91 mg, 0.41 mmol, as prepared in Takeda, Y. et al. *Chem. Pharm. Bull.* 1993, 46, 434), N-(3-dimethylaminopropyl)-N'-ethylcarbodiimide hydrochloride (88 mg, 0.46 mmol) and 1-hydroxybenzotriazole (42 mg, 0.31 mmol) were dissolved in acetonitrile (2.0 mL) and the reaction mixture was allowed to stir at room temperature overnight. The mixture was then treated with trifluoroacetic acid (1.00 mL, 13.0 mmol). After stirring overnight, the mixture was filtered and purified by mass-directed HPLC to afford (3-{2-[4-((E)-2-Cyano-ethenesulfonyl)-phenyl]-2-methyl-propionylamino}-phenoxy)-acetic acid (69 mg, 53%) as a white lyophilate. MS: 429 (M+H); 1H-NMR (DMSO-d6, 400 MHz) δ 12.98 (br s, 1H), 9.20 (s, 1H), 8.23 (d, 1H, J=15.6 Hz), 7.90 (d, 2H, J=8.6 Hz), 7.67 (d, 2H, J=8.6 Hz), 7.28 (m, 1H), 7.21 (m, 1H), 7.16 (m, 1H), 6.91 (d, 1H, J=15.6 Hz), 6.59 (ddd, 1H, J=1.1, 2.5, 8.0 Hz), 4.61 (s, 2H), 1.59 (s, 6H).

Example 44

2-[4-((E)-2-Cyano-ethenesulfonyl)-phenyl]-N-(3-methoxy-benzyl)-isobutyramide

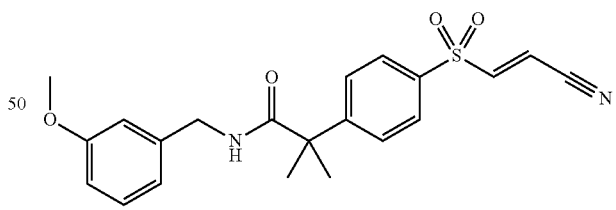

2-[4-((E)-2-Cyano-ethenesulfonyl)-phenyl]-2-methyl-propionic acid (75.0 mg, 0.268 mmol), 3-methoxy-benzylamine (34.7 μL, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in acetonitrile (1.00 mL) and the reaction mixture was allowed to stir for 2 hours at room temperature. The reaction was concentrated under reduced pressure and the residue was taken up in 1.6 mL of DMSO. Purification by mass-directed HPLC using a gradient of 25-75% MeCN/water both containing 0.1% TFA as the eluting solvent afforded 2-[4-((E)-2-Cyano-ethenesulfonyl)-phenyl]-N-(3- methoxy-benzyl)-isobutyramide (40 mg, 37%) as a white lyophilate. MS: 399 (M+H); 1H-NMR (CDCl3, 400 MHz) δ 7.85 (d, 2H, J=8.6 Hz), 7.61 (d, 2H, J=8.6 Hz), 7.25-7.16 (m, 2H), 6.84-6.78 (m, 1H), 6.77-6.72 (m, 1H), 6.69-6.65 (m, 1H), 6.54 (d, 1H, J=15.7 Hz), 5.57-5.48 (m, 1H), 4.38 (d, 2H, J=5.7 Hz), 3.77 (s, 3H), 1.64 (s, 6H).

Example 45

2-[4-((E)-2-Cyano-ethenesulfonyl)-phenyl]-N-(2-methoxy-benzyl)-isobutyramide

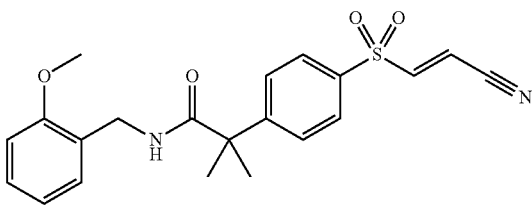 [SMILES: COc1ccccc1CNC(=O)C(C)(C)c1ccc(S(=O)(=O)/C=C/C#N)cc1]

2-[4-((E)-2-Cyano-ethenesulfonyl)-phenyl]-2-methyl-propionic acid (75.0 mg, 0.268 mmol), 2-methoxy-benzylamine (34.7 µL, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in acetonitrile (1.00 mL) and the reaction mixture was allowed to stir for 2 hours at room temperature. The reaction was concentrated under reduced pressure and the residue was taken up in 1.6 mL of DMSO. Purification by mass-directed HPLC using a gradient of 25-75% MeCN/water both containing 0.1% TFA as the eluting solvent afforded 2-[4-((E)-2-Cyano-ethenesulfonyl)-phenyl]-N-(2-methoxy-benzyl)-isobutyramide (48 mg, 45%) as a white lyophilate. MS: 399 (M+H); HNMR (CDCl3, 400 MHz) δ 7.81 (d, 2H, J=8.7 Hz), 7.53 (d, 2H, J=8.7 Hz), 7.30-7.23 (m, 1H), 7.23-7.16 (m, 2H), 6.94-6.87 (m, 1H), 6.85-6.80 (m, 1H), 6.54 (d, 1H, J=15.7 Hz), 5.89-5.80 (m, 1H), 4.38 (d, 2H, J=5.8 Hz), 3.69 (s, 3H), 1.58 (s, 6H).

Example 46

2-[4-((E)-2-Cyano-ethenesulfonyl)-phenyl]-N-(2-methoxy-benzyl)-N-methyl-isobutyramide

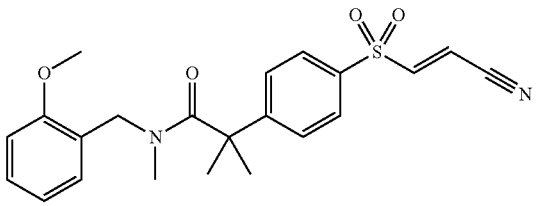 [SMILES: COc1ccccc1CN(C)C(=O)C(C)(C)c1ccc(S(=O)(=O)/C=C/C#N)cc1]

2-[4-((E)-2-Cyano-ethenesulfonyl)-phenyl]-2-methyl-propionic acid (75.0 mg, 0.268 mmol), (2-methoxy-benzyl)-methyl-amine (40.6 mg, 0.268 mmol), N-(3-dimethylaminopropyl)-N'-ethylcarbodiimide hydrochloride (51.5 mg, 0.268 mmol) and 1-hydroxybenzotriazole (18.1 mg, 0.134 mmol) were dissolved in acetonitrile (1.00 mL) and the reaction mixture was allowed to stir for 2 hours at room temperature. The reaction was concentrated under reduced pressure and the residue was taken up in 1.6 mL of DMSO. Purification by mass-directed HPLC using a gradient of 25-75% MeCN/water both containing 0.1% TFA as the eluting solvent afforded 2-[4-((E)-2-Cyano-ethenesulfonyl)-phenyl]-N-(2-methoxy-benzyl)-N-methyl-isobutyramide (28 mg, 25%) as a white lyophilate. MS: 413 (M+H); 1H-NMR (DMSO-d6, 400 MHz, 100° C.) δ 8.03 (d, 1H, J=15.7 Hz), 7.87-7.81 (m, 2H), 7.55-7.49 (m, 2H), 7.24-7.17 (m, 1H), 7.02-6.96 (m, 1H), 6.96-6.85 (m, 2H), 6.75 (d, 1H, J=15.7 Hz), 4.35 (s, 2H), 3.74 (s, 3H), 2.48 (s, 3H), 1.52 (s, 6H)

Example 47

(E)-3-{4-[1-Methyl-1-(5-phenylamino-[1,3,4]oxadiazol-2-yl)-ethyl]-benzenesulfonyl}-acrylonitrile

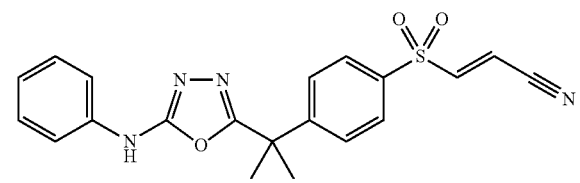 [SMILES: CC(C)(c1ccc(S(=O)(=O)/C=C/C#N)cc1)c1nnc(Nc2ccccc2)o1]

2-[4-((E)-2-Cyano-ethenesulfonyl)-phenyl]-2-methyl-propionic acid (101 mg, 0.362 mmol), N-(3-dimethylaminopropyl)-N'-ethylcarbodiimide hydrochloride (211 mg, 1.10 mmol) and 4-phenyl-3-thiosemicarbazide (65 mg, 0.39 mmol) were combined in methylene chloride (3.00 mL) and stirred overnight. The mixture was concentrated in vacuo, taken up in DMSO and purified by mass-directed HPLC (25-75% MeCN/water, TFA modifier). Following lyophilization, (E)-3-{4-[1-Methyl-1-(5-phenylamino-[1,3,4]oxadiazol-2-yl)-ethyl]-benzenesulfonyl}-acrylonitrile trifluoroacetic acid salt (35 mg, 19%) was isolated as an off-white lyophilate. MS: 395 (M+H); 1H-NMR (DMSO-d6, 400 MHz) δ 10.38 (s, 1H), 8.23 (d, 1H, J=15.6 Hz), 7.91 (d, 2H, J=8.0 Hz), 7.66 (d, 2H, J=8.0 Hz), 7.52 (d, 2H, J=7.8 Hz), 7.32 (m, 2H), 6.98 (m, 1H), 6.92 (d, 1H, J=15.6 Hz), 1.77 (s, 6H).

Example 48

(E)-3-{4-[1-(5-Ethylamino-[1,3,4]oxadiazol-2-yl)-1-methyl-ethyl]-benzenesulfonyl}-acrylonitrile

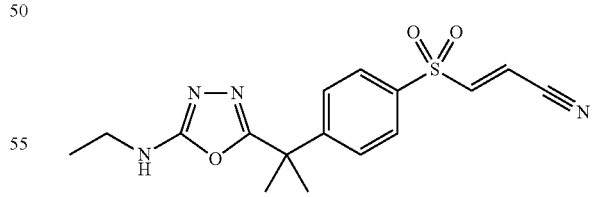

2-[4-((E)-2-Cyano-ethenesulfonyl)-phenyl]-2-methyl-propionic acid (105 mg, 0.376 mmol), N-(3-dimethylaminopropyl)-N'-ethylcarbodiimide hydrochloride (241 mg, 1.26 mmol) and 4-ethyl-3-thiosemicarbazide (60.0 mg, 0.503 mmol) were combined in methylene chloride (3 mL) and stirred overnight. The mixture was concentrated in vacuo, taken up in DMSO and purified by mass-directed HPLC (25-75% MeCN/water, TFA modifier). Following lyophilization, (E)-3-{4-[1-(5-Ethylamino-[1,3,4]oxadiazol- 2-yl)-1-methyl-ethyl]-benzenesulfonyl}-acrylonitrile trifluoroacetic acid salt 19 mg, 11%) was isolated as a beige lyophilate. MS: 347 (M+H); 1H-NMR (acetone-d6, 400 MHz) δ 7.94 (d, 2H, J=8.1 Hz), 7.89 (d, 1H, J=15.7 Hz), 7.66 (d, 2H, J=8.1 Hz), 6.83 (d, 1H, J=15.7 Hz), 6.53 (br s, 1H), 3.30 (q, 2H, J=7.2 Hz), 1.76 (s, 6H), 1.20 (t, 3H, J=7.2 Hz).

Example 49

(E)-3-{4-[1-(1H-Benzimidazol-2-yl)-1-methyl-ethyl]-benzenesulfonyl}-acrylonitrile

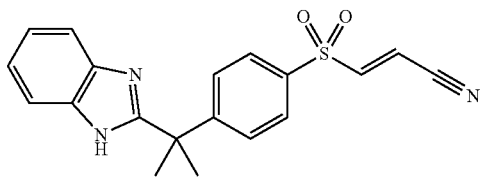 [SMILES: CC(C)(c1ccc(S(=O)(=O)/C=C/C#N)cc1)c1nc2ccccc2[nH]1]

2-[4-((E)-2-Cyano-ethenesulfonyl)-phenyl]-2-methyl-propionic acid (112 mg, 0.401 mmol), 1,2-benzenediamine (51.0 mg, 0.472 mmol), N-(3-dimethylaminopropyl)-N'-ethylcarbodiimide hydrochloride (98 mg, 0.51 mmol) and 1-hydroxybenzotriazole (27 mg, 0.20 mmol) were combined in tetrahydrofuran (6.0 mL) and stirred at room temperature. After 1 h, methylene chloride (1.0 mL) was added to aid in solubility. After stirring overnight, Acetic acid (0.65 mL, 11 mmol) was added and the mixture was heated to 70° C. until complete cyclization of the aniline-amide. The mixture was concentrated in vacuo, taken up in DMSO and purified by mass-directed HPLC to afford (E)-3-{4-[1-(1H-Benzimidazol-2-yl)-1-methyl-ethyl]-benzenesulfonyl}-acrylonitrile trifluoroacetic acid salt (45 mg, 24%) as an off-white lyophilate. MS: 352 (M+H); 1H-NMR (DMSO-d6, 400 MHz) δ 8.23 (d, 1H, J=15.7 Hz), 7.90 (d, 2H, J=8.2 Hz), 7.65 (m, 4H), 7.39 (br s, 2H), 6.91 (d, 1H, J=15.7 Hz), 1.89 (s, 6H).

Example 50

(E)-3-{4-[1-Methyl-1-(5-methyl-benzoxazol-2-yl)-ethyl]-benzenesulfonyl}-acrylonitrile

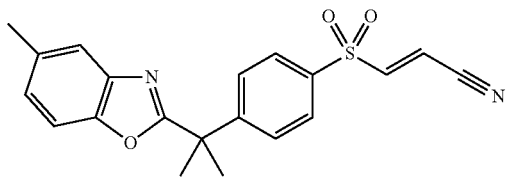 [SMILES: Cc1ccc2oc(C(C)(C)c3ccc(S(=O)(=O)/C=C/C#N)cc3)nc2c1]

a) 2-[4-((E)-2-Cyano-ethenesulfonyl)-phenyl]-2-methyl-propionic acid (124 mg, 0.444 mmol), 2-amino-4-methyl-phenol (61.0 mg, 0.495 mmol) and 1-hydroxybenzotriazole (6.0 mg, 0.044 mmol) were combined in 1,2-dichloroethane (4.0 mL, 51 mmol), and N-(3-dimethylaminopropyl)-N'-ethylcarbodiimide hydrochloride (105 mg, 0.548 mmol) was added. Stir at room temperature in a vial for 2 h, then the mixture was concentrated in vacuo, taken up in DMSO and purified by mass-directed HPLC to afford 2-[4-((E)-2-Cyano-ethenesulfonyl)-phenyl]-N-(2-hydroxy-5-methyl-phenyl)-isobutyramide as an oil.

b) 2-[4-((E)-2-Cyano-ethenesulfonyl)-phenyl]-N-(2-hydroxy-5-methyl-phenyl)-isobutyramide (42 mg, 0.11 mmol) was dissolved in acetic acid (2.0 mL, 35 mmol) and heated at 105° C. for 3 d. The mixture was concentrated in vacuo, taken up in DMSO and purified by mass-directed HPLC (25-85% MeCN:Water, TFA modifier) to afford (E)-3-{4-[1-Methyl-1-(5-methyl-benzoxazol-2-yl)-ethyl]-benzenesulfonyl}-acrylonitrile trifluoroacetic acid salt (15 mg, 28%) as an off-white lyophilate. MS: 367 (M+H); 1H-NMR (DMSO-d6, 400 MHz) δ 8.21 (d, 1H, J=15.6 Hz), 7.88 (d, 2H, J=8.4 Hz), 7.63 (d, 2H, J=8.4 Hz), 7.56 (s, 1H), 7.52 (d, 1H, J=8.3 Hz), 7.18 (d, 1H, J=8.3 Hz), 6.90 (d, 1H, J=15.6 Hz), 2.42 (s, 3H), 1.84 (s, 6H).

Example 51

(E)-3-{4-[1-Methyl-1-(5-methyl-oxazol-2-yl)-ethyl]-benzenesulfonyl}-acrylonitrile

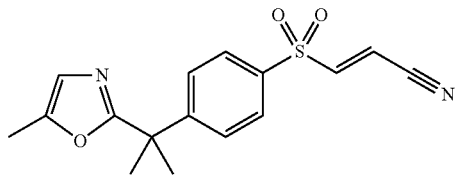 [SMILES: Cc1cnc(C(C)(C)c2ccc(S(=O)(=O)/C=C/C#N)cc2)o1]

2-[4-((E)-2-Cyano-ethenesulfonyl)-phenyl]-N-prop-2-ynyl-isobutyramide (53 mg, 0.17 mmol) and gold(III) chloride (5.0 mg, 0.016 mmol) were combined in acetonitrile-d3 (1.0 mL), and the rate of isomerization was monitored by 1H-NMR. Once complete (4 days) the mixture was filtered and purified by mass-directed HPLC and lyophilized to afford an oil. Reconcentration from MeCN remained an oil, which slowly turned purple. The mixture was redissolved in MeCN, treated with macroporous carbonate resin (3 mmol/g, 0.1 g) for 30 min and filtered to give a clear solution and purple solids which were captured on the filter. Relyophilize as the free base to afford (E)-3-{4-[1-Methyl-1-(5-methyl-oxazol-2-yl)-ethyl]-benzenesulfonyl}-acrylonitrile as an off-white wax (16 mg, 30%). MS: 317 (M+H); 1H-NMR (DMSO-d6, 400 MHz) δ 8.22 (d, 1H, J=15.6 Hz), 7.86 (d, 2H, J=8.6 Hz), 7.54 (d, 2H, J=8.6 Hz), 6.91 (d, 1H, J=15.6 Hz), 6.79 (s, 1H), 2.22 (s, 3H), 1.71 (s, 6H).

Example 52

Cyclohexanecarboxylic acid N'-{2-[4-((E)-2-cyano-ethenesulfonyl)-phenyl]-2-methyl-propionyl}-hydrazide

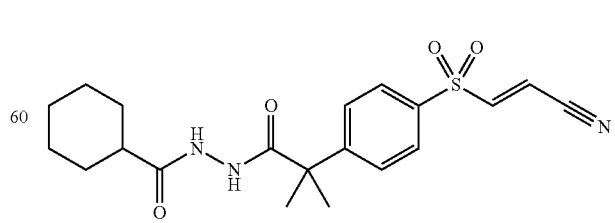

2-[4-((E)-2-Cyano-ethenesulfonyl)-phenyl]-2-methyl-propionic acid (131 mg, 0.469 mmol), cyclohexanecarboxylic acid hydrazide (72.0 mg, 0.506 mmol), N-(3-dimethylaminopropyl)-N'-ethylcarbodiimide hydrochloride (119 mg, 0.621 mmol) and 1-hydroxybenzotriazole (7.0 mg, 0.052 mmol) were combined in acetonitrile (3.0 mL) and stirred at room temperature. After 4 h, the mixture was diluted with DMSO (0.4 mL), filtered and purified by mass-directed HPLC (25-85% MeCN:Water, TFA modifier) to afford Cyclohexanecarboxylic acid N'-{2-[4-((E)-2-cyano-ethenesulfonyl)-phenyl]-2-methyl-propionyl}-hydrazide (108 mg, 57%) as a white lyophilate. MS: 404 (M+H); 1H-NMR (DMSO-d6, 400 MHz) δ 9.52 (s, 1H), 9.39 (s, 1H), 8.24 (d, 1H, J=15.6 Hz), 7.86 (d, 2H, J=8.7 Hz), 7.73 (d, 2H, J=8.7 Hz), 6.90 (d, 1H, J=15.6 Hz), 2.15 (m, 1H), 1.6-1.7 (m, 5H), 1.50 (s, 6H), 1.1-1.4 (m, 5H).

Example 53

(E)-3-{4-[1-(5-Cyclohexyl-[1,3,4]oxadiazol-2-yl)-1-methyl-ethyl]-benzenesulfonyl}-acrylonitrile

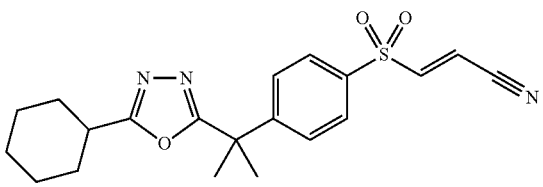 [SMILES: CC(C)(c1ccc(S(=O)(=O)/C=C/C#N)cc1)c1nnc(C2CCCCC2)o1]

Cyclohexanecarboxylic acid N'-{2-[4-((E)-2-cyano-ethenesulfonyl)-phenyl]-2-methyl-propionyl}-hydrazide (52 mg, 0.13 mmol) was dissolved in 1,4-dioxane (2.00 mL) and phosphoryl chloride (0.200 mL, 2.14 mmol) was added and the mixture was heated at 80° C. for 2 h, then cooled on ice before being added to 5 g of ice. The mixture was diluted with satd. sodium bicarbonate (10 mL) and extracted with DCM (3×10 mL). The organic extracts were washed with 1:1 brine:satd. sodium bicarbonate (10 mL), dried over sodium sulfate, filtered and concentrated in vacuo to afford (E)-3-{4-[1-(5-Cyclohexyl-[1,3,4]oxadiazol-2-yl)-1-methyl-ethyl]-benzenesulfonyl}-acrylonitrile (38 mg, 76%) as a white foam. MS: 386 (M+H); HNMR (CDCl3, 400 MHz) δ 7.85 (d, 2H, J=8.7 Hz), 7.51 (d, 2H, J=8.7 Hz), 7.20 (d, 1H, J=15.7 Hz), 6.55 (d, 1H, J=15.7 Hz), 2.84 (tt, 1H, J=3.7, 11.3 Hz), 2.03 (m, 2H), 1.84 (s, 6H), 1.79 (m, 2H), 1.71 (m, 2H), 1.24-1.40 (m, 4H).

Example 54

(E)-3-(3-tert-Butyl-benzenesulfonyl)-acrylonitrile

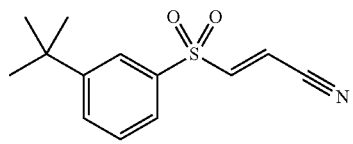 [SMILES: CC(C)(C)c1cccc(S(=O)(=O)/C=C/C#N)c1]

To a solution of 3-tert-butyl-bromobenzene (2.13 g, 10 mmol) in anhydrous THF (50 ml) under nitrogen at −80° C. (ether/dry ice), was added slowly n-BuLi (2.5 M in hexane, 11 mmol). A cloudy suspension was slowly formed. Twenty minutes after BuLi addition, a stream of sulfur dioxide was bubbled through the mixture for 15 min. The reaction mixture was then allowed to warm up to room temperature and the solvent was removed under reduced pressure. The sulfinate residue was dissolved in water (15 ml), acetic acid (8 ml), and MeOH (20 ml), followed by addition of 2-chloroacrylonitrile (18 mmol). The resulting mixture was stirred at room temperature overnight. The organic solvents were removed in vacuo and the residue was diluted with 20 ml of water. The solution was adjusted to pH5-6 with sat. K$_2$HPO$_4$ aq. solution, then extracted with dichloromethane (2×50 ml), dried over MgSO$_4$. After filtration, the filtrate was stirred with triethylamine (20 mmol) for 1 h. The solution was washed with 10% aq. citric acid and brine then dried over MgSO$_4$. The crude product was purified by flash column chromatography (silica gel, dichloromethane/EtOAc, gradient) to give (E)-3-(3-tert-Butyl-benzenesulfonyl)-acrylonitrile (0.76 g, 31%) as a white solid. MS: 250 (M+H); 1H-NMR (CDCl3, 400 MHz) δ 7.89 (s, 1H), 7.76 (d, 1H, J=7.7 Hz), 7.70 (d, 1H, J=7.9 Hz), 7.55 (m, 1H), 7.23 (d, 1H, J=15.9 Hz), 6.55 (d, 1H, J=15.9 Hz), 1.37 (s, 9H).

Example 55

(E)-3-(4-tert-Butyl-benzenesulfonyl)-acrylamide

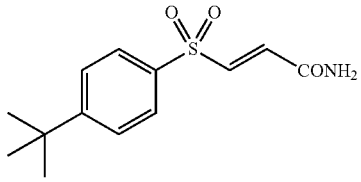 [SMILES: CC(C)(C)c1ccc(S(=O)(=O)/C=C/C(N)=O)cc1]

a) A solution of 4-tert-butyl-bromobenzene (500 mg, 2.34 mmol) in dry THF (10 ml) was cooled to −80° C., treated with phenyl lithium (1.5M, 2.58 mmol) and n-BuLi (1.5M, 2.58 mmol) drop wise at −80° C. After 30 min, sulfur dioxide gas was bubbled into the mixture for one hour, and then the mixture was allowed to come to room temperature. The reaction mixture was concentrated and washed with diethyl ether to obtain 4-tert-butylbenzene sulfinic acid lithium salt as a white solid (450 mg, 94%).

b) A solution of 4-tert-butylbenzene sulfinic acid lithium salt (500 mg, 2.4 mmol) and 2,3-dibromo-propionamide (678 mg, 2.93 mmol) in DMF (5 ml) was heated to 80° C. for 15 hours. Then the reaction mixture as diluted with water, extracted with ethyl acetate, dried over sodium sulfate, filtered and concentrated. The crude product was purified by silica gel column chromatography (20% Ethyl acetate:Hexane) to obtain (E)-3-(4-tert-Butyl-benzenesulfonyl)-acrylamide (50 mg, 8%) as an off white solid, mp=151° C. LCMS (ESI): 268 (M+H); 1H-NMR (400 MHz, DMSO-d$_6$) δ 1.31 (s, 9H), 6.95-6.98 (d, J=14.8 Hz, 1H), 7.40-7.44 (d, J=14.8 Hz, 1H), 7.69-7.71 (d, J=8.0 Hz, 2H), 7.83-7.85 (d, J=8.0 Hz, 2H), 8.03 (brs, 2H).

Example 56

1-tert-Butyl-4-[((E)-prop-1-ene)-1-sulfonyl]-benzene

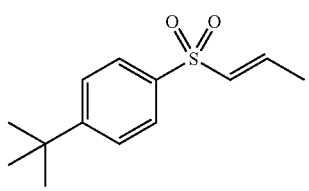 [SMILES: C/C=C/S(=O)(=O)c1ccc(C(C)(C)C)cc1]

a) A solution of sodium bicarbonate (1.44 g, 17.2 mmol) and sodium sulfite (2.16 g, 17.2 mmol) in water (9 ml) was heated to 80° C. for 3 h, then 4-tert-butylphenylsulfonyl chloride (2 g, 8.59 mmol) was added in two portions and again heated to 80° C. for 1 h. The mixture was cooled to room temperature, allowed to stand for 2 h, and the solids collected by filtration then dried on high vacuum to obtain 4-tert-butylbenzene sulfinic acid sodium salt (1.61 g, 85%) as a white solid.

b) Analogous to Example 57b, 1,2-dibromopropane and 4-tert-butylbenzene sulfinic acid sodium salt (0.7 g) afforded 1-tert-Butyl-4-[((E)-prop-1-ene)-1-sulfonyl]-benzene (130 mg, 17%) as an off white solid, mp=80° C. LCMS (ESI): 239 (M+H); 1H-NMR (400 MHz, CDCl3) δ 1.34 (s, 9H), 1.91-1.93 (dd, J=6.8, 1.6 Hz, 3H), 6.32-6.37 (m, 1H), 6.93-6.99 (m, 1H), 7.53-7.55 (d, J=8.8 Hz, 2H), 7.78-7.80 (d, J=8.8 Hz, 2H).

Example 57

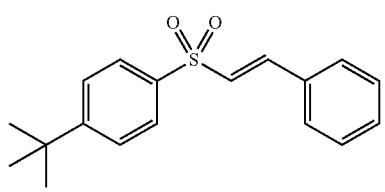 [SMILES: CC(C)(C)c1ccc(S(=O)(=O)/C=C/c2ccccc2)cc1]

1-tert-Butyl-4-((E)-2-phenyl-ethenesulfonyl)-benzene

A solution of 4-tert-butylbenzene sulfinic acid sodium salt (3.0 g, 13.6 mmol) and 1,2-dibromoethyl benzene (4.31 g, 16.3 mmol) in DMF (30 ml) was heated to 80° C. for 15 h. The reaction mixture was purified by silica gel column chromatography (5% Ethyl acetate:hexane) to obtain 1-tert-Butyl-4-((E)-2-phenyl-ethenesulfonyl)-benzene (104 mg, 3%) as an off white solid, mp=95° C. LCMS (ESI): 301 (M+H); 1H-NMR (400 MHz, CDCl3) δ 1.34 (s, 9H), 6.84-6.88 (d, J=15.6 Hz, 1H), 7.38-7.49 (m, 5H), 7.54-7.57 (d, J=8.4 Hz, 2H), 7.65-7.69 (d, J=15.6 Hz, 1H), 7.85-7.88 (d, J=8.4 Hz, 2H).

Example 58

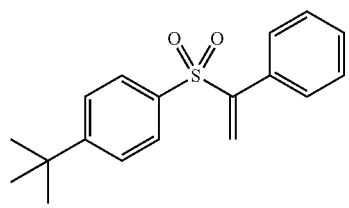 [SMILES: C=C(c1ccccc1)S(=O)(=O)c1ccc(C(C)(C)C)cc1]

1-tert-Butyl-4-(1-phenyl-ethenesulfonyl)-benzene

From the reaction mixture described in Example 59, 1-tert-Butyl-4-(1-phenyl-ethene-sulfonyl)-benzene (147 mg, 4%) was also isolated as an off white solid, mp=99° C. LCMS (ESI): 301 (M+H); 1H-NMR (400 MHz, CDCl3) δ 1.29 (s, 9H), 5.93 (s, 1H), 6.59 (s, 1H), 7.28-7.62 (m, 9H).

Example 59

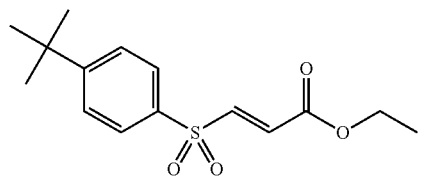 [SMILES: CCOC(=O)/C=C/S(=O)(=O)c1ccc(C(C)(C)C)cc1]

(E)-3-(4-tert-Butyl-benzenesulfonyl)-acrylic acid ethyl ester

A solution of 4-tert-butylbenzene sulfinic acid lithium salt (500 mg, 2.44 mmol) and ethyl 2,3-dibromo propionate (700 mg, 2.69 mmol) in DMF (5 ml) was heated to 80° C. for 20 h. The reaction mixture was diluted with water, extracted with ethyl acetate, dried over Na2SO4, filtered and concentrated. The crude product was purified by silica gel column chromatography (5% Ethyl acetate:Hexane) to obtain (E)-3-(4-tert-Butyl-benzenesulfonyl)-acrylic acid ethyl ester (100 mg, 15%) as an off white solid, mp=88-91° C. LCMS (ESI): 297 (M+H); 1H-NMR (400 MHz, CDCl3) δ 1.29-1.32 (t, J=7.2 Hz, 3H), 1.35 (s, 9H), 4.22-4.27 (q, J=7.2 Hz, 2H), 6.79-6.83 (d, J=15.2 Hz, 1H), 7.31-7.35 (d, J=15.2 Hz, 1H), 7.58-7.60 (d, J=8.0 Hz, 2H), 7.83-7.85 (d, J=8.0 Hz, 2H).

Example 60

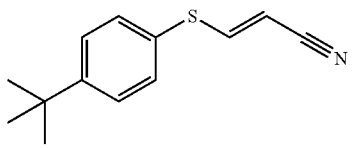

(E)-3-(4-tert-Butyl-phenylsulfanyl)-acrylonitrile (E)-3-(4-tert-Butyl-benzenesulfonyl)-acrylonitrile (100.0 mg, 0.4011 mmol) was dissolved in Chloroform (2.00 mL)

and 4-tert-Butyl-benzenethiol (69 uL, 0.40 mmol) was added, followed by triethylamine (57 uL, 0.41 mmol) and the mixture was stirred at room temperature for 3 h, then applied to an ISCO loading cartridge (5 g, DCM to transfer). Chromatography (ISCO 12 g, 0-20% EtOAc:Hex) afforded (E)-3-(4-tert-Butyl-phenylsulfanyl)-acrylonitrile (84 mg, 97%) as a clear colorless oil. LCMS (ESI): m/z=218 (M+H)+; 1H-NMR (CDCl3, 400 MHz) δ 7.3-7.5 (m, 5H), 4.96 (d, 1H, J=15.6 Hz), 1.34 (s, 9H); $^{13}$C-NMR (CDCl3, 100 MHz) δ 153.7, 152.7, 133.5, 127.2, 124.8, 117.3, 92.6, 34.9, 31.2.

Example 61

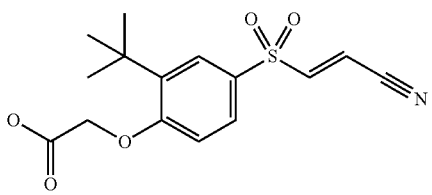 [SMILES: CC(C)(C)c1cc(S(=O)(=O)/C=C/C#N)ccc1OCC(=O)O]

[2-tert-Butyl-4-((E)-2-cyano-ethenesulfonyl)-phenoxy]-acetic acid

To a solution of 2-(4-bromo-2-tert-butylphenoxy)acetic acid (2.86 g, 10 mmol) in anhydrous THF (100 ml) under nitrogen at −80° C. (ether/dry ice), was added slowly Phenyl lithium in toluene 1.8 M (7 mL, 12.5 mmol). After 5 min, to this mixture, n-BuLi (2.5 M in hexane) (5.2 mL, 13 mmol) was added. A cloudy suspension was slowly formed. Twenty minutes after BuLi addition, a stream of sulfur dioxide was bubbled through the mixture for 15 min. The reaction mixture was then allowed to warm up to room temperature and the solvent was removed in vacuo. The sulfinate residue was dissolved in water (15 ml), acetic acid (8 ml), and MeOH (20 ml), followed by addition of 2-chloroacrylonitrile (1.3 g, 15 mmol). The resulting mixture was stirred at room temperature overnight. The organic solvents were removed and the residue was diluted with 20 ml of water. The solution was adjusted to pH5-6 with sat. K$_2$HPO$_4$ aq. solution, then extracted with dichloromethane (2×50 ml) and dried over MgSO4. After filtration, the filtrate was stirred with triethylamine (2.8 mL, 20 mmol) for 1 h. The solution was washed with 10% aq citric acid and brine, and then dried over MgSO4. The final product was purified by flash column chromatography (silica gel, dichloromethane/Ethyl acetate, gradient) to give [2-tert-Butyl-4-((E)-2-cyano-ethenesulfonyl)-phenoxy]-acetic acid (1.03 g, 32%) as a white solid. LCMS (ESI): m/z=322 (M−H)−; 1H-NMR (DMSO-d6, 400 MHz) 13.19 (s, 1H), 8.22 (d, 1H, J=16.6 Hz), 7.74 (dd, 1H, J=2.3, 8.7 Hz), 7.68 (d, 1H, J=2.3 Hz), 7.18 (d, 1H, J=8.7 Hz), 6.84 (d, 1H, J=16.6 Hz), 4.90 (s, 2H), 1.40 (s, 9H); $^{13}$C-NMR (DMSO-d$_6$, 100 MHz) δ 169.3, 161.4, 149.8, 139.0, 128.6, 128.5, 126.4, 114.7, 113.3, 110.7, 64.9, 34.9, 29.0.

Example 62

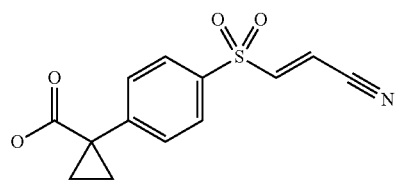 [SMILES: N#C/C=C/S(=O)(=O)c1ccc(C2(C(=O)O)CC2)cc1]

1-[4-((E)-2-Cyano-ethenesulfonyl)-phenyl]-cyclopropanecarboxylic acid

To a solution of 1-(4-bromophenyl)cyclopropanecarboxylic acid (1.0 g, 4.15 mmol) in anhydrous THF (50 ml) under nitrogen at −80° C. (ether/dry ice), was added slowly Phenyl lithium in toluene 1.8 M (2.77 mL, 4.98 mmol). After 5 min, to this mixture, n-BuLi (2.5 M in hexane) (2.2 mL, 5.4 mmol) was added. A cloudy suspension was slowly formed. Twenty minutes after BuLi addition, a stream of sulfur dioxide was bubbled through the mixture for 10 min. The reaction mixture was then allowed to warm up to room temperature and the solvent was removed in vacuo. The sulfinate residue was dissolved in water (10 ml), acetic acid (5 ml), and MeOH (15 ml), followed by addition of 2-chloroacrylonitrile (0.54 g, 6.23 mmol). The resulting mixture was stirred at room temperature overnight. The organic solvents were removed and the residue was diluted with 20 ml of water. The solution was adjusted to pH5-6 with sat. K$_2$HPO$_4$ aq. solution, then extracted with dichloromethane (2×30 ml) and dried over MgSO4. After filtration, the filtrate was stirred with triethylamine (1.16 mL, 8.3 mmol) for 1 h. The solution was washed with 10% aq citric acid and brine, then dried over MgSO4. The final product was purified by flash column chromatography (silica gel, dichloromethane/ Ethyl acetate, gradient) to give 1-[4-((E)-2-Cyano-ethenesulfonyl)-phenyl]-cyclopropanecarboxylic acid (112 mg, 10%) as a white solid. LCMS (ESI): m/z=232 (M−CO2H)—; 1H-NMR (DMSO-d6, 400 MHz) δ 12.59 (s, 1H), 8.24 (d, 1H, J=16.6 Hz), 7.83 (d, 2H, J=8.5 Hz), 7.66 (d, 2H, J=8.5 Hz), 6.91 (d, 1H, J=16.6 Hz), 1.51 (m, 2H), 1.22 (m, 2H).

Example 63

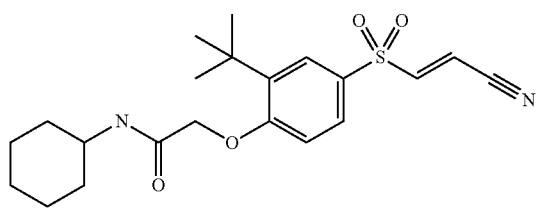 [SMILES: CC(C)(C)c1cc(S(=O)(=O)/C=C/C#N)ccc1OCC(=O)NC1CCCCC1]

2-[2-tert-Butyl-4-((E)-2-cyano-ethenesulfonyl)-phenoxy]-N-cyclohexyl-acetamide

[2-tert-Butyl-4-((E)-2-cyano-ethenesulfonyl)-phenoxy]-acetic acid (57 mg, 0.18 mmol), N-(3-Dimethylaminopropyl)-N'-ethylcarbodiimide hydrochloride (41.0 mg, 0.214 mmol), 1-Hydroxybenzotriazole (5.1 mg, 0.038 mmol) and cyclohexylamine (25 uL, 0.22 mmol) in acetonitrile (0.70 mL) was stirred at room temperature for 5 h, then was filtered, rinsing the vial with DMSO (0.3 mL) and the filtrate was purified by mass-directed HPLC (25-95% MeCN:water, both containing 0.1% TFA) to afford 2-[2-tert-Butyl-4-((E)-2-cyano-ethenesulfonyl)-phenoxy]-N-cyclohexyl-acetamide (27 mg; 38%) as an off white lyophilate. LCMS (ESI): m/z=405 (M+H)+; 1H-NMR (DMSO-d6, 400 MHz) δ 8.22 (d, 1H, J=15.6 Hz), 7.94 (d, 1H, J=7.8 Hz), 7.74 (dd, 1H, J=2.4, 7.8 Hz), 7.67 (d, 1H, J=2.4 Hz), 4.67 (s, 2H), 3.60 (m, 1H), 1.6-1.8 (m, 4H), 1.55 (m, 1H), 1.38 (s, 9H), 1.1-1.3 (m, 5H).

Example 64

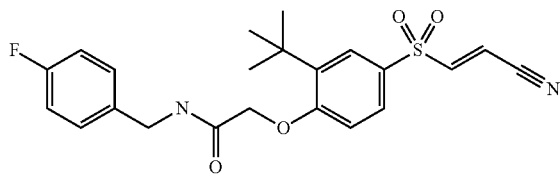 [SMILES: CC(C)(C)c1cc(S(=O)(=O)/C=C/C#N)ccc1OCC(=O)NCc1ccc(F)cc1]

2-[2-tert-Butyl-4-((E)-2-cyano-ethenesulfonyl)-phenoxy]-N-(4-fluoro-benzyl)-acetamide

[2-tert-Butyl-4-((E)-2-cyano-ethenesulfonyl)-phenoxy]-acetic acid (104 mg, 0.322 mmol), N-(3-Dimethylaminopropyl)-N'-ethylcarbodiimide hydrochloride (77 mg, 0.40 mmol), 1-Hydroxybenzotriazole (51 mg, 0.38 mmol) and 4-Fluoro-benzylamine (45 uL, 0.40 mmol) in Acetonitrile (2.0 mL) was stirred at room temperature for 1 h, then was added to an ISCO pre-load cartridge (5 g) and chromatographed (ISCO 12 g, 0-20% Ethyl acetate:Hexanes). Some acetonitrile eluted with product as well as some HOBt. The fraction containing product was concentrated, diluted with MeCN and DCM (3 mL each) and treated with macroporous carbonate resin for 1 h. After filtration and concentration, the residue was dissolved in MeCN, diluted with water and then lyophilized to afford 2-[2-tert-Butyl-4-((E)-2-cyano-ethenesulfonyl)-phenoxy]-N-(4-fluoro-benzyl)-acetamide (64 mg; 46%) as an off-white lyophilate. LCMS (ESI): 431 (M+H); 1H-NMR (DMSO-d6): δ 8.63 (t, 1H, J=5.9 Hz), 8.23 (d, 1H, J=15.6 Hz), 7.74 (dd, 1H, J=2.4, 8.7 Hz), 7.68 (d, 1H, J=2.4 Hz), 7.32 (m, 2H), 7.1-7.2 (m, 3H), 6.84 (d, 1H, J=15.6 Hz), 4.79 (s, 2H), 4.33 (d, 2H, J=5.9 Hz), 1.38 (s, 9H).

Example 65

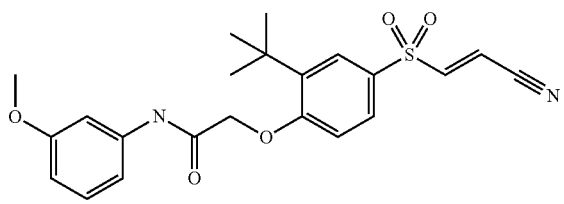 [SMILES: COc1cccc(NC(=O)COc2ccc(S(=O)(=O)/C=C/C#N)cc2C(C)(C)C)c1]

2-[2-tert-Butyl-4-((E)-2-cyano-ethenesulfonyl)-phenoxy]-N-(3-methoxy-phenyl)-acetamide

[2-tert-Butyl-4-((E)-2-cyano-ethenesulfonyl)-phenoxy]-acetic acid (81 mg, 0.25 mmol), N-(3-Dimethylaminopropyl)-N'-ethylcarbodiimide hydrochloride (58.3 mg, 0.304 mmol), 1-Hydroxybenzotriazole (22 mg, 0.16 mmol) and 3-Methoxyaniline (35 uL, 0.31 mmol) in Acetonitrile (1.0 mL) was stirred at room temperature for 5 h, then was filtered, rinsing the vial with DMSO (0.3 mL) and the filtrate was purified by preparative HPLC (25-95% MeCN:water, both containing 0.1% TFA) to afford 2-[2-tert-Butyl-4-((E)-2-cyano-ethenesulfonyl)-phenoxy]-N-(3-methoxy-phenyl)-acetamide (41 mg; 38%) as a white lyophilate. LCMS (ESI): 429 (M+H); 1H-NMR (DMSO-d6): δ 10.26 (s, 1H), 8.22 (d, 1H, J=15.6 Hz), 7.77 (dd, 1H, J=2.4, 8.6 Hz), 7.69 (d, 1H, J=2.4 Hz), 7.30 (m, 1H), 7.23 (m, 1H), 7.17 (d, 1H, J=8.8 Hz), 7.12 (m, 1H), 6.84 (d, 1H, J=15.6 Hz), 6.67 (dd, 1H, J=2.5, 8.2 Hz), 4.95 (s, 2H), 3.73 (s, 3H), 1.42 (s, 9H).

Example 66

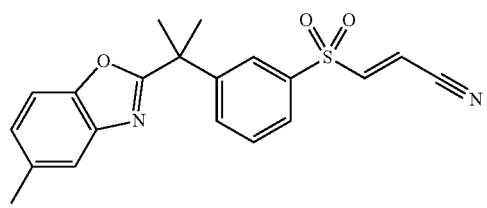 [SMILES: Cc1ccc2oc(C(C)(C)c3cccc(S(=O)(=O)/C=C/C#N)c3)nc2c1]

(E)-3-{3-[1-Methyl-1-(5-methyl-benzoxazol-2-yl)-ethyl]-benzenesulfonyl}-acrylonitrile; compound with trifluoro-acetic acid 1-Hydroxybenzotriazole (40.5 mg, 0.300 mmol), 2-[3-((E)-2-Cyano-ethenesulfonyl)-phenyl]-2-methyl-propionic acid (78.5 mg, 0.281 mmol), 2-Amino-4-methyl-phenol (38.5 mg, 0.313 mmol) and were combined in acetonitrile (2.0 mL) and stirred in a vial for 6 h, then acetic acid (3.0 mL, 53 mmol) was added and the mixture was heated at 90° C. in a sealed vial for 4 days. The mixture was concentrated in vacuo, dissolved in DMSO and purified by preparative mass-directed HPLC (25-75% MeCN:water, both containing 0.1% TFA) to afford (E)-3-{3-[1-Methyl-1-(5-methyl-benzoxazol-2-yl)-ethyl]-benzenesulfonyl}-acrylonitrile; compound with trifluoro-acetic acid (15 mg; 11%) as purplish-white lyophilate. LCMS (ESI): m/z=367 (M+H)+; 1H-NMR (CD3CN, 400 MHz) δ 7.84 (m, 1H), 7.79 (m, 1H), 7.73 (m, 1H), 7.61 (m, 1H), 7.52 (m, 1H), 7.51 (d, 1H, J=15.7 Hz), 7.38 (d, 1H, J=8.3 Hz), 7.17 (m, 1H), 6.60 (d, 1H, J=15.7 Hz), 2.44 (s, 3H), 1.88 (s, 6H); $^{13}$C-NMR (DMSO-$d_6$, 100 MHz) δ 170.3, 148.9, 148.6, 147.2, 140.6, 137.9, 133.9, 132.8, 130.4, 126.8, 126.1, 124.7, 119.6, 114.6, 112.4, 110.2, 41.6, 27.3, 20.9.

Example 67

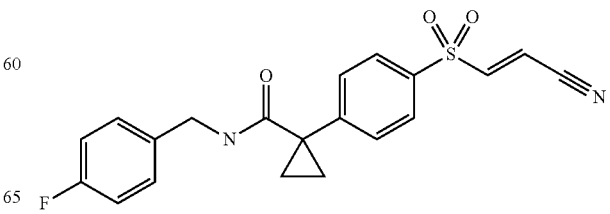

1-[4-((E)-2-Cyano-ethenesulfonyl)-phenyl]-cyclopropanecarboxylic acid 4-fluoro-benzylamide 1-[4-((E)-2-Cyano-ethenesulfonyl)-phenyl]-cyclopropanecarboxylic acid (51 mg, 0.18 mmol), 4-Fluoro-benzylamine (24.2 uL, 0.213 mmol), N-(3-Dimethylaminopropyl)-N'-ethylcarbodiimide hydrochloride (42.3 mg, 0.221 mmol) and 1-Hydroxybenzotriazole (29 mg, 0.21 mmol) were combined in acetonitrile (1.0 mL) and the reaction mixture was allowed to stir at room temperature for 60 min. The reaction was diluted with 0.5 mL of DMSO, filtered and purified by mass-directed HPLC using a gradient of 25-75% AcN/water both containing 0.1% TFA as the eluting solvent to afford 1-[4-((E)-2-Cyano-ethenesulfonyl)-phenyl]-cyclopropanecarboxylic acid 4-fluoro-benzylamide (49 mg; 69%) as a white foam. LCMS (ESI): m/z=385 (M+H)+; 1H-NMR (DMSO-d6, 400 MHz) δ 8.23 (d, 1H, J=15.6 Hz), 7.87 (m, 2H), 7.66 (m, 3H), 7.20 (m, 2H), 7.11 (m, 2H), 6.90 (d, 1H, J=15.6 Hz), 4.18 (d, 2H, J=6.0 Hz), 1.42 (dd, 2H, J=4.2, 7.0 Hz), 1.08 (dd, 2H, J=4.2, 7.0 Hz). LCMS=385 (M+H).

Example 68

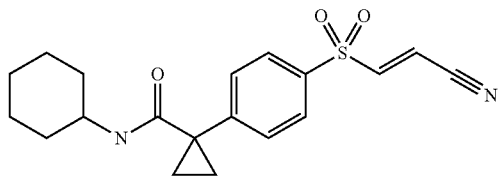 [SMILES: N#C/C=C/S(=O)(=O)c1ccc(C2(C(=O)NC3CCCCC3)CC2)cc1]

1-[4-((E)-2-Cyano-ethenesulfonyl)-phenyl]-cyclopropanecarboxylic acid cyclohexylamide 1-[4-((E)-2-Cyano-ethenesulfonyl)-phenyl]-cyclopropanecarboxylic acid (37 mg, 0.13 mmol), cyclohexanamine (18 uL, 0.16 mmol), N-(3-Dimethylaminopropyl)-N'-ethylcarbodiimide hydrochloride (32 mg, 0.17 mmol) and 1-Hydroxybenzotriazole (23 mg, 0.17 mmol) were combined in acetonitrile (1.0 mL) and the reaction mixture was allowed to stir at room temperature for 60 min. The reaction was diluted with 0.3 mL of DMSO, filtered and purified by mass-directed HPLC using a gradient of 25-75% MeCN/water both containing 0.1% TFA as the eluting solvent to afford 1-[4-((E)-2-Cyano-ethenesulfonyl)-phenyl]-cyclopropanecarboxylic acid cyclohexylamide (26 mg; 54%) as a white foam. LCMS (ESI): m/z=359 (M+H)+; 1H-NMR (DMSO-d6, 400 MHz) δ 8.23 (d, 1H, J=15.6 Hz), 7.84 (m, 2H), 7.59 (m, 2H), 7.20 (d, 1H, J=8.1 Hz), 6.90 (d, 1H, J=15.6 Hz), 3.54 (m, 1H), 1.63 (m, 4H), 1.53 (m, 1H), 1.37 (dd, 2H, J=4.4, 7.0 Hz), 1.05 (dd, 2H, J=4.4, 7.0 Hz), 1.02 (m, 1H). LCMS=359 (M+H).

Example 69

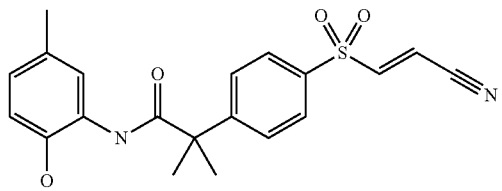 [SMILES: Cc1ccc(O)c(NC(=O)C(C)(C)c2ccc(S(=O)(=O)/C=C/C#N)cc2)c1]

2-[4-((E)-2-Cyano-ethenesulfonyl)-phenyl]-N-(2-hydroxy-5-methyl-phenyl)-isobutyramide 2-[4-((E)-2-Cyano-ethenesulfonyl)-phenyl]-2-methyl-propionic acid (256 mg, 0.916 mmol), 2-Amino-4-methyl-phenol (0.133 g, 1.08 mmol), N-(3-Dimethylaminopropyl)-N'-ethylcarbodiimide hydrochloride (221 mg, 1.15 mmol) and 1-Hydroxybenzotriazole (124 mg, 0.916 mmol) were dissolved in acetonitrile (7.0 mL) and the reaction mixture was allowed to stir at room temperature for 48 h. The reaction was concentrated to ca. 1 mL, then diluted with DMSO and purified by mass-directed HPLC (25-75% MeCN:water, both containing 0.1% TFA). 2-[4-((E)-2-Cyano-ethenesulfonyl)-phenyl]-N-(2-hydroxy-5-methyl-phenyl)-isobutyramide (78 mg; 22%) was isolated as beige lyophilate. LCMS (ESI): m/z=385 (M+H)+; 1H-NMR (DMSO-d6, 400 MHz) δ 9.42 (s, 1H), 8.30 (s, 1H), 8.24 (d, 1H, J=15.7 Hz), 7.91 (d, 2H, J=8.7 Hz), 7.76 (d, 2H, J=8.7 Hz), 7.53 (s, 1H), 6.91 (d, 1H, J=15.7 Hz), 6.74 (dd, 1H, J=2.5, 8.1 Hz), 6.70 (d, 1H, J=8.1 Hz), 2.17 (s, 3H), 1.62 (s, 6H).

Example 70

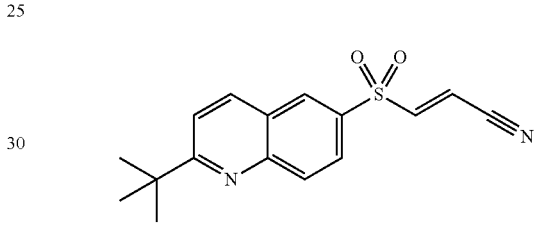

(E)-3-(2-tert-Butyl-quinoline-6-sulfonyl)-acrylonitrile a) Potassium hydroxide (0.322 g, 5.74 mmol) and Water (1.3 mL) were added to a mixture of 2-Amino-5-bromo-benzaldehyde (0.933 g, 4.66 mmol) and 3,3-Dimethyl-2-butanone (0.700 mL, 5.60 mmol) at room temperature. After 5 min, the mixture was heated at reflux for 3 h. The mixture was diluted with water (40 mL) then extracted with DCM (40 mL, 2×20 mL). The organic extract was washed with brine (20 mL), dried over sodium sulfate, filtered and concentrated in vacuo. The residue was purified (DCM load onto 24 g loading cartridge, then ISCO 40 g, 0-20% Ethyl acetate:hexanes) to afford 6-Bromo-2-tert-butyl-quinoline (0.97 g; 64%) as a yellow oil with small crystals forming.

b) To a solution of 6-bromo-2-tert-butylquinoline (1 g, 3.8 mmol) in anhydrous THF (50 ml) under nitrogen at −80° C. (ether/dry ice), was added slowly n-BuLi (2.5 M in hexane) (2 mL, 4.94 mmol). A cloudy suspension was slowly formed. Twenty minutes after BuLi addition, a stream of sulfur dioxide was bubbled through the mixture for 15 min. The reaction mixture was then allowed to warm up to room temperature, the solvent was removed under reduced pressure. The sulfinate residue was dissolved in water (10 ml), acetic acid (5 ml), and MeOH (15 ml), followed by addition of 2-chloroacrylonitrile (0.54 g, 6.23 mmol). The resulting mixture was stirred at room temperature overnight. The organic solvents were removed and the residue was diluted with 20 ml of water. The solution was adjusted to pH5-6 with sat. $K_2HPO_4$ aq. solution, then extracted with dichloromethane (2×50 ml) and dried over MgSO4. After filtration, the filtrate was stirred with triethylamine (1.16 mL, 8.3 mmol) for 1 h. The solution was washed with 10% aq citric acid and brine, and then dried over MgSO4. The final product was purified by flash column chromatography (silica gel, dichloromethane/Ethyl acetate, gradient) to give (E)-3-(2-tert-Butyl-quinoline-6-sulfonyl)-acrylonitrile (0.68 g, 59%) as a white solid. LCMS (ESI): m/z=301 (M+H)+; 1H-NMR (DMSO-d6, 400 MHz) δ 8.68 (d, 1H, J=2.1 Hz), 8.61 (d, 1H, J=8.8 Hz), 8.30 (d, 1H, J=15.7 Hz), 8.21 (d, 1H, J=8.9H), 8.07 (dd, 1H, J=2.2, 8.9 Hz), 7.92 (d, 1H, J=8.8 Hz), 6.96 (d, 1H, J=15.7 Hz), 1.43 (s, 9H).

Example 71

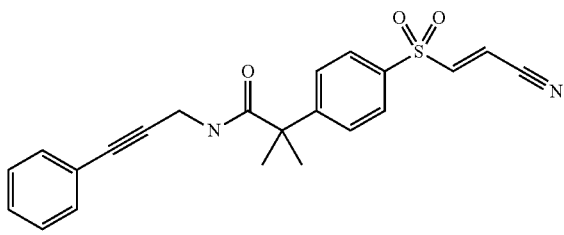 [SMILES: CC(C)(C(=O)NCC#Cc1ccccc1)c1ccc(S(=O)(=O)/C=C/C#N)cc1]

2-[4-((E)-2-Cyano-ethenesulfonyl)-phenyl]-N-(3-phenyl-prop-2-ynyl)-isobutyramide 2-[4-((E)-2-Cyano-ethenesulfonyl)-phenyl]-2-methyl-propionic acid (0.254 g, 0.909 mmol), 3-Phenyl-prop-2-ynylamine hydrochloride (0.272 g, 1.62 mmol), N-(3-Dimethylaminopropyl)-N'-ethylcarbodiimide hydrochloride (0.225 g, 1.18 mmol) and 1-Hydroxybenzotriazole (0.019 g, 0.14 mmol) were combined in acetonitrile (6.0 mL). After 1 h, 4-Methylmorpholine (0.100 mL, 0.909 mmol) was added, due to only trace conversion to the amide. After 4 h, the mixture was concentrated in vacuo to ~1 mL, DMSO was added (1 mL) and the mixture was filtered. Purification of the filtrate by preparative mass-directed HPLC (25-75% MeCN:water, both containing 0.1% TFA) afforded 2-[4-((E)-2-Cyano-ethenesulfonyl)-phenyl]-N-(3-phenyl-prop-2-ynyl)-isobutyramide (165 mg; 46%) after partial evaporation in vacuo followed by lyophilization. LCMS (ESI): m/z=393 (M+H)+; 1H-NMR (DMSO-d6, 400 MHz) δ 8.22 (d, 1H, J=15.6 Hz), 8.08 (t, 1H, J=5.5 Hz), 7.86 (d, 2H, J=8.7 Hz), 7.64 (d, 2H, J=8.7 Hz), 7.37 (m, 5H), 6.90 (d, 1H, J=15.6 Hz), 4.08 (d, 2H, J=5.5 Hz), 1.51 (s, 6H).

Example 72

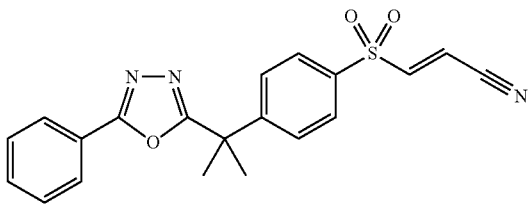 [SMILES: CC(C)(c1ccc(S(=O)(=O)/C=C/C#N)cc1)c1nnc(-c2ccccc2)o1]

(E)-3-{4-[1-Methyl-1-(5-phenyl-[1,3,4]oxadiazol-2-yl)-ethyl]-benzenesulfonyl}-acrylonitrile a) 2-[4-((E)-2-Cyano-ethenesulfonyl)-phenyl]-2-methyl-propionic acid (0.262 g, 0.938 mmol), Benzhydrazide (0.160 g, 1.17 mmol), N-(3-Dimethylaminopropyl)-N'-ethylcarbodiimide hydrochloride (0.232 g, 1.21 mmol) and 1-Hydroxybenzotriazole (0.019 g, 0.14 mmol) were dissolved in acetonitrile (6.0 mL) and the reaction mixture was allowed to stir at room temperature for 4 h. The mixture was poured into Ethyl acetate (60 mL), washed with 1N HCl (20 mL) and brine (20 mL), dried over sodium sulfate, filtered and concentrated in vacuo. Benzoic acid N'-{2-[4-((E)-2-cyano-ethenesulfonyl)-phenyl]-2-methyl-propionyl}-hydrazide was used in the next step without purification.

b) Benzoic acid N'-{2-[4-((E)-2-cyano-ethenesulfonyl)-phenyl]-2-methyl-propionyl}-hydrazide (324 mg, 0.815 mmol) was dissolved in 1,4-Dioxane (12.0 mL) and Phosphoryl chloride (0.500 mL, 5.36 mmol) was added and the mixture was heated at 90° C. for 2 h, then cooled to room temperature and diluted with Ethyl acetate (50 mL). The mixture was washed with satd. NaHCO3 (25 mL) and brine (10 mL), dried over sodium sulfate, filtered and concentrated in vacuo. The residue was dissolved in DCM and applied to an ISCO cartridge (5 g) and purified (ISCO 24 g, 0-50% Ethyl acetate:hexanes) to afford a foam after concentration of product containing fractions. This foam was dissolved in MeCN and water, and then lyophilized to give (E)-3-{4-[1-Methyl-1-(5-phenyl-[1,3,4]oxadiazol-2-yl)-ethyl]-benzenesulfonyl}-acrylonitrile as a white solid (223 mg, 72%). LCMS (ESI): m/z=380 (M+H)+; 1H-NMR (DMSO-d6, 400 MHz) δ 8.22 (d, 1H, J=15.7 Hz), 7.97 (m, 2H), 7.90 (d, 2H, J=8.7 Hz), 7.70 (d, 2H, J=8.7 Hz), 7.55-7.65 (m, 3H), 6.91 (d, 1H, J=15.7 Hz), 1.86 (s, 6H); $^{13}$C-NMR (DMSO-d$_6$, 100 MHz) δ 170.5, 164.5, 151.6, 149.0, 136.2, 132.0, 129.4, 128.6, 127.5, 126.6, 123.3, 114.5, 112.3, 40.2, 27.1

Example 73

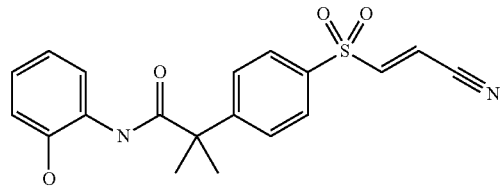 [SMILES: CC(C)(C(=O)Nc1ccccc1O)c1ccc(S(=O)(=O)/C=C/C#N)cc1]

2-[4-((E)-2-Cyano-ethenesulfonyl)-phenyl]-N-(2-hydroxy-phenyl)-isobutyramide

2-[4-((E)-2-Cyano-ethenesulfonyl)-phenyl]-2-methyl-propionic acid (0.336 g, 1.20 mmol), 2-aminophenol (0.234 g, 2.14 mmol), N-(3-Dimethylaminopropyl)-N'-ethylcarbodiimide hydrochloride (0.298 g, 1.56 mmol) and 1-Hydroxybenzotriazole (0.162 g, 1.20 mmol) were dissolved in acetonitrile (11.1 mL) and the reaction mixture was allowed to stir at room temperature for 20 h. The mixture was poured into Ethyl acetate (200 mL), washed with 1N HCl (25 mL) and brine (50 mL), dried over sodium sulfate, filtered and concentrated in vacuo. The residue was applied to an ISCO loading cartridge (24 g) as a DCM solution and purified on silica gel (ISCO 40 g, 5-50% Ethyl acetate:hexanes) to give 2-[4-((E)-2-Cyano-ethenesulfonyl)-phenyl]-N-(2-hydroxy-phenyl)-isobutyramide as an off-white solid (213 mg, 48%). LCMS (ESI): m/z=371 (M+H)+; 1H-NMR (DMSO-d6, 400 MHz) δ 9.70 (s, 1H), 8.32 (s, 1H), 8.24 (d, 1H, J=15.7 Hz), 7.91 (d, 2H, J=8.6 Hz), 7.77 (d, 2H, J=8.6 Hz), 7.70 (dd, 1H, J=1.5, 8.0 Hz), 6.88-6.96 (m, 2H), 6.82 (dd, 1H, J=1.5, 8.0 Hz), 6.75 (dd, 1H, J=1.2 Hz, 7.5 Hz), 1.62 (s, 6H).

Example 74

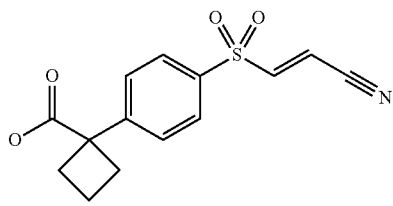 [SMILES: N#C/C=C/S(=O)(=O)c1ccc(C2(C(=O)O)CCC2)cc1]

1-[4-((E)-2-Cyano-ethenesulfonyl)-phenyl]-cyclobutanecarboxylic acid

To a solution of 1-(4-bromophenyl)cyclobutanecarboxylic acid (5.1 g, 20 mmol) in anhydrous THF (150 ml) under nitrogen at −80° C. (ether/dry ice), was added slowly Phenyl lithium in toluene 1.8 M (13.9 mL, 25 mmol). After 5 min, to this mixture, n-BuLi (2.5 M in hexane) (10.4 mL, 26 mmol) was added. A cloudy suspension was slowly formed. Twenty minutes after BuLi addition, a stream of sulfur dioxide was bubbled through the mixture for 15 min. The reaction mixture was then allowed to warm up to room temperature and the solvent was removed in vacuo. The sulfinate residue was dissolved in water (30 ml), acetic acid (16 ml), and MeOH (40 ml), followed by addition of 2-chloroacrylonitrile (2.6 g, 30 mmol). The resulting mixture was stirred at room temperature overnight. The organic solvents were removed and the residue was diluted with 20 ml of water. The solution was adjusted to pH5-6 with sat. K$_2$HPO$_4$ aq. solution, then extracted with dichloromethane (2×100 ml), dried over MgSO4. After filtration, the filtrate was stirred with triethylamine (5.6 mL, 40 mmol) for 1 h. The solution was washed with 10% aq citric acid and brine, dried over MgSO4. The final product was purified by flash column chromatography (silica gel, dichloromethane/Ethyl acetate, gradient) to give 1-[4-((E)-2-Cyano-ethenesulfonyl)-phenyl]-cyclobutanecarboxylic acid (1.52 g, 26%) as a white solid. LCMS (ESI): m/z=246 (M-CO2H)+; 1H-NMR (DMSO-d6, 400 MHz) δ 12.66 (s, 1H), 8.23 (d, 1H, J=15.7 Hz), 7.88 (d, 2H, J=8.5 Hz), 7.58 (d, 2H, J=8.5 Hz), 6.91 (d, 1H, J=15.7 Hz), 2.75 (m, 2H), 2.45 (m, 2H), 2.01 (m, 1H), 1.81 (m, 1H); $^{13}$C-NMR (DMSO-d$_6$, 100 MHz) δ 175.5, 151.4, 149.1, 135.5, 128.2, 127.8, 114.6, 112.0, 52.0, 31.8, 16.1.

Example 75

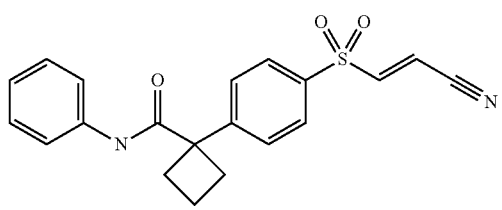 [SMILES: N#C/C=C/S(=O)(=O)c1ccc(C2(C(=O)Nc3ccccc3)CCC2)cc1]

1-[4-((E)-2-Cyano-ethenesulfonyl)-phenyl]-cyclobutanecarboxylic acid phenylamide 1-[4-((E)-2-Cyano-ethenesulfonyl)-phenyl]-cyclobutanecarboxylic acid (58 mg, 0.20 mmol), 1-Hydroxybenzotriazole (6 mg, 0.04 mmol), N-(3-Dimethylaminopropyl)-N'-ethylcarbodiimide hydrochloride (51 mg, 0.27 mmol) and aniline (21 uL, 0.23 mmol) in acetonitrile (0.5 mL) were stirred in a vial at room temperature for 1 h. The mixture was diluted with DMSO (0.2 mL), filtered and purified by mass-directed HPLC to afford 1-[4-((E)-2-Cyano-ethenesulfonyl)-phenyl]-cyclobutanecarboxylic acid phenylamide (34 mg; 47%). LCMS (ESI): m/z=367 (M+H)+; 1H-NMR (DMSO-d6, 400 MHz) δ 9.55 (s, 1H), 8.20 (d, 1H, J=15.6 Hz), 7.91 (d, 2H, J=8.6 Hz), 7.77 (d, 2H, J=8.7 Hz), 7.58 (m, 2H), 7.27 (m, 2H), 7.02 (m, 1H), 6.90 (d, 1H, J=15.6 Hz), 2.90 (M, 2H), 2.53 (m, 2H), 1.86 (m, 2H); $^{13}$C-NMR (DMSO-d$_6$, 100 MHz) δ 172.6, 151.6, 149.1, 139.0, 135.5, 128.5, 128.3, 127.6, 123.5, 119.9, 114.6, 112.0, 54.1, 32.2, 15.7.

Example 76

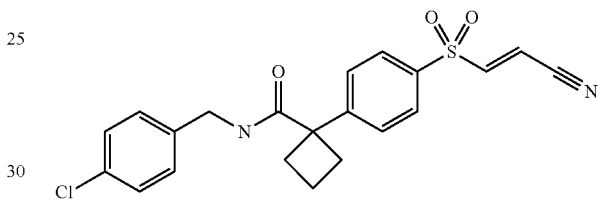

1-[4-((E)-2-Cyano-ethenesulfonyl)-phenyl]-cyclobutanecarboxylic acid 4-chloro-benzylamide 1-[4-((E)-2-Cyano-ethenesulfonyl)-phenyl]-cyclobutanecarboxylic acid (62 mg, 0.21 mmol), 1-Hydroxybenzotriazole (6 mg, 0.04 mmol), N-(3-Dimethylaminopropyl)-N'-ethylcarbodiimide hydrochloride (52 mg, 0.27 mmol) and p-Chlorobenzylamine (31 uL, 0.25 mmol) in acetonitrile (1.0 mL) were stirred in a vial at room temperature for 4 h. The mixture was concentrated in vacuo, diluted with DMSO (0.6 mL), filtered and purified by mass-directed HPLC to afford 1-[4-((E)-2-Cyano-ethenesulfonyl)-phenyl]-cyclobutanecarboxylic acid 4-chloro-benzylamide (44 mg; 50%). LCMS (ESI): m/z=367 (M+H)+; 1H-NMR (DMSO-d6, 400 MHz) δ 8.37 (t, 1H, J=6.0 Hz), 8.25 (d, 1H, J=15.8 Hz), 7.89 (d, 2H, J=8.5 Hz), 7.64 (d, 2H, J=8.5 Hz), 7.28 (d, 2H, J=8.5 Hz), 7.06 (d, 2H, J=8.5 Hz), 6.92 (d, 1H, J=15.8 Hz), 4.19 (d, 2H, J=6.0 Hz), 2.78 (M, 2H), 2.43 (m, 2H), 1.84 (m, 2H); $^{13}$C-NMR (DMSO-d$_6$, 100 MHz) δ 173.8, 152.2, 149.2, 138.7, 135.4, 131.1, 128.5, 128.13, 128.08, 127.5, 114.6, 112.0, 53.3, 41.7, 32.1, 16.0.

Example 77

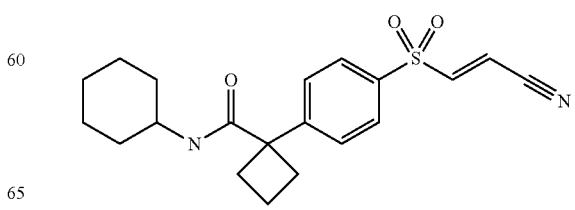

1-[4-((E)-2-Cyano-ethenesulfonyl)-phenyl]-cyclobutanecarboxylic acid cyclohexylamide 1-[4-((E)-2-Cyano-ethenesulfonyl)-phenyl]-cyclobutanecarboxylic acid (58 mg, 0.20 mmol), 1-Hydroxybenzotriazole (6 mg, 0.04 mmol), N-(3-Dimethylaminopropyl)-N'-ethylcarbodiimide hydrochloride (51 mg, 0.27 mmol) and cyclohexylamine (26 uL, 0.23 mmol) in acetonitrile (1.0 mL) were stirred in a vial at room temperature. After 5 h, the mixture was poured into Ethyl acetate, washed with 1N HCl, brine, dried over sodium sulfate, filtered and conc. The residue was purified to afford 1-[4-((E)-2-Cyano-ethenesulfonyl)-phenyl]-cyclobutanecarboxylic acid cyclohexylamide (32 mg; 43%). LCMS (ESI): m/z=373 (M+H)+; 1H-NMR (DMSO-d6, 400 MHz) δ 8.23 (d, 1H, J=15.6 Hz), 7.86 (d, 2H, J=8.5 Hz), 7.64 (d, 2H, J=8.5 Hz), 7.51 (d, 1H, J=8.0 Hz), 6.90 (d, 1H, J=15.6 Hz), 3.46 (m, 1H), 2.74 (M, 2H), 2.35 (m, 2H), 1.78 (m, 2H), 1.57 (m, 5H), 1.0-1.2 (m, 5H).

Example 78

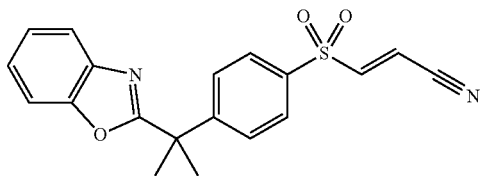 [SMILES: CC(C)(c1ccc(S(=O)(=O)/C=C/C#N)cc1)c1nc2ccccc2o1]

(E)-3-[4-(1-Benzoxazol-2-yl-1-methyl-ethyl)-benzenesulfonyl]-acrylonitrile

2-[4-((E)-2-Cyano-ethenesulfonyl)-phenyl]-N-(2-hydroxy-phenyl)-isobutyramide (99 mg, 0.27 mmol) and Methanesulfonic acid (0.50 mL, 7.7 mmol) were heated in 1,4-Dioxane (3.0 mL) in a vial at 90° C. for 24 h. The mixture was cooled to room temperature, partitioned between Ethyl acetate (60 mL) and satd. sodium bicarbonate (60 mL). After separation, the aqueous was extracted with Ethyl acetate (30 mL), then the combined organics were washed with brine (50 mL), dried over sodium sulfate, filtered and concentrated in vacuo. The residue was dissolved in DCM and applied to an ISCO cartridge (5 g) followed by purification by chromatography (ISCO 40 g, 0-40% Ethyl acetate:hexanes) to afford (E)-3-[4-(1-Benzoxazol-2-yl-1-methyl-ethyl)-benzenesulfonyl]-acrylonitrile as a white solid (55% yield). LCMS (ESI): m/z=353 (M+H)+; 1H-NMR (DMSO-d6, 400 MHz) δ 8.22 (d, 1H, J=15.6 Hz), 7.89 (d, 2H, J=8.7 Hz), 7.78 (m, 1H), 7.66 (m, 3H), 7.38 (m, 2H), 6.90 (d, 1H, J=15.6 Hz), 1.86 (s, 6H); 13C-NMR (DMSO-d6, 100 MHz) δ 170.2, 152.3, 150.4, 149.0, 140.4, 136.0, 128.5, 127.6, 125.2, 124.5, 119.8, 114.6, 112.2, 110.9, 41.9, 27.3.

Example 79

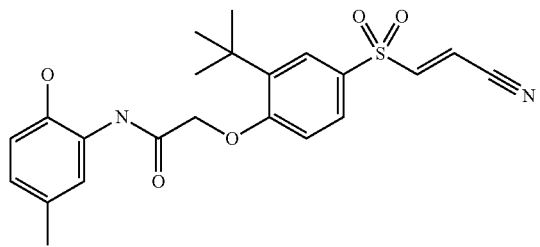 [SMILES: Cc1ccc(O)c(NC(=O)COc2ccc(S(=O)(=O)/C=C/C#N)cc2C(C)(C)C)c1]

2-[2-tert-Butyl-4-((E)-2-cyano-ethenesulfonyl)-phenoxy]-N-(2-hydroxy-5-methyl-phenyl)-acetamide

[2-tert-Butyl-4-((E)-2-cyano-ethenesulfonyl)-phenoxy]-acetic acid (186 mg, 0.575 mmol), N-(3-Dimethylaminopropyl)-N'-ethylcarbodiimide hydrochloride (138 mg, 0.719 mmol), 1-Hydroxybenzotriazole (85.5 mg, 0.633 mmol), and 2-Amino-4-methyl-phenol (0.142 g, 1.15 mmol) were combined in acetonitrile (6.0 mL) and stirred in a vial for 3 h. The mixture was then added to Ethyl acetate (100 mL) and washed with 1N HCl (15 mL) and brine (20 mL). The organics were dried over sodium sulfate, diluted with hexane (20 mL) and filtered through 4 mL silica gel (hexane bed), rinsing with 60 mL 1:1 Ethyl acetate:Hexane. The filtrate was concentrated in vacuo, dissolved in DCM and applied to an ISCO cartridge (5 g) and purified (ISCO 24 g, 0-50% Ethyl acetate:hexanes) to afford 2-[2-tert-Butyl-4-((E)-2-cyano-ethenesulfonyl)-phenoxy]-N-(2-hydroxy-5-methyl-phenyl)-acetamide (0.195 g; 79%). LCMS (ESI): m/z=429 (M+H)+; 1H-NMR (DMSO-d6, 400 MHz) δ 9.80 (s, 1H), 9.18 (s, 1H), 8.23 (d, 1H, J=15.6 Hz), 7.89 (s, 1H), 7.77 (dd, 1H, J=2.4, 8.7 Hz), 7.71 (d, 1H, J=2.4 Hz), 7.25 (d, 1H, J=8.7 Hz), 6.84 (d, 1H, J=15.6 Hz), 6.75 (m, 2H), 5.00 (s, 2H), 2.19 (s, 3H), 1.44 (s, 9H); 13C-NMR (DMSO-d6, 100 MHz) δ 165.2, 161.3, 149.7, 144.5, 139.0, 128.8, 128.7, 127.6, 126.5, 125.5, 124.7, 121.1, 114.7, 114.7, 113.7, 110.8, 67.5, 34.9, 29.2, 20.5.

Example 80

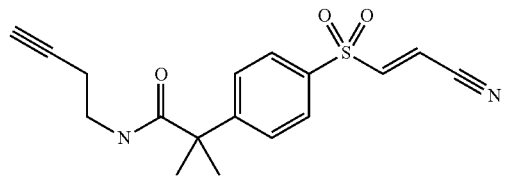 [SMILES: C#CCCNC(=O)C(C)(C)c1ccc(S(=O)(=O)/C=C/C#N)cc1]

N-But-3-ynyl-2-[4-((E)-2-cyano-ethenesulfonyl)-phenyl]-isobutyramide

2-[4-((E)-2-Cyano-ethenesulfonyl)-phenyl]-2-methyl-propionic acid (0.254 g, 0.909 mmol), But-3-yn-1-amine hydrochloride (0.171 g, 1.62 mmol), N-(3-Dimethylaminopropyl)-N'-ethylcarbodiimide hydrochloride (0.225 g, 1.18 mmol), 4-Methylmorpholine (0.100 mL, 0.909 mmol) and 1-Hydroxybenzotriazole (0.019 g, 0.14 mmol) were combined in Acetonitrile (6.0 mL). After 45 m, the mixture was concentrated in vacuo to ~1 mL, DMSO was added (1 mL) and the mixture was filtered. Purification of the filtrate by mass-directed HPLC (25-75% MeCN:water, 0.1% TFA) afforded N-But-3-ynyl-2-[4-((E)-2-cyano-ethenesulfonyl)-phenyl]-isobutyramide (48 mg, 16%). LCMS (ESI): m/z=331 (M+H)+; 1H-NMR (DMSO-d6, 400 MHz) δ 8.23 (d, 1H, J=15.7 Hz), 7.85 (d, 2H, J=8.7 Hz), 7.66 (t, 1H, J=5.7 Hz), 7.62 (d, 2H, J=8.7 Hz), 6.90 (d, 1H, J=15.7 Hz), 3.16 (m, 2H), 2.79 (t, 1H, J=2.7 Hz), 2.28 (dt, 2H, J=2.7, 7.1 Hz), 1.47 (s, 6H).

Example 81

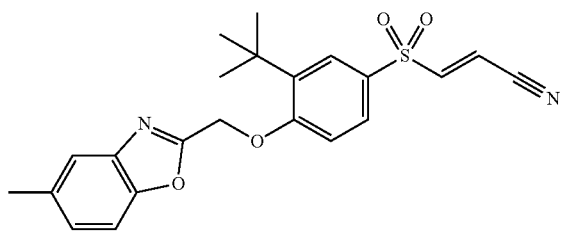 [SMILES: Cc1ccc2oc(COc3ccc(S(=O)(=O)/C=C/C#N)cc3C(C)(C)C)nc2c1]

(E)-3-[3-tert-Butyl-4-(5-methyl-benzoxazol-2-yl-methoxy)-benzenesulfonyl]-acrylonitrile 2-[2-tert-Butyl-4-((E)-2-cyano-ethenesulfonyl)-phenoxy]-N-(2-hydroxy-5-methyl-phenyl)-acetamide (0.178 g, 0.415 mmol) was heated in 1,4-Dioxane (6.0 mL) with methanesulfonic acid (1.0 mL, 15 mmol) at 90° C. for 8 h. The mixture was cooled to room temperature, stirred for 48 h, then was treated with additional methanesulfonic acid (1 mL) and heated for 3 h at 90° C. The mixture was cooled and added into Ethyl acetate (80 mL) and satd. NaHCO3 (40 mL). The layers were separated and the organics washed with brine (20 mL), dried over sodium sulfate, filtered and concentrated in vacuo. The residue was dissolved in DCM, applied to an ISCO cartridge (5 g) and purified (ISCO 40 g, 0-40% Ethyl acetate:hexanes) to afford (E)-3-[3-tert-Butyl-4-(5-methyl-benzoxazol-2-ylmethoxy)-benzenesulfonyl]-acrylonitrile (86 mg; 50%). LCMS (ESI): m/z=411 (M+H)+; 1H-NMR (DMSO-d6, 400 MHz) δ 8.23 (d, 1H, J=15.7 Hz), 7.80 (dd, 1H, J=2.4, 8.7 Hz), 7.72 (d, 1H, J=2.4 Hz), 7.64 (d, 1H, J=8.4 Hz), 7.61 (m, 1H), 7.46 (d, 1H, J=8.7 Hz), 7.26 (dd, 1H, J=1.2, 8.4 Hz), 6.85 (d, 1H, J=15.7 Hz), 5.67 (s, 2H), 2.43 (s, 3H), 1.39 (s, 9H).

Example 82

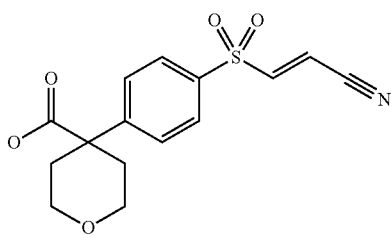 [SMILES: N#C/C=C/S(=O)(=O)c1ccc(C2(C(=O)O)CCOCC2)cc1]

4-[4-((E)-2-Cyano-ethenesulfonyl)-phenyl]-tetrahydro-pyran-4-carboxylic acid

To a solution of 1-(4-bromophenyl)tetrahydro-2H-pyran-4-carboxylic acid (2.85 g, 10 mmol) in anhydrous THF (100 ml) under nitrogen at −80° C. (ether/dry ice), was added slowly Phenyl lithium in toluene 1.8 M (7 mL, 12.5 mmol). After 5 min, to this mixture, n-BuLi (2.5 M in hexane) (5.2 mL, 13 mmol) was added. A cloudy suspension was slowly formed. Twenty minutes after BuLi addition, a stream of sulfur dioxide was bubbled through the mixture for 15 min. The reaction mixture was then allowed to warm up to room temperature and the solvent was removed in vacuo. The sulfinate residue was dissolved in water (15 ml), acetic acid (8 ml), and MeOH (20 ml), followed by addition of 2-chloroacrylonitrile (1.3 g, 15 mmol). The resulting mixture was stirred at room temperature overnight. The organic solvents were removed and the residue was diluted with 20 ml of water. The solution was adjusted to pH5-6 with sat. K$_2$HPO$_4$ aq. solution, then extracted with dichloromethane (2×50 ml), dried over MgSO4. After filtration, the filtrate was stirred with triethylamine (2.8 mL, 20 mmol) for 1 h. The solution was washed with 10% aq citric acid and brine, dried over MgSO4. The final product was purified by flash column chromatography (silica gel, dichloromethane/Ethyl acetate, gradient) to give 4-[4-((E)-2-Cyano-ethenesulfonyl)-phenyl]-tetrahydro-pyran-4-carboxylic acid (0.87 g, 27%) as a white solid. LCMS (ESI): m/z=276 (M-CO2H)+; 1H-NMR (DMSO-d6, 400 MHz) δ 13.00 (s, 1H), 8.23 (d, 1H, J=15.7 Hz), 7.91 (d, 2H, J=8.7 Hz), 7.74 (d, 2H, J=8.7 Hz), 6.92 (d, 1H, J=15.7 Hz), 3.82 (m, 2H), 3.48 (m, 2H), 2.40 (m, 2H), 1.88 (m, 2H); $^{13}$C-NMR (DMSO-d$_6$, 100 MHz) δ 174.3, 150.2, 149.0, 136.1, 128.4, 127.6, 114.6, 112.2, 64.6, 48.5, 33.7.

Example 83

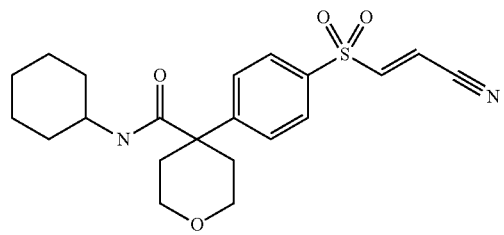 [SMILES: N#C/C=C/S(=O)(=O)c1ccc(C2(C(=O)NC3CCCCC3)CCOCC2)cc1]

4-[4-((E)-2-Cyano-ethenesulfonyl)-phenyl]-tetrahydro-pyran-4-carboxylic acid cyclohexylamide 4-[4-((E)-2-Cyano-ethenesulfonyl)-phenyl]-tetrahydro-pyran-4-carboxylic acid (61 mg, 0.19 mmol), cyclohexylamine (33 uL, 0.29 mmol), 1-Hydroxybenzotriazole (25.6 mg, 0.190 mmol) and N-(3-Dimethylaminopropyl)-N'-ethylcarbodiimide hydrochloride (46 mg, 0.24 mmol) were combined in acetonitrile (6.0 mL) and stirred at room temperature. After 4 h, the mixture was concentrated in vacuo, dissolved in DMSO and purified by mass-directed HPLC (25-75% MeCN:water, 0.1% TFA) to give 4-[4-((E)-2-Cyano-ethenesulfonyl)-phenyl]-tetrahydro-pyran-4-carboxylic acid cyclohexylamide (39 mg, 51%). LCMS (ESI): m/z=403 (M+H)+; 1H-NMR (DMSO-d6, 400 MHz) δ 8.23 (d, 1H, J=15.6 Hz), 7.87 (d, 2H, J=8.6 Hz), 7.66 (d, 2H, J=8.6 Hz), 7.45 (d, 1H, 8.0 Hz), 6.91 (d, 1H, J=15.7 Hz), 3.77 (m, 2H), 3.56 (m, 1H), 3.44 (m, 2H), 1.83 (m, 2H), 1.62 (m, 6H), 1.12 (m, 6H).

Example 84

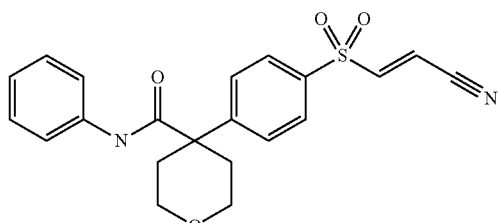

4-[4-((E)-2-Cyano-ethenesulfonyl)-phenyl]-tetrahydro-pyran-4-carboxylic acid phenylamide 4-[4-((E)-2-Cyano-ethenesulfonyl)-phenyl]-tetrahydro-pyran-4-carboxylic acid (67 mg, 0.21 mmol), aniline (29 uL, 0.32 mmol), 1-Hydroxybenzotriazole (7.0 mg, 0.052 mmol) and N-(3-Dimethylaminopropyl)-N'-ethylcarbodiimide hydrochloride (50.0 mg, 0.261 mmol) were combined in acetonitrile (3.00 mL) and stirred at room temperature. After 24 h, the mixture was concentrated in vacuo, dissolved in DMSO and purified by mass-directed HPLC (25-75% MeCN:water, 0.1% TFA) to give 4-[4-((E)-2-Cyano-ethenesulfonyl)-phenyl]-tetrahydro-pyran-4-carboxylic acid phenylamide (23 mg, 28%). LCMS (ESI): m/z=397 (M+H)+; 1H-NMR (DMSO-d6, 400 MHz) δ 9.38 (s, 1H), 8.22 (d, 1H, J=15.7 Hz), 7.93 (d, 2H, J=8.7 Hz), 7.76 (d, 2H, J=8.7 Hz), 7.54 (m, 2H), 7.28 (m, 2H), 7.06 (m, 1H), 6.91 (d, 1H, J=15.7 Hz), 3.81 (m, 2H), 3.55 (m, 2H), 2.60 (m, 2H), 2.00 (m, 2H).

Example 85

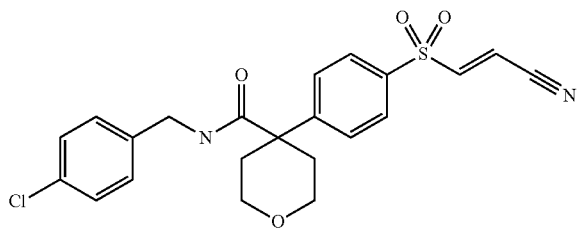 [SMILES: N#C/C=C/S(=O)(=O)c1ccc(C2(C(=O)NCc3ccc(Cl)cc3)CCOCC2)cc1]

4-[4-((E)-2-Cyano-ethenesulfonyl)-phenyl]-tetrahydro-pyran-4-carboxylic acid 4-chloro-benzylamide 4-[4-((E)-2-Cyano-ethenesulfonyl)-phenyl]-tetrahydropyran-4-carboxylic acid (72 mg, 0.22 mmol), p-Chlorobenzylamine (45 uL, 0.37 mmol), 1-Hydroxybenzotriazole (9.0 mg, 0.067 mmol) and N-(3-Dimethylaminopropyl)-N'-ethylcarbodiimide hydrochloride (57 mg, 0.30 mmol) were combined in acetonitrile (6.0 mL, 110 mmol) and stirred at room temperature. After 2 h, the mixture was concentrated in vacuo, dissolved in DMSO and purified by mass-directed HPLC (25-75% MeCN:water, 0.1% TFA) to give 4-[4-((E)- 2-Cyano-ethenesulfonyl)-phenyl]-tetrahydro-pyran-4-carboxylic acid 4-chloro-benzylamide (32 mg 32%). LCMS (ESI): m/z=445 (M+H)+; 1H-NMR (DMSO-d6, 400 MHz) δ 8.36 (t, 1H, J=5.9 Hz), 8.26 (d, 1H, J=15.6 Hz), 7.90 (d, 2H, J=8.6 Hz), 7.69 (d, 2H, J=8.6 Hz), 7.27 (d, 2H, J=8.4 Hz), 7.03 (d, 2H, J=8.4 Hz), 6.93 (d, 1H, J=15.6 Hz), 4.21 (d, 2H, J=5.9 Hz), 3.76 (m, 2H), 3.46 (m, 2H), 2.52 (m, 2H), 1.90 (m, 2H).

Example 86

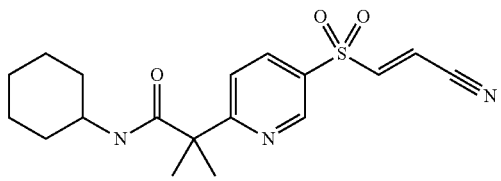 [SMILES: CC(C)(C(=O)NC1CCCCC1)c1ccc(S(=O)(=O)/C=C/C#N)cn1]

2-[5-((E)-2-Cyano-ethenesulfonyl)-pyridin-2-yl]-N-cyclohexyl-isobutyramide a) To a suspension of 2-(5-bromopyridin-2-yl)-2-methylpropanoic acid (1.22 g, 5 mmol) in 25 mL of DMF was added TEA (2.1 mL, 15 mmol) and cyclohexylamine (0.86 mL, 7.5 mmol) and followed by propylphosphonic anhydride (50% solution in DMF) (8.9 mL, 15 mmol) at room temperature under nitrogen. The resulting mixture was stirred at room temperature for 2 h. The mixture was concentrated in vacuo, dissolved in DCM (100 mL) and brine (50 mL), separated and the organic phase was concentrated in vacuo. The crude product was purified by flash column chromatography (silica gel, dichloromethane/Acetone, gradient) to give 2-(5-Bromo-pyridin-2-yl)-N-cyclohexyl-isobutyramide (0.83 g, 51%) as a white solid.

b) To a solution of 2-(5-Bromo-pyridin-2-yl)-N-cyclohexyl-isobutyramide (0.8 g, 3.3 mmol) in anhydrous THF (100 ml) under nitrogen at −80° C. (ether/dry ice), was added slowly Phenyl lithium in toluene 1.8 M (2.3 mL, 4.1 mmol). After 5 min, to this mixture, n-BuLi (2.5 M in hexane) (1.7 mL, 4.3 mmol) was added. A cloudy suspension was slowly formed. Twenty minutes after BuLi addition, a stream of sulfur dioxide was bubbled through the mixture for 10 min. The reaction mixture was then allowed to warm up to room temperature and the solvent was removed in vacuo. The sulfinate residue was dissolved in water (10 ml), acetic acid (5 ml), and MeOH (15 ml), followed by addition of 2-chloroacrylonitrile (0.43 g, 5.0 mmol). The resulting mixture was stirred at room temperature overnight. The organic solvents were removed and the residue was diluted with 20 ml of water. The solution was adjusted to pH5-6 with sat. K2HPO4 aq. solution, then extracted with dichloromethane (2×30 ml) and dried over MgSO4. After filtration, the filtrate was stirred with triethylamine (0.92 mL, 6.6 mmol) for 1 h. The solution was washed with 10% aq citric acid and brine, then dried over MgSO4. The final product was purified by flash column chromatography (silica gel, dichloromethane/Ethyl acetate, gradient) to give 2-[5-((E)-2-Cyano-ethenesulfonyl)-pyridin-2-yl]-N-cyclohexyl-isobutyramide (182 mg, 15%) as a white solid. LCMS (ESI): m/z=362 (M+H)+; 1H-NMR (DMSO-d6, 400 MHz) δ 8.97 (dd, 1H, J=0.6, 2.4 Hz), 8.28 (d, 1H, J=15.7 Hz), 8.24 (dd, 1H, J=2.4, 8.5 Hz), 7.62 (dd, 1H, J=0.6, 8.5 Hz), 7.22 (d, 1H, J=8.0 Hz), 6.97 (d, 1H, J=15.7 Hz), 3.55 (m, 1H), 1.66 (m, 4H), 1.53 (m, 1H), 1.49 (s, 6H), 1.0-1.2 (m, 5H).

Cell Cultures and Transfection.

BxPc-3 and Su.86.86 pancreatic and HT-29 colon and A2780 ovarian cancer cell lines were purchased from ATCC and cultured in DMEM supplemented with 10% fetal bovine serum, glutamine, penicillin, and streptomycin. All cells were cultured at 37° C. in a humidified incubator in a 5% $CO_2$ atmosphere. The cancer cell lines were transduced with a retrovirus containing pLuc-puro, a constitutive luciferase reporter and selected in G418-containing media. Transient transfection of a full-length human c-FLIP construct in the vector pcDNA3 was performed as previously described. Scaife et al. Cancer Research 2002, 62: 6870-78.

Cell Survival and Adhesion Assay.

Pancreatic cancer cell cultures (BxPc-3 and Su.86.86) and colon cancer (HT-29) and ovarian cancer (A2780) cells that were stably transfected with a firefly luciferase construct were transiently suspended with trypsin-PBS. $10^5$ cells were overlayed onto confluent monolayers of human mesothelial cells in 96-well plates while simultaneously adding various concentrations of compounds of the invention or DMSO for 5 hours. The non-adherent cells were carefully washed away from the wells twice with 100 μl/well of blocking buffer (1% BSA in PBS) and twice again with ice-cold PBS. Adherent and surviving cells were detected by luciferase activity in a luminometer as follows. The cells were lysed in 0.1% TritonX-100, 25 mM Gly-Gly (7.8), $MgSO_4$, 4 mM EGTA, 1 mM DTT. The total protein concentration was normalized with lysis buffer. 50 μl of cell lysate was added per well of a 96-well microtiter plate. 50 μl of luciferin substrate (Promega) was added per well and then the light output determined in a luminometer. Results for compounds of the present invention at a concentration of 10 μM are shown in Table I.

Athymic Mouse Cancer Studies.

The animal studies were approved by and performed in accordance with the University of Utah and University of Hawaii Institutional Animal Care and Use Committee. Athymic 5-week-old female nu/nu mice were randomized to intraperitoneal (IP) treatment with either compounds of the invention (5 mg/kg) or an equal volume of vehicle (DMSO) 4 hours prior to IP injection of $10^6$ suspended Su.86.86, BxPc-3, or HT-29 cells, or FLIP-high (CD133+). The mice continued to receive DMSO or compounds of the invention (5 mg/kg) IP every 3 days for 8-9 days. A mixture of 10 μl/gm of firefly D-luciferin (15 mg/ml stock) (Xenogen), 200 μl (stock=100 mg/ml) ketamine HCl, and 20 μl xylazine (stock=100 mg/ml) in pH 7.4 PBS was injected IP just prior to bioluminescent imaging in order to anesthetize the mice and provide substrate for the luciferase expressing cancer cells. The mice were euthanized and the abdominal cavity exposed surgically. The peritoneal tumor implants were imaged with the Xenogen bioluminescent imaging system. The tumor implants for each mouse were verified with a dissecting zoom microscope and histopathology.

REFERENCES

Burns, T. F., and El-Deiry, W. S. (2001). Identification of inhibitors of TRAIL-induced death (ITIDs) in the TRAIL-sensitive colon carcinoma cell line SW480 using a genetic approach. J Biol Chem 276, 37879-37886.

De Vita, V. T., Hellman, S., and Rosenberg, S. A. (2001). Cancer: Principles and Practice of Oncology, 5 edn (Philadelphia: Lippincott Williams and Wilkins).

Elnemr, A., Ohta, T., Yachie, A., Kayahara, M., Kitagawa, H., Fujimura, T., Ninomiya, I., Fushida, S., Nishimura, G. I., Shimizu, K., and Miwa, K. (2001). Human pancreatic cancer cells disable function of Fas receptors at several levels in Fas signal transduction pathway. Int J Oncol 18, 311-316.

Fujiwara, K. (2000). Intraperitoneal chemotherapy and intraperitoneal washing cytology in management of ovarian cancer. Gan To Kagaku Ryoho 27 *Suppl* 2, 354-358.

Johnstone, P. A., and Sindelar, W. F. (1993). Patterns of disease recurrence following definitive therapy of adenocarcinoma of the pancreas using surgery and adjuvant radiotherapy:correlations of a clinical trial. Int J Radiat Oncol Biol Phys 27, 831-834.

Kanellos, I., Demetriades, H., Zintzaras, E., Mandrali, A., Mantzoros, I., and Betsis, D. (2003). Incidence and prognostic value of positive peritoneal cytology in colorectal cancer. Dis Colon Rectum 46, 535-539.

Nakatsuka, A., Yamaguchi, K., Shimizu, S., Yokohata, K., Morisaki, T., Chijiiwa, K., and Tanaka, M. (1999). Positive washing cytology in patients with pancreatic cancer indicates a contraindication of pancreatectomy. Int J Surg Investig 1, 311-317.

Santala, M., Talvensaari-Mattila, A., and Kauppila, A. (2003). Peritoneal cytology and preoperative serum CA 125 level are important prognostic indicators of overall survival in advanced endometrial cancer. Anticancer Res 23, 3097-3103.

Terauchi, F., Moritake, T., Yamamoto, Y., and Ogura, H. (2002). Combination chemotherapy with paclitaxel and intraperitoneal cisplatin for ovarian cancer with disseminated lesions in the peritoneum and the diaphragm. Int J Clin Oncol 7, 356-360.

Yachida, S., Fukushima, N., Sakamoto, M., Matsuno, Y., Kosuge, T., and Hirohashi, S. (2002). Implications of peritoneal washing cytology in patients with potentially resectable pancreatic cancer. Br J Surg 89, 573-578.

Yu, W., Whang, I., Suh, I., Averbach, A., Chang, D., and Sugarbaker, P. H. (1998). Prospective randomized trial of early postoperative intraperitoneal chemotherapy as an adjuvant to resectable gastric cancer. Ann Surg 228, 347-354.

Zhang, L., and Fang, B. (2005). Mechanisms of resistance to TRAIL-induced apoptosis in cancer. Cancer Gene Ther 12, 228-237.

What is claimed is:

1. A compound of formula I, or a pharmaceutically acceptable salt form thereof,

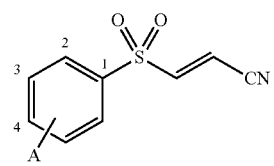

wherein A is at the 3- or 4-position of the phenyl ring; and A is

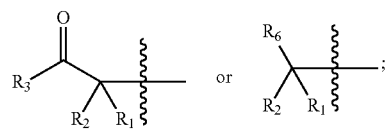

R$_1$ and R$_2$ are each independently substituted or unsubstituted alkyl or R$_1$ and R$_2$, together with the carbon atom to which they are attached, form a three- to seven-membered substituted or unsubstituted cycloalkyl ring;

R$_3$ is —OH, substituted or unsubstituted alkyl, substituted or unsubstituted cycloalkyl, substituted or unsubstituted cycloalkalkyl, substituted or unsubstituted alkoxy, substituted or unsubstituted aryl, substituted or unsubstituted heteroaryl, substituted or unsubstituted heterocycloalkyl, substituted or unsubstituted heterocycloalkalkyl, or —NR$_4$R$_5$;

R$_4$ and R$_5$ are each independently H, substituted or unsubstituted alkyl, substituted or unsubstituted alkyene oxide, substituted or unsubstituted cycloalkyl, substituted or unsubstituted heterocycloalkyl, substituted or unsubstituted aryl, substituted or unsubstituted aralkyl, substituted or unsubstituted heteroaryl, substituted or unsubstituted heteroaralkyl, —COOalkyl, —COalkyl, —COcycloalkyl, —NHCOalkyl, —NHCOaryl, or —NHCOcycloalkyl; or R$_4$ and R$_5$, together with the atoms through which they are attached, form a substituted or unsubstituted heterocycloalkyl ring; and R$_6$ is substituted or unsubstituted heteroaryl.

2. The compound of claim 1, wherein A is at the 4-position of the phenyl ring.

3. The compound of claim 1, wherein A is

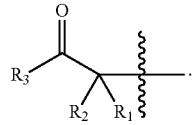

4. The compound of claim 1, wherein R$_1$ and R$_2$ are each —CH$_3$.

5. The compound of claim 3, wherein R$_3$ is —OH.

6. The compound of claim 3, wherein R$_3$ is substituted or unsubstituted heterocycloalkyl.

7. The compound of claim 3, wherein R$_3$ is —NR$_4$R$_5$.

8. The compound of claim 7, wherein R$_4$ is H.

9. The compound of claim 8, wherein R$_5$ is substituted or unsubstituted alkyl.

10. The compound of claim 8, wherein R$_5$ is substituted or unsubstituted aryl.

11. The compound of claim 8, wherein R$_5$ is substituted or unsubstituted aralkyl.

12. The compound of claim 8, wherein R$_5$ is substituted or unsubstituted heteroaryl.

13. The compound of claim 8, wherein R$_5$ is substituted or unsubstituted heteroaralkyl.

14. The compound of claim 8, wherein R$_5$ is substituted or unsubstituted cycloalkyl.

15. The compound of claim 8, wherein R$_5$ is substituted or unsubstituted heterocycloalkyl.

16. The compound of claim 8, wherein R$_5$ is substituted or unsubstituted alkyene oxide.

17. The compound of claim 8, wherein R$_5$ is —NHCOcycloalkyl.

18. The compound of claim 8, wherein R$_4$ and R$_5$, together with the atoms through which they are attached, form a substituted or unsubstituted heterocycloalkyl ring.

19. The compound of claim 3, wherein R$_3$ is —CH$_3$.

20. The compound of claim 19, wherein R$_5$ is substituted or unsubstituted alkyl.

21. The compound of claim 19, wherein R$_5$ is substituted or unsubstituted aryl.

22. The compound of claim 19, wherein R$_5$ is substituted or unsubstituted aralkyl.

23. The compound of claim 19, wherein R$_5$ is substituted or unsubstituted heteroaryl.

24. The compound of claim 19, wherein R$_5$ is substituted or unsubstituted heteroaralkyl.

25. The compound of claim 19, wherein R$_5$ is substituted or unsubstituted cycloalkyl.

26. The compound of claim 19, wherein R$_5$ is substituted or unsubstituted heterocycloalkyl.

27. The compound of claim 19, wherein R$_5$ is substituted or unsubstituted alkyene oxide.

28. The compound of claim 19, wherein R$_5$ is —NHCOcycloalkyl.

29. The compound of claim 19, wherein R$_4$ and R$_5$, together with the atoms through which they are attached, form a substituted or unsubstituted heterocycloalkyl ring.

30. The compound of claim 1, wherein A is

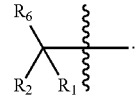

31. The compound of claim 30, wherein R$_1$ and R$_2$ are each —CH$_3$.

32. The compound of claim 30, wherein R$_6$ is substituted or unsubstituted oxadiazolyl.

33. The compound of claim 30, wherein R$_6$ is substituted or unsubstituted benzoimidazolyl.

34. The compound of claim 30, wherein R$_6$ is substituted or unsubstituted benzooxazolyl.

35. The compound of claim 30, wherein R$_6$ is substituted or unsubstituted oxazolyl.

36. A compound according to claim 1 which is:
2-[4-((E)-2-Cyano-ethenesulfonyl)-phenyl]-2-methyl-propionic acid;
2-[3-((E)-2-Cyano-ethenesulfonyl)-phenyl]-2-methyl-propionic acid;
(E)-3-[4-(1,1-Dimethyl-2-morpholin-4-yl-2-oxo-ethyl)-benzene sulfonyl]-acrylonitrile;
2-[4-((E)-2-Cyano-ethenesulfonyl)-phenyl]-N-(2-hydroxy-ethyl)-isobutyramide;
2-[4-((E)-2-Cyano-ethenesulfonyl)-phenyl]-N-phenyl-isobutyramide;
N-Benzyl-2-[4-((E)-2-cyano-ethenesulfonyl)-phenyl]-isobutyramide;
2-[4-((E)-2-Cyano-ethenesulfonyl)-phenyl]-N-pyridin-2-ylmethyl-isobutyramide;
2-[4-((E)-2-Cyano-ethenesulfonyl)-phenyl]-N-isobutyl-isobutyramide;
(E)-3-{4-[1,1-Dimethyl-2-(4-methyl-piperazin-1-yl)-2-oxo-ethyl]-benzenesulfonyl}-acrylonitrile;
2-[4-((E)-2-Cyano-ethenesulfonyl)-phenyl]-N-cyclopropylmethyl-isobutyramide;
2-[4-((E)-2-Cyano-ethenesulfonyl)-phenyl]-N-(2,2-difluoro-ethyl)-isobutyramide;
2-[4-((E)-2-Cyano-ethenesulfonyl)-phenyl]-N-cyclohexyl-isobutyramide;
2-[4-((E)-2-Cyano-ethenesulfonyl)-phenyl]-N(tetrahydro-pyran-4-yl)-isobutyramide;
N-(4-Chloro-benzyl)-2-[4-((E)-2-cyano-ethenesulfonyl)-phenyl]-isobutyramide;

2-[4-((E)-2-Cyano-ethenesulfonyl)-phenyl]-N-thiophen-2-ylmethyl-isobutyramide;
2-[4-((E)-2-Cyano-ethenesulfonyl)-phenyl]-N—((S)-1-phenyl-ethyl)-isobutyramide;
2-[4-((E)-2-Cyano-ethenesulfonyl)-phenyl]-N—((R)-1-phenyl-ethyl)-isobutyramide;
2-[4-((E)-2-Cyano-ethenesulfonyl)-phenyl]-N-(4-fluoro-benzyl)-isobutyramide;
2-[4-((E)-2-Cyano-ethenesulfonyl)-phenyl]-N-prop-2-ynyl-isobutyramide;
(E)-3-{4-[2-(3,4-Dihydro-1H-isoquinolin-2-yl)-1, 1-dimethyl-2-oxo-ethyl]-benzenesulfonyl}-acrylonitrile;
2-[4-((E)-2-Cyano-ethenesulfonyl)-phenyl-N-(4-pyrazol-1-yl-benzyl)-isobutyramide;
N-Benzyl-2-[4-((E)-2-cyano-ethenesulfonyl)-phenyl]-N-methyl-isobutyramide;
2-[4-((E)-2-Cyano-ethenesulfonyl)-phenyl]-N-(4-methoxy-phenyl)-isobutyramide;
2-[4-((E)-2-Cyano-ethenesulfonyl)-phenyl]-N-phenethyl-isobutyramide;
2-[4-((E)-2-Cyano-ethenesulfonyl)-phenyl]-N-(3-methoxy-phenyl)-isobutyramide;
2-[4-((E)-2-Cyano-ethenesulfonyl)-phenyl]-N-(4-sulfamoyl-benzyl)-isobutyramide;
(E)-3-[4-(1,1-Dimethyl-2-oxo-2-piperidin-1-yl-ethyl)-benzenesulfonyl]-acrylonitrile;
2-[4-((E)-2-Cyano-ethenesulfonyl)-phenyl]-N—((S)-2-hydroxy-1-phenyl-ethyl)-isobutyramide;
2-[4-((E)-2-Cyano-ethenesulfonyl)-phenyl]-N—((S)-2-oxo-azepan-3-yl)-isobytyramide;
2-[4-((E)-2-Cyano-ethenesulfonyl)-phenyl]-N-[4-(2-methoxy-ethoxymethyl)-phenyl]-isobutyramide;
(2-{2-[4-((E)-2-Cyano-ethenesulfonyl)-phenyl]-2-methyl-propionylamino}-ethyl)-carbamic acid tert-butyl ester;
(6-{2-[4-((E)-2-Cyano-ethenesulfonyl)-phenyl]-2-methyl-propionylamino}-hexyl)-carbamic acid tert-butyl ester;
{2-[2-(2-{2-[4-((E)-2-Cyano-ethenesulfonyl)-phenyl]-2-methyl-propionylamino}-ethoxy)-ethoxy]-ethyl}-carbamic acid tert-butyl ester;
2-[3-((E)-2-Cyano-ethenesulfonyl)-phenyl]-N-cyclohexyl isobutyramide;
2-[3-((E)-2-Cyano-ethenesulfonyl)-phenyl]-N-(3-methoxy-phenyl)-isobutyramide;
2-[3-((E)-2-Cyano-ethenesulfonyl)-phenyl]-N-(4-fluoro-benzyl)-isobutyramide;
N-(4-Amino-benzyl)-2-[4-((E)-2-cyano-ethenesulfonyl)-phenyl]-isobutyramide;
2-[4-((E)-2-Cyano-ethenesulfonyl)-phenyl]-N-(3-fluoro-benzyl)-isobutyramide;
2-[4-((E)-2-Cyano-ethenesulfonyl)-phenyl]-N-(2-fluoro-benzyl)-isobutyramide;
2-[4-((E)-2-Cyano-ethenesulfonyl)-phenyl]-N-(4-fluoro-benzyl)-N-methyl-isobutyamide;
2-[4-((E)-2-Cyano-ethenesulfonyl)-phenyl]-N-[3-(2-methoxy-ethoxy)-phenyl]-isobutyramide;
(3-{2-[4-((E)-2-Cyano-ethenesulfonyl)phenyl]-2-methyl-propionylamino}-phenoxy)-acetic acid;
2-[4-((E)-2-Cyano-ethenesulfonyl)-phenyl]-N-(3-methoxy-benzyl)-isobutyramide;
2-[4-((E)-2-Cyano-ethenesulfonyl)-phenyl]-N-(2-methoxy-benzyl)-isobutyramide;
2-[4-((E)-2-Cyano-ethenesulfonyl)-phenyl]-N-(2-methoxy-benzyl)-N-methyl-isobutyramide;
(E)-3-{4-[1-Methyl-1-(5-phenylamino-[1,3,4]oxadiazol-2-yl)-ethyl]-benzenesulfonyl}-acrylonitrile;
(E)-3-{4-[1-(5-Ethylamino-[1,3,4]oxadiazol-2-yl)-1-methyl-ethyl]-benzenesulfonyl}-acrylonitrile;
(E)-3-{4-[1-(1H-Benzimidazole-2-yl)-1-methyl-ethyl]-benzenesulfonyl}-acrylonitrile;
(E)-3-{4-[1-Methyl-1-(5-methyl-benzoxazol-2-yl)-ethyl]-benzenesulfonyl}-acrylonitrile;
(E)-3-{4-[1-Methyl-1-(5-methyl-oxazol-2-yl)-ethyl]-benzenesulfonyl}-acrylonitrile;
Cyclohexanecarboxylic acid N'-{2-[4-((E)-2-cyano-ethenesulfonyl)-phenyl]-2-methyl-propionyl}-hydrazide;
(E)-3-{4-[1-(5-Cyclohexyl-[1,3,4]oxadiazol-2-yl)-1-methyl-ethyl]-benzenesulfonyl}-acrylonitrile;
1-[4-((E)-2-Cyano-ethenesulfonyl)-phenyl]-cyclopropanecarboxylic acid;
(E)-3-{3-[1-Methyl-1-(5-methyl-benzoxazol-2-yl)-ethyl-benzenesulfonyl}-acrylonitrile; compound with trifluoro-acetic acid;
1-[4-((E)-2-Cyano-ethenesulfonyl)-phenyl]-cyclopropanecarboxylic acid 4-fluoro-benzylamide;
1-[4-((E)-2-Cyano-ethenesulfonyl)-phenyl]-cyclopropanecarboxylic acid cyclohexylamide;
2-[4-((E)-2-Cyano-ethenesulfonyl)-phenyl]-N-(2-hydroxy-5-methyl-phenyl)-isobutyramide;
2-[4-((E)-2-Cyano-ethenesulfonyl)-phenyl]-N-(3-phenyl-prop-2-ynyl)-isobutyramide;
(E)-3-{4-[1-Methyl-1-(5-phenyl)-[1,3,4]oxadiazol-2-yl)-ethyl]-benzenesulfonl}-acrylonitrile;
2-[4-((E)-2-Cyano-ethenesulfonyl)-phenyl]-N-(2-hydroxy-phenyl)-isobutyramide;
1-[4-((E)-2-Cyano-ethenesulfonyl)-phenyl]-cyclobutanecarboxylic acid;
1-[4-((E)-2-Cyano-ethenesulfonyl)-phenyl]-cyclobutanecarboxylic acid phenylamide;
1-[4-((E)-2-Cyano-ethenesulfonyl)-phenyl]-cyclobutanecarboxylic acid 4-chloro-benzylamide;
1-[4-((E)-2-Cyano-ethenesulfonyl)-phenyl]-cyclobutanecarboxylic acid cyclohexylamide;
(E)-3-{4-[1-Benzoxazol-2-yl-1-methyl-ethyl)-benzenesulfonyl]-acrylonitrile;
a pharmaceutically acceptable salt form thereof.

37. A pharmaceutical composition comprising a compound according to claim 1 or a pharmaceutically acceptable salt thereof, and a pharmaceutically acceptable carrier or diluent.

38. A method of treating or reducing the risk of peritoneal carcinomatosis in a patient that has had an intra-abdominal cancer removed, said method comprising administering to said patient a therapeutically effective amount of a pharmaceutical composition according to claim 37.

39. A method of treating or reducing the risk of peritoneal carcinomatosis in a patient that has had an intra-abdominal cancer removed, said method comprising administering to said patient a therapeutically effective amount of a compound according to claim 1 or a pharmaceutically acceptable salt thereof.

40. The method of claim 38 wherein the intra-abdominal cancer is located at or near the colon, at or near the ovary, at or near the rectum, at or near the stomach, or at or near the pancreas of the patient.

41. The method of claim 39 wherein the intra-abdominal cancer is located at or near the colon, at or near the ovary, at or near the rectum, at or near the stomach, or at or near the pancreas of the patient.

42. A method of treating or reducing the risk of peritoneal carcinomatosis in a patient that has had an intra-abdominal cancer removed, said method comprising administering to said patient a therapeutically effective amount of a compound selected from:

(E)-3-(4-tert-Butyl-benzenesulfonyl)-acrylamide;
1-tert-butyl-4-[((E)-prop-1-ene)-1-sulfonyl]-benzene;
1-tert-butyl-4-((E)-2-phenyl-ethenesulfonyl)-benzene;
1-tert-butyl-4-(1-phenyl-ethenesulfonyl)-benzene;
(E)-3-(4-tert-Butyl-benzenesulfonyl)-acrylic acid ethyl ester;
(E)-3-(4-tert-butyl-phenylsulfanyl)-acrylonitrile;
[2-tert-Butyl-4-((E)-2-cyano-ethenesulfonyl)-phenoxy]-acetic acid;
2-[2-tert-Butyl-4-((E)-2-cyano-ethenesulfonyl)-phenoxy]-N-cyclohexylacetamide;
2-[2-tert-Butyl-4-((E)-2-cyano-ethenesulfonyl)-phenoxy]-N-(4-fluoro-benzyl)-acetamide;
2-[2-tert-Butyl-4-((E)-2-cyano-ethenesulfonyl)-phenoxy]-N-(3-methoxy-phenyl)-acetamide;
2-[2-tert-Butyl-4-((E)-2-cyano-ethenesulfonyl)-phenoxy]-N-(2-hydroxy-5-methyl-phenyl)-acetamide;
(E)-3-[3-tert-Butyl-4-(5-methyl-benzoxazol-2-yl-methoxy)-benzenesulfonyl]acrylonitrile;
4-[4-((E)-2-Cyano-ethenesulfonyl)-phenyl]-tetrahydro-pyran-4-carboxylic acid;
4-[4-((E)-2-Cyano-ethenesulfonyl)-phenyl]-tetrahydro-pyran-4-carboxylic acid cyclohexylamide;
4-[4-((E)-2-Cyano-ethenesulfonyl)-phenyl]-tetrahydro-pyran-4-carboxylic acid phenylamide; or
4-[4-((E)-2-Cyano-ethenesulfonyl)-phenyl]-tetrahydro-pyran-4-carboxylic acid 4-chloro-benzylamide;

or a pharmaceutically acceptable salt form thereof.

43. The method of claim 42 wherein the intra-abdominal cancer is located at or near the colon, at or near the ovary, at or near the rectum, at or near the stomach, or at or near the pancreas of the patient.

* * * * *

UNITED STATES PATENT AND TRADEMARK OFFICE
CERTIFICATE OF CORRECTION

PATENT NO. : 9,475,766 B2  
APPLICATION NO. : 13/975483  
DATED : October 25, 2016  
INVENTOR(S) : Bruce D. Dorsey et al.

Page 1 of 1

It is certified that error appears in the above-identified patent and that said Letters Patent is hereby corrected as shown below:

At Column 93, Line number 65:  
Please replace "$R_3$ is $-CH_3$" with -- $R_4$ is $-CH_3$ --

Signed and Sealed this  
Twenty-third Day of May, 2017

Michelle K. Lee  
*Director of the United States Patent and Trademark Office*